(12) United States Patent
Nesbitt

(10) Patent No.: US 7,390,326 B2
(45) Date of Patent: Jun. 24, 2008

(54) ANTI-MICROBIAL ELECTROSURGICAL ELECTRODE AND METHOD OF MANUFACTURING SAME

(75) Inventor: Bruce Nesbitt, Chicago, IL (US)

(73) Assignee: Orion, Industries, Ltd., Chicago, IL (US)

( * ) Notice: Subject to any disclaimer, the term of this patent is extended or adjusted under 35 U.S.C. 154(b) by 0 days.

(21) Appl. No.: 11/615,380

(22) Filed: Dec. 22, 2006

(65) Prior Publication Data

US 2007/0106294 A1     May 10, 2007

Related U.S. Application Data

(60) Division of application No. 10/649,199, filed on Aug. 27, 2003, now Pat. No. 7,160,297, which is a continuation-in-part of application No. 10/318,503, filed on Dec. 12, 2002, now abandoned.

(51) Int. Cl.
*A61B 18/14* (2006.01)
*B05D 1/12* (2006.01)

(52) U.S. Cl. .............................. 606/45; 606/49; 427/180

(58) Field of Classification Search ........................ None
See application file for complete search history.

(56) References Cited

U.S. PATENT DOCUMENTS

| | | | |
|---|---|---|---|
| 3,694,243 | A | 9/1972 | Campbell |
| 3,990,998 | A | 11/1976 | DeLuca et al. |
| 4,074,010 | A | 2/1978 | Knight |
| 4,074,718 | A | 2/1978 | Morrison, Jr. |
| 4,314,559 | A | 2/1982 | Allen |
| 4,338,360 | A | 7/1982 | Cavanagh et al. |
| 4,356,037 | A | 10/1982 | Novak |

(Continued)

FOREIGN PATENT DOCUMENTS

EP     0 479 482     4/1992

(Continued)

OTHER PUBLICATIONS

"Basics of Design Engineering" published by Penton Media, Inc. in 1999.

(Continued)

*Primary Examiner*—Lee S Cohen
(74) *Attorney, Agent, or Firm*—Bell Boyd & Lloyd LLP

(57) ABSTRACT

An electrosurgical device including a reinforcing underlayment having a non-stick, anti-microbial coating. In one embodiment, the coating includes a non-stick material having anti-microbial particles interspersed in the non-stick material. This coating is applied to the surfaces of the electrode to minimize the build-up of charred tissue on the surfaces of the electrode. Also, the coating tends to kill harmful organisms residing on the surfaces of the electrode. In another embodiment, a primer coating is initially applied to the surfaces of the electrode. A plurality of anti-microbial particles are then applied to the primer coating layer and engage and are embedded in the primer coating layer. A top coat including a non-stick material is applied to the anti-microbial particle layer. In either embodiment, the coating layers applied to the surfaces of the electrode are cured to harden and adhere the layers to the electrode.

115 Claims, 21 Drawing Sheets

U.S. PATENT DOCUMENTS

| | | |
|---|---|---|
| 4,486,508 A | 12/1984 | Coughlin et al. |
| 4,517,975 A | 5/1985 | Garito et al. |
| 4,547,923 A | 10/1985 | DeVries et al. |
| 4,605,564 A | 8/1986 | Kulla et al. |
| 4,785,807 A | 11/1988 | Blanch |
| 4,876,110 A | 10/1989 | Blanch |
| 4,900,710 A | 2/1990 | Soukiassian et al. |
| 4,987,157 A | 1/1991 | Smart et al. |
| 5,004,034 A | 4/1991 | Smart et al. |
| 5,016,401 A | 5/1991 | Mangus |
| 5,030,218 A | 7/1991 | Alexander |
| 5,078,082 A | 1/1992 | Van Dyk Soerewyn |
| 5,089,205 A | 2/1992 | Huang et al. |
| 5,100,402 A | 3/1992 | Fan |
| 5,167,989 A | 12/1992 | Dudek et al. |
| 5,169,675 A | 12/1992 | Bartoszek-Loza et al. |
| 5,185,184 A | 2/1993 | Koran et al. |
| 5,197,962 A | 3/1993 | Sansom et al. |
| 5,238,045 A | 8/1993 | Park et al. |
| 5,243,251 A | 9/1993 | Inukai et al. |
| 5,250,356 A | 10/1993 | Batzar |
| 5,324,257 A | 6/1994 | Osbourne et al. |
| 5,380,320 A | 1/1995 | Morris |
| 5,382,247 A | 1/1995 | Clmlno et al. |
| 5,413,788 A | 5/1995 | Edwards et al. |
| 5,415,626 A | 5/1995 | Goodman et al. |
| 5,460,661 A | 10/1995 | Maynard, Jr. |
| 5,473,018 A | 12/1995 | Namura et al. |
| 5,476,552 A | 12/1995 | Tucker et al. |
| 5,492,769 A | 2/1996 | Pryor et al. |
| 5,496,270 A | 3/1996 | Nettekoven |
| 5,496,315 A | 3/1996 | Weaver et al. |
| 5,531,743 A | 7/1996 | Nettekoven et al. |
| 5,535,904 A | 7/1996 | Tucker |
| 5,579,725 A | 12/1996 | Boshears |
| 5,588,634 A | 12/1996 | Nettekoven |
| D377,524 S | 1/1997 | Lipp |
| 5,591,141 A | 1/1997 | Nettekoven |
| 5,607,683 A | 3/1997 | Capelli |
| 5,624,704 A | 4/1997 | Darouiche et al. |
| 5,626,907 A | 5/1997 | Hagiwara et al. |
| 5,643,256 A | 7/1997 | Urueta |
| 5,670,557 A | 9/1997 | Dietz et al. |
| 5,683,747 A | 11/1997 | Hamon |
| 5,693,050 A | 12/1997 | Speiser |
| 5,693,052 A | 12/1997 | Weaver |
| 5,697,926 A | 12/1997 | Weaver |
| 5,702,387 A | 12/1997 | Arts et al. |
| 5,752,951 A | 5/1998 | Yanik |
| 5,756,145 A | 5/1998 | Darouiche |
| 5,792,109 A | 8/1998 | Ladd |
| 5,792,544 A | 8/1998 | Klein |
| 5,792,570 A | 8/1998 | Ishikawa et al. |
| 5,800,427 A | 9/1998 | Zamba |
| 5,807,608 A | 9/1998 | O'Dell et al. |
| 5,814,392 A | 9/1998 | You et al. |
| D399,561 S | 10/1998 | Ellingson |
| 5,817,325 A | 10/1998 | Sawan et al. |
| D402,030 S | 12/1998 | Roberts et al. |
| D402,031 S | 12/1998 | Roberts et al. |
| 5,843,080 A | 12/1998 | Fleenor et al. |
| 5,846,237 A | 12/1998 | Nettekoven |
| 5,885,280 A | 3/1999 | Nettekoven et al. |
| 5,885,281 A | 3/1999 | Urueta |
| 5,893,849 A | 4/1999 | Weaver |
| 5,902,283 A | 5/1999 | Darouiche et al. |
| 5,902,301 A | 5/1999 | Olig |
| 5,925,039 A | 7/1999 | Landingham |
| 5,925,043 A | 7/1999 | Kumar et al. |
| 5,997,517 A | 12/1999 | Whitbourne |
| 6,004,317 A | 12/1999 | Speiser |
| 6,004,318 A | 12/1999 | Garito et al. |
| 6,017,741 A | 1/2000 | Keogh |
| 6,039,735 A | 3/2000 | Greep |
| 6,053,910 A | 4/2000 | Fleenor |
| 6,063,207 A | 5/2000 | Yu et al. |
| 6,066,137 A | 5/2000 | Greep |
| 6,070,444 A | 6/2000 | Lontine et al. |
| 6,071,283 A | 6/2000 | Nardella et al. |
| 6,083,221 A | 7/2000 | Fleenor et al. |
| 6,090,107 A | 7/2000 | Borgmeier et al. |
| 6,132,427 A | 10/2000 | Jones et al. |
| 6,159,412 A | 12/2000 | Fletcher et al. |
| 6,168,580 B1 | 1/2001 | Yardley |
| 6,174,309 B1 | 1/2001 | Wrublewski et al. |
| 6,213,995 B1 | 4/2001 | Steen et al. |
| 6,214,000 B1 | 4/2001 | Fleenor et al. |
| 6,221,739 B1 | 4/2001 | Gorelik |
| 6,228,753 B1 | 5/2001 | Lo et al. |
| 6,238,686 B1 | 5/2001 | Burrell et al. |
| 6,258,201 B1 | 7/2001 | Krech |
| 6,270,831 B2 | 8/2001 | Kumar et al. |
| 6,270,903 B1 | 8/2001 | Feng et al. |
| 6,273,875 B1 | 8/2001 | Siman et al. |
| 6,287,632 B1 | 9/2001 | Nishio et al. |
| 6,291,084 B1 | 9/2001 | Darolia et al. |
| 6,297,564 B1 | 10/2001 | Chung |
| 6,306,176 B1 | 10/2001 | Whitbourne |
| 6,332,490 B1 | 12/2001 | Griggs |
| 6,394,595 B1 | 5/2002 | Jiang et al. |
| 6,409,725 B1 | 6/2002 | Khandkar et al. |
| 6,416,546 B1 | 7/2002 | Kimura et al. |
| 6,446,814 B1 | 9/2002 | King |
| 6,454,764 B1 | 9/2002 | Fleenor et al. |
| 6,475,253 B2 | 11/2002 | Culler et al. |
| 6,511,479 B2 | 1/2003 | Gentelia et al. |
| 6,514,517 B2 | 2/2003 | Jamiolkowski et al. |
| 6,528,107 B2 | 3/2003 | Chinn et al. |
| 6,544,258 B2 | 4/2003 | Fleenor et al. |
| 6,558,686 B1 | 5/2003 | Darouiche |
| 6,582,424 B2 | 6/2003 | Fleenor et al. |
| 6,607,528 B1 | 8/2003 | Quick et al. |
| 6,617,142 B2 | 9/2003 | Keogh et al. |
| 6,683,120 B2 | 1/2004 | Munro |
| 6,685,704 B2 | 2/2004 | Greep |
| 6,719,991 B2 | 4/2004 | Darouiche et al. |
| 6,726,979 B2 | 4/2004 | Friedman et al. |
| 6,783,525 B2 | 8/2004 | Greep et al. |
| 6,921,390 B2 | 7/2005 | Bucay-Couto et al. |
| 6,951,559 B1 | 10/2005 | Greep |
| 7,081,133 B2 | 7/2006 | Chinn |
| 2001/0021848 A1 | 9/2001 | Fleenor et al. |
| 2001/0031964 A1 | 10/2001 | Gentelia et al. |
| 2002/0111622 A1 | 8/2002 | Khandkar et al. |
| 2002/0113066 A1 | 8/2002 | Stark et al. |
| 2002/0182383 A1 | 12/2002 | Phillips et al. |
| 2003/0109864 A1 | 6/2003 | Greep et al. |
| 2003/0109865 A1 | 6/2003 | Greep |
| 2003/0163125 A1 | 8/2003 | Greep |

FOREIGN PATENT DOCUMENTS

| | | |
|---|---|---|
| EP | 0 761 174 | 3/1997 |
| EP | 0 779 060 | 6/1997 |
| WO | WO 98/18396 | 5/1998 |

OTHER PUBLICATIONS

"The Remarkable Fluoropolymer Coating That Lasts 100 Times Longer Than Other Coatings" by Whitford Corporation, published prior to 2002.

"Utah Medical Products Inc. Specialized Dissection Electrodes" from http://www.utahmed.com/dissect.htm, 2000-2002 (Last modified: May 30, 2002).

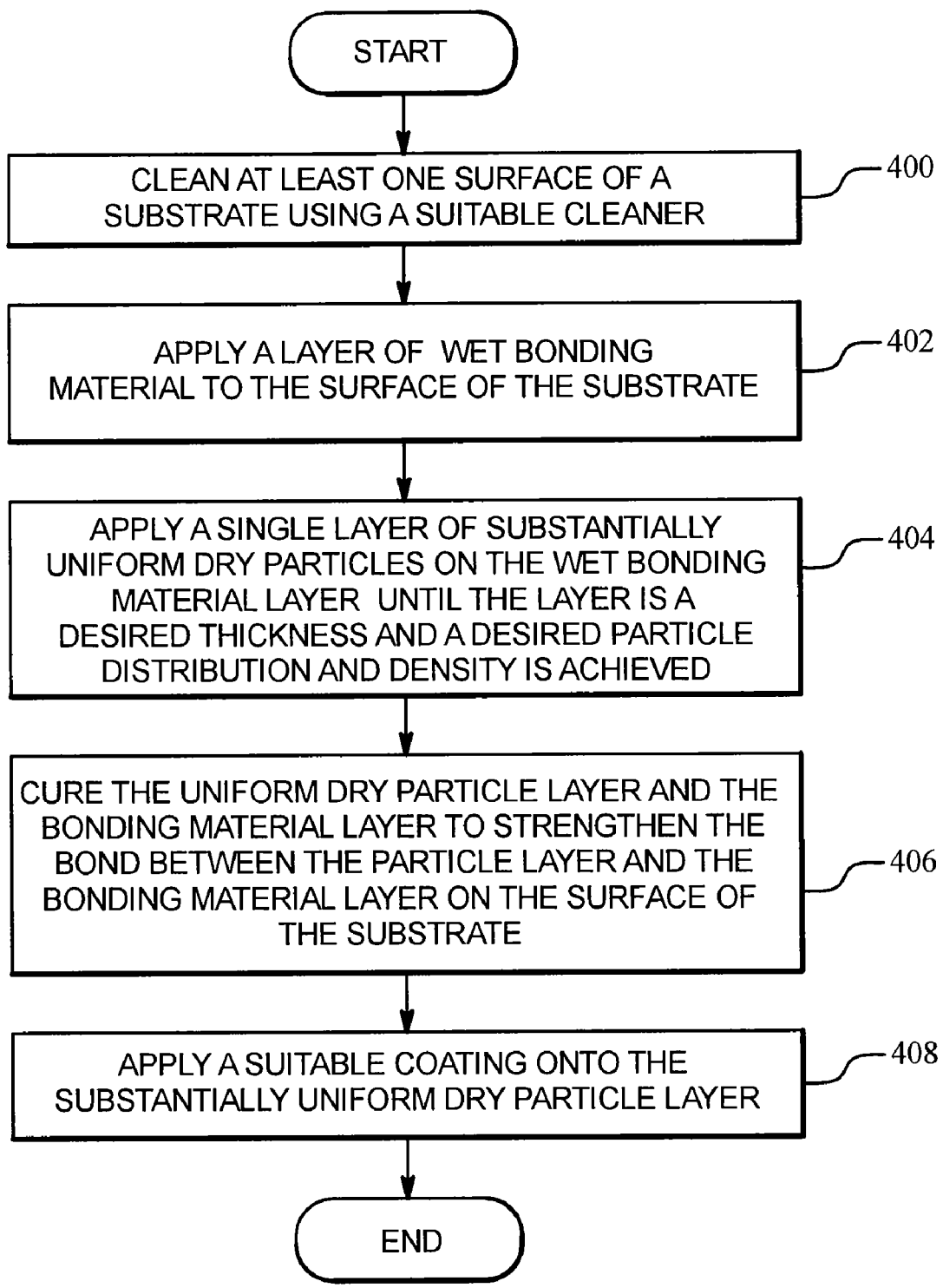

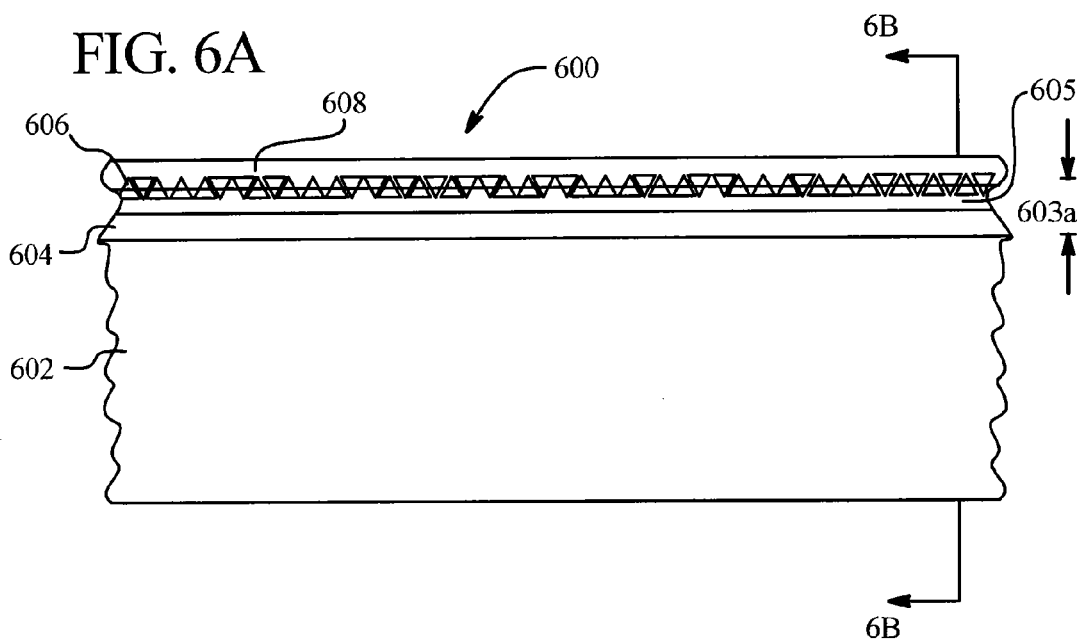
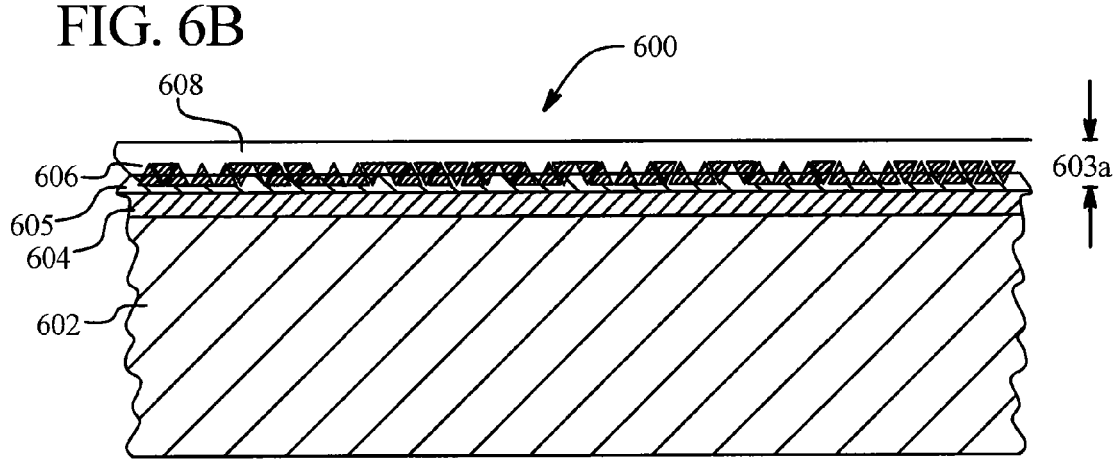
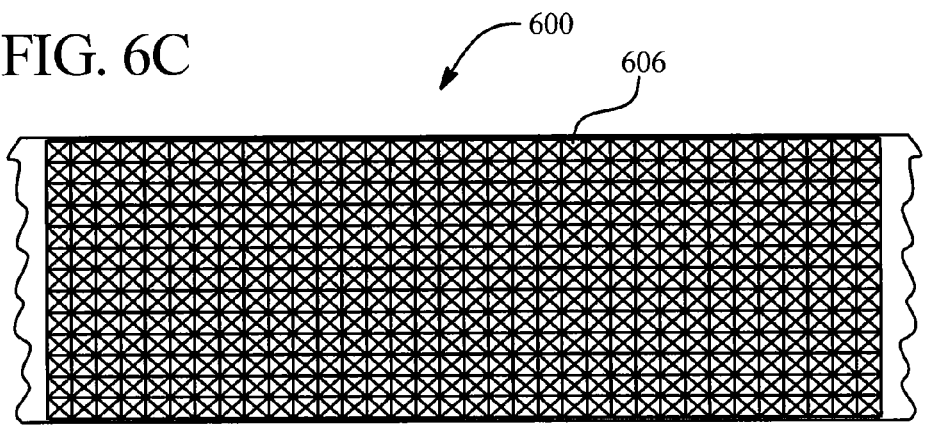

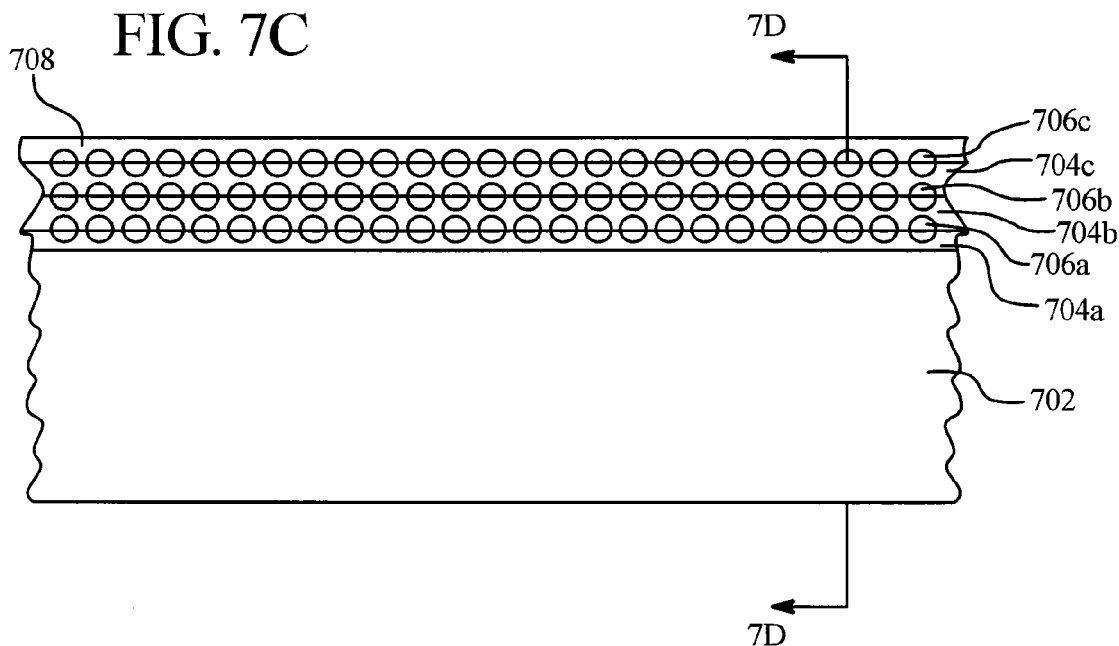
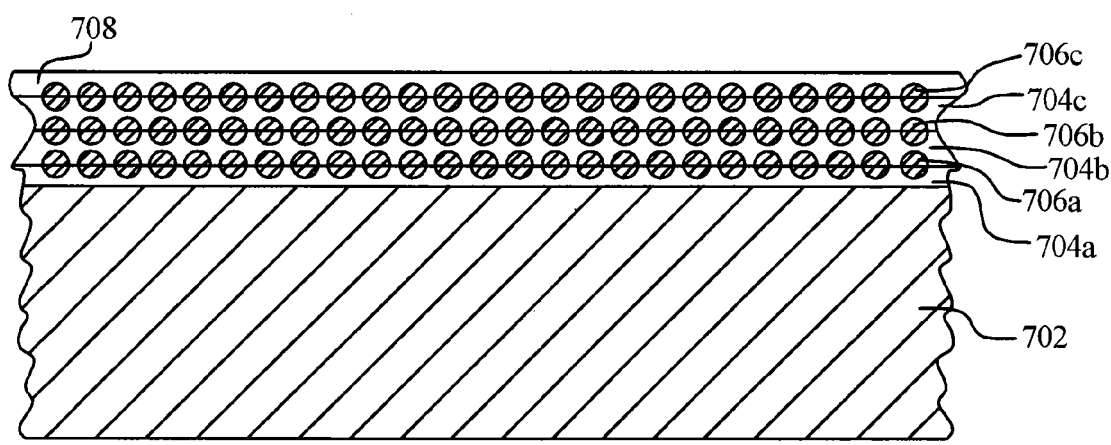

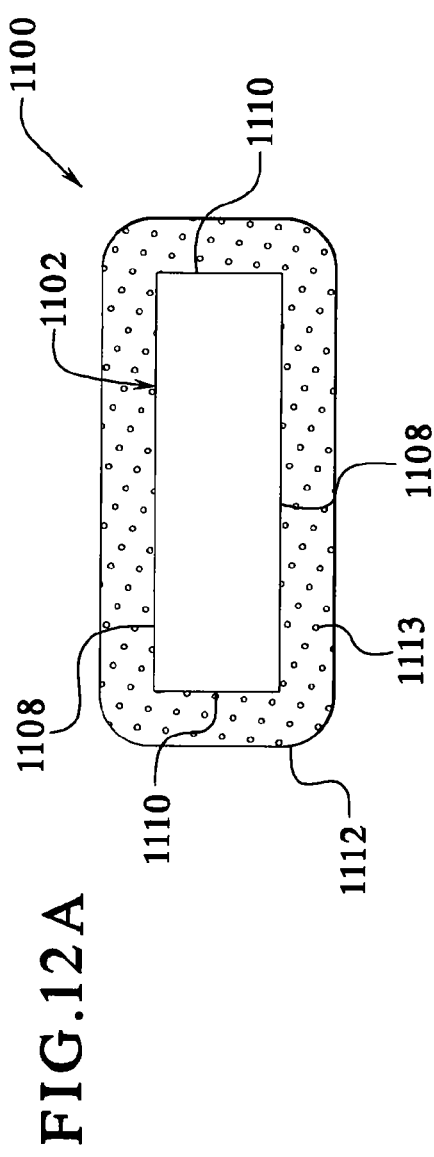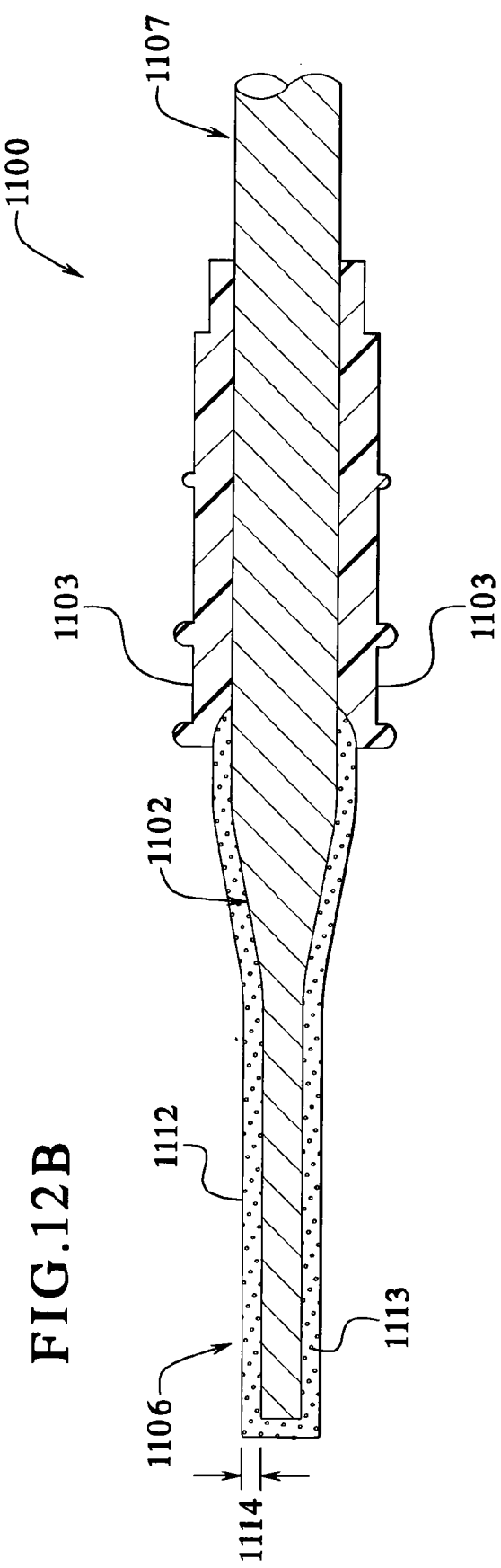
FIG.12A
FIG.12B

ANTI-MICROBIAL ELECTROSURGICAL ELECTRODE AND METHOD OF MANUFACTURING SAME

PRIORITY CLAIM

This application is a divisional of and claims the benefit of U.S. patent application Ser. No. 10/649,199, filed Aug. 27, 2003, now U.S. Pat. No. 7,160,297, which is a continuation-in-part of, and claims priority to and the benefit of U.S. patent application Ser. No. 10/318,503, filed Dec. 12, 2002, now abandoned.

CROSS REFERENCE TO RELATED APPLICATIONS

This application relates to the following co-pending commonly owned patent application: "TETRAFLUORETHYLENE PERFLUOROMETHYL VINYL ETHER COPOLYMER COATED GLASS AND METHOD OF MANUFACTURING SAME," Ser. No. 11/107,234, "ELECTROSURGICAL ELECTRODE AND METHOD OF MANUFACTURING SAME," Ser. No. 11/637,446, "ELECTROSURGICAL ELECTRODE AND METHOD OF MANUFACTURING SAME," Ser. No. 11/637,445, "ANTI-MICROBIAL ELECTROSURGICAL ELECTRODE AND METHOD OF MANUFACTURING SAME," Ser. No. 11/615,395, "COATING REINFORCING UNDERLAYMENT AND METHOD OF MANUFACTURING SAME," Ser. No. 11/844,708, and "ANTI-MICROBIAL ELECTROSURGICAL ELECTRODE AND METHOD OF MANUFACTURING SAME," Ser. No. 11/925,341.

BACKGROUND OF THE INVENTION

Electrosurgery refers to surgical procedures that pass high frequency, alternating electrical current through body tissues to cut or coagulate the tissues. Electrosurgical instruments or tools such as electrosurgical electrodes are used in these surgical operations to cut, coagulate and cauterize the tissue of a patient. The electrodes conduct the high frequency alternating electrical current from a generator to the patient to perform these operations. The generator is the source of the electricity for the surgical procedure. Because standard electrical current alternates at a frequency of sixty cycles per second (60 Hz), which could cause excessive neuromuscular stimulation and possibly electrocution if used, the generator takes sixty cycle current and increases the frequency to over 300,000 cycles per second (300,000 Hz). At this frequency, the electrical energy can pass through the patient with minimal neuromuscular stimulation and no risk of electrocution. Additionally, the generators are able to produce a variety of electrical waveforms. A constant waveform, which produces heat very rapidly, is generally used to vaporize or cut body tissue. An intermittent waveform produces less heat and is generally used to coagulate body tissue. Several different waveforms may be used in an electrosurgical procedure to achieve different effects.

As described above, electrosurgical electrodes are used to cut or coagulate the body tissue in an electrosurgical procedure. Many sizes and shapes of electrosurgical electrodes such as blades, scalpels, needles, wire forms, balls and probes are available. Most electrosurgical electrodes are made of metal, typically stainless steel. Generally, a portion of the electrode is sheathed or encapsulated with an insulative material such as a plastic material. The electrodes are typically inserted into and connected to a handpiece for manipulating the electrode during surgery.

The working surface of the electrosurgical electrode or the exposed end of the electrode is not encapsulated with plastic or any type of electrically insulative material. The working surface generates heat and therefore is subject to high temperatures during use. The high temperature causes the body tissues to tend to stick to the working surface of the electrode. Specifically, the elevated temperature of the electrode causes charred tissue, commonly called "eschar," to adhere or stick to the working surface of the electrode. The buildup of tissue or eschar on the working surface of the electrode negatively effects the performance of the electrode during surgery. In particular, a buildup of tissue on the electrode reduces the transfer of energy to and from the electrode which decreases the cutting effectiveness of the electrode. Additionally, the tissue buildup may obscure the vision of the surgeon and therefore make it more difficult to perform the surgery.

As a result, efforts are made during surgery to keep the working surface of the electrode clean. Such cleaning methods include rubbing, brushing or scraping the electrode surface against a scouring pad or other suitable cleaning device. The continuous cleaning of the surface of the electrode, however, prolongs the surgical procedure which is not desirable. Therefore, the surgeon is left with the options of replacing the electrode during surgery, accepting reduced performance of the electrode, or expending valuable time and energy to thoroughly clean the surface of the electrode.

One method used to solve the problem of tissue or eschar buildup on the surface of the electrode is to coat the surface of the electrode with a non-stick or surface release coating. The non-stick or release coating minimizes the sticking or adherence of the tissue on the surface of the electrode and enables the built up tissue to be removed more easily and efficiently from the surface.

Several different types of non-stick coatings have been applied to electrosurgical electrodes. Some of the different non-stick coatings or materials include fluorinated materials polytetrafluoroethylene, perfluoro-alkoxy, MFA, silicone, ceramic composites, paralyene silane polymers and other suitable non-stick coatings. Different methods exist for applying the non-stick coating to the surface of the electrosurgical electrodes. However, the non-stick or release coatings are electrically insulative, and therefore, may impair the electrical conductivity of the surface of the electrodes.

Another issue associated with surgical instruments such as electrosurgical electrodes is the sterilization or cleanliness of the working surface and other surfaces of the electrode as the electrode contacts tissue and other parts of the body. The tissue or eschar buildup on the working surface of the electrode creates an environment where bacteria and other harmful organisms may cultivate and be introduced into the body during the surgical process. Furthermore, any gaps between the plastic sheath and the electrode or any fractures, fissures or other defects in the plastic sheath enables bacteria and other organisms to get underneath the plastic sheath and also into and grow in the fractures, fissures and defects or other interstices in the plastic sheath. This further promotes the growth of the bacteria and the harmful organisms which may migrate to the surface of the electrode or to the patient.

Additionally, if the sterilization of the electrode is not performed properly, not performed routinely or consistently or not performed at all, which is more common in some second and third world countries, bacteria and other harmful organisms will adhere to and grow on the surface of the electrode and then enter a patient's body during a surgical procedure. As described above, this can cause significant difficulties and complications for the patient after the surgical procedure is complete. As a result, minimizing the growth of bacteria and other organisms on the electrode surface is desirable to enable the electrode to be used multiple times without requiring sterilization if unavailable and minimize and/or prevent infections or other related complications from developing in a patient following surgery.

Accordingly, there is a need for an improved electrosurgical device such as a single use or multi-use electrosurgical electrode and method of manufacturing same which minimizes the buildup of tissue on the substrate or working surface of the electrode and also minimizes the growth of bacteria or other harmful organisms on the substrate or surface of the electrode during storage, use or pauses in the use of the electrode.

SUMMARY OF THE INVENTION

The present invention relates in general to coated substrates, and specifically to a coating reinforcing underlayment for coating substrates on which a topcoat such as PTFE, will be applied and a method of manufacturing the coating reinforcing underlayment.

One embodiment of the coating reinforcing underlayment of the present invention is applied to a substrate, which may be any suitable substrate, and which includes a layer of a wet bonding material applied to the surface of the substrate to be coated and a single layer of substantially uniform dry particles applied directly into and to the wet bonding material layer. In another embodiment, the above process is repeated until a desired thickness is achieved or until a specific number of layers are applied to the surface of the substrate.

In one presently preferred embodiment of the method of the present invention, a substrate is positioned on a support so that a surface or surfaces of the substrate may be coated. Initially, the surface of the substrate is cleaned with a cleaner to remove impurities which may be present on the surface of the substrate. The cleaner such as a solvent may be manually applied or mechanically applied to the substrate. In one embodiment, grit blasting or sandblasting is used to clean the surface of the substrate. Alternatively, the substrate may be pre-cleaned or the method may be performed in a "clean room" where the cleaned part is manufactured and the step is not necessary.

Once the surface of the substrate is cleaned, a layer of a wet bonding material such as a primer is applied to the surface of the substrate. The wet bonding material may include one or more additives which change or enhance one or more characteristics of the wet bonding material. For example, in one embodiment, the wet bonding material includes an ultraviolet light cure resin. In another embodiment, the wet bonding material includes an electron beam cure resin. It should also be appreciated that the bonding material may be any suitable bonding material or agent. The bonding material layer is formulated to also improve the bonding capabilities of the subsequent coating layer or layers applied to the surface of the substrate in addition to retaining the particles. The layer of wet bonding material is preferably applied uniformly so as to avoid forming a thick layer, which is thicker than what is necessary or required, and avoid drippings which may detract from the bonding ability to the substrate.

In one embodiment, while the bonding material layer is still wet, a single layer of substantially uniform dry particles such as a powdered engineering plastic, dry metal particles, dry ceramic particles or pre-coated or micronized dry particles or a combination of these particles are sprayed over the wet bonding material. The powdered or dried particles adhere to the wet surface area of the bonding material in an even manner. In this embodiment, when the wet bonding material is completely coated with one layer of the uniform powdered particles, additional dry particles cannot stick to the bonding material layer because the adhered particles attached to the bonding material layer act as a barrier to other particles attaching to the wet bonding material layer. Therefore, the dry particles do not build up or form an uneven surface area on the surface of the substrate. Additionally, the wet bonding material layer may be a thick layer where the uniform particles sink into and are completely covered by the wet bonding material layer. In another embodiment, the wet bonding material layer is a substantially thin layer on the surface of the substrate and a substantial portion of the particles are exposed on the wet bonding material layer. Once applied, the dry particles substantially increase the surface area of the substrate.

The substantially uniform dry particles are preferably consistent or include particles that have substantially consistent granular size and shape. In one embodiment, the particles are substantially round in shape. It should be appreciated that any suitable size or shaped particles may be employed in the present method such as flat-shaped, flake-shaped, cylindrical-shaped, oblong-shaped or leaf-shaped particles to suit the end use of the part being coated with this process. In one embodiment, the dry particle sizes and shapes are determined based on the end use and desired specifications and chemical composition of the coated substrate.

In one example, angular particles such as triangular shaped particles or similar particles are used to create a rough surface on a substrate by applying the angular particles to the bonding material layer on the surface of the substrate. In another example, less abrasive and lower friction surfaces are created by using shaped particles such as spherical or round shaped particles. In a further example, one or more combinations of different shaped uniform particles are used on a surface of a substrate. Thus, uniformly sized or shaped groups of uniform particles or different sized or shaped particles may be applied to a surface of a substrate. The wet bonding material layer and the substantially uniform dry particle layer are applied to the surface of the substrate until a desired thickness is achieved. Any suitable thickness ranges may be used as desired and determined by the manufacturer. Additionally, the density of the particles may vary depending on the design specifications of an end product or final product. The density or distribution of the particles may vary from covering or adhering to approximately ten percent of the surface of the substrate to approximately one hundred percent of the surface. Similarly, the density of the uniform particles may vary depending on the end use criteria.

In another embodiment, low friction uniform particles are applied to a lower layer followed by another very thin outer or upper layer of very fine abrasive particles. This system initially micro-abrades and smoothes out a counterface or counter surface of relatively rough metal which the coating wears against until the abrasive layer is worn down. After the thin abrasive layer is worn, the underlying layer of non abrasive friction reducing particles provides low friction to the now smooth counterface or opposing surface. This embodiment may for instance be used in shock absorbers where a low quality relatively rough metal internal surface of tubing is wearing against a coated piston.

The types of coatings and/or uniform particles applied to a substrate may be any suitable type of particle as generally as indicate above. In one embodiment, whisker or rod shaped particles such as carbon fibers or carbon whiskers or nickel whiskers are applied to a surface of a substrate to reduce wear on the surface and provide a non-metallic or metallic conductive surface for industries where electrically conductivity is an issue or a requirement. In another embodiment, aramid fibers or engineered plastic particles or fibers are applied to a substrate to strengthen the surface of the substrate. The aramid fibers include Kevlar® or Nomex® fibers which are introduced in substantially the same manner as the carbon fibers or whiskers. The Kevlar® or Nomex® fibers or materials can be either a pulp, which includes loose, fluffy fibers which is further ground into fibrillated fine powder, or can be other suitable forms such as round particles or semi-round dry particles. The aramid particles provide non-metallic wear resistance and have good bonding ability with both the basecoat and subsequent topcoats. Thus, the applied aramid fibers or materials create a dense layer of aramid or Kevlar® particles on the surface of the substrate, which is then coated with a topcoat or other suitable final coating. However, if a very high temperature, moderate friction (i.e., low abrasion) surface is desired, a topcoat or final coating is not applied to the layer of aramid fibers. In another embodiment, diamond particles are applied to the wet bonding material layer. Although this option has a much greater cost than other particles, the diamond particles provide greater wear resistance and less friction with enhanced electrical properties on the surface. These particles add tribological benefits beyond those benefits of aramid fibers.

In another embodiment, specially treated, uniform plastic particles are applied to a surface of a substrate. The plastic particles can be pre-treated PTFE, ultra high molecular weight polyethylene (UHMW) and/or PE or another suitable material are applied to the wet bonding material on the surface of the substrate. The particles are irradiated or processed with an electron beam which causes changes to the surface of the particles, allowing them to wet more easily and to sink into the wet bonding material layer, instead of remaining on the top of the material bonding layer. Therefore, the plastic particles are strongly bonded to the layer and not easily dislodged from the surface. This process thereby enables the plastic particle layer to last longer.

In another alternate embodiment, anti-microbial particles such as silver or silver compounds are applied to the surface of a substrate to reduce and kill bacteria and other potential germs that may be located on a surface of a substrate such as a kitchen counter or a food storage vessel, container or a conveyor or hook in a meat packing facility. In this embodiment, a dense layer of anti-microbial material in a powder or particulate form is applied to the wet bonding material layer. In one aspect of this embodiment, the anti-microbial particle layer is the final layer. In another aspect, a thin topcoat or final coating is applied to the anti-microbial particle layer to provide a release or non-stick surface on the substrate. The above process can be repeated as necessary to maintain the effectiveness of the anti-microbial surface. In this aspect, the thin topcoat or topcoats do not completely cover the protruding anti-microbial particles.

In another embodiment, dry or powdered, ultra porous bronze or brass particles are applied to the wet bonding material layer on the surface of a substrate. The ultra porous bronze or brass particles include many openings and voids so that the particles are approximately seventy percent solid compared to over ninety percent solid for most porous bronze or brass materials. The particles enable a user to infuse the very porous bronze or brass particles with the wet bonding material after the bronze or brass particles are deposited on the wet bonding material on a surface of a substrate. This method is used to add lubrication and "lock" or strongly secure the particles into the liquid bonding material layer to increase the bonding strength of the layers to hold the bronze or brass particles to both the upper and lower coating layers on the surface of the substrate even after being exposed to abrasive forces. The particles may be any suitable porous metal particles such as stainless steel particles, nickel particles, bronze particles, brass particles, iron particles, titanium particles or other suitable particles including a metal and/or metal alloys.

In another embodiment, porous metal particles such as the bronze particles described above are impregnated or infused with a material such as PTFE, which lowers the friction of the particles. In one aspect of this embodiment, bronze particles or any other suitable metal particles including approximately seventy percent voids (i.e., air) are vacuum impregnated with a suitable lower friction material such as PTFE. In another aspect of this embodiment, the bronze particles are soaked with the PTFE and then dried. The latter process leaves partial voids in the bronze particles. However, the particles are partially infused with PTFE, which adds low friction capabilities to the bronze.

In a further embodiment, catalyzed resins consisting of two parts or plural components such as epoxies or urethanes are used to coat a surface of a substrate. In one example, these catalyzed bonding agents are used to coat a substrate such as a plastic or low temperature metal to enhance the wear resistance of the surface of the plastic or metal while not affecting the strength of the plastic or metal.

In another embodiment, acid or chemical resistance is increased by applying non-metallic, non-plastic particles such as substantially uniform dry ceramic or mica flakes and/or mica particles to the wet bonding material layer. Other suitable particles may be used such as glass, ceramics, modified mica, boron nitride, silicon nitride and aluminum oxide particles. The dry ceramic or mica flakes and/or particles create a barrier or a substantial barrier to an acid or other chemical. The barrier created by the particles or flakes diverts the acid or chemical from directly attacking a base material such as a metal, by decreasing the inherent permeability and porosity of a base coating or coatings on the surface of a substrate. A torturous, indirect path or maze-like path chemicals must take to reach the underlying surface is created by the plates or flakes so that the chemical or acid is forced to take an indirect path around the mica particles or flakes thereby slowing and/or retarding the speed and dynamics of the chemical or acid that is trying to permeate the coating.

Once the plural component resin followed by dry particles are applied to the surface of the substrate, the bonding material and substantially uniform dry particle layer are cured by catalytic cure, by heating the layers, air-drying the layers or according to any suitable curing method. The curing process cures the resin or dry particles so that a strong bond develops between the substantially uniform dry particle layer and the wet bonding material layer as it hardens and also bonds to the base surface. Because the dry uniform particles were applied to the wet bonding material, the particles are tightly packed and form a single uniform, substantially even surface on the substrate. As a result, the substantially uniform dry particles increase the surface area on the substrate and enable a topcoat to be applied uniformly and evenly on the substrate. Additionally, the topcoat develops a strong bond with the dry particles below which is bonded to the substrate. This process may be repeated one or more times to increase the total thickness and chemical resistance of the coatings on the surface of the substrate.

In another embodiment, a wet bonding material layer including relatively small particles of a suitable low friction or soft material is first applied to the surface of a substrate. Next, a layer of uniform hard dry particles or other suitable hard particles is applied to the wet bonding material layer. Another layer of the initial wet bonding material mixture including the relatively smaller particles is then applied to the dry particle layer. The layers are dried using a suitable drying or curing process, which causes the top layer or second wet bonding material layer including the small soft particles to shrink and distribute the small soft particles amongst the hard particles. This creates an abrasion resistant and low friction surface.

The spraying or application of the dry particles to the wet bonding material layer on the surface of the substrate may be adjusted to enhance the strength of the bond between the bonding material and the dry particles and the density of the layers on the substrate. In one embodiment, the pressure of the dry particle spray and the rate of the spray is increased to increase the density of the particles in the material bonding layer. The greater the density of the particles and depth of the layers, the greater the strength and desired characteristics of the resultant coated substrate.

In another embodiment, an electrostatic, tribo-charged or opposite electrostatic charged powder spray method is used to apply the dry particles to the wet bonding material. The charged particle powder spray enables an operator to better control the application uniformity of the dry particles and thereby enhance the density and application of the dry particles to the wet bonding material on the substrate. In a further embodiment, the electrostatic powder spray is used to apply a topcoat over the dry particles such as a powder paint coating or fluoronated plastic powder coating to the surface of the substrate. In this embodiment, a bonding material and then a conductive material or thin conductivity enhancing coating is applied to the surface of the substrate. The powder topcoat or final coating is then cured in a convection or infrared oven, which heats and shrinks the powder coating onto the top of the dry particles.

In another embodiment, an applicator such as a sifter is used to uniformly apply the uniform particles to the wet bonding material layer. The sifter is similar to a conventional flour sifter and is used in certain applications depending on the size of the uniform particles.

In a further embodiment, ferromagnetic or magnetic dry particles are applied to a surface of a substrate to completely coat a surface of a substrate or form a shape, symbol, character or other suitable image on a surface of a substrate. Initially, a non-magnetic metal surface or glass surface or aluminum surface is coated with a wet bonding material. Magnetic particles such as special magnetic stainless steel, magnetic ferrite or ferrous particles are applied to the wet bonding material. These magnetic particles are attracted to the magnetic shape or symbol lying directly under the wet coated glass, aluminum or non-magnetic substrate, thereby creating a design in the finished coating.

In another embodiment, a surface or a portion of a surface of a substrate such as the surface of a part is masked or selectively coated with a suitable masking device or material so that the dry uniform particles can only be applied to the unmasked areas on the surface of the substrate. In this embodiment, the wet bonding material is generally applied to the entire surface or surfaces of the substrate and then a masking material or device is applied to a specific area or areas on the surface of the substrate. However, the wet bonding material layer can be applied to a pre-masked substrate to coat the selective areas of the substrate. Therefore, the dry uniform particles, which are subsequently applied to the surface of the substrate, adhere to the exposed portions of the wet bonding material layer but not the masked portions of the surface of the substrate.

The coating layer applied to the underlayment or wet layer and the dry second layer may be any suitable coating such as a topcoat layer. It should be appreciated that the method of manufacturing or forming the coating underlayment may be performed as described above by applying or spraying the coatings onto the surface of the substrate. Alternatively, the coatings and dry particles may be applied using other suitable coating and application methods. In one embodiment, the wet bonding material layer is applied by dipping the substrate either completely or partially in the wet bonding material layer.

Several different types of additives may be added to the topcoat or final coating to improve the performance characteristics of the coated substrate. In one embodiment, a counter face smoothening additive including relatively hard particles, is added to a topcoat or final coat, in either a liquid or dry powder form, to enable the coated substrate to smoothen or polish a rough surface or surfaces, which contact the surface of the coated substrate. It should be appreciated that any suitable additive may be added to the topcoat or final coating to improve the performance or desired characteristics of the coated substrate.

In another embodiment, the substrate previously coated with a wet bonding material layer and dry particle layer, may be electrostatically charged to attract the uniform dry particles having an opposite charge. In this embodiment, substantially uniform dry powder particles are electrostatically attracted to the substrate because the particles have an opposite charge to the surface of the substrate. In one example, a powder paint coating such as an epoxy or polyester is applied to a surface of a substrate. In this example, a liquid layer is applied to a surface of a substrate and then an electrically conductive dry particle material layer is applied to the surface. The powder coating is then applied and is electrostatically attracted to the conductive material outer layer. Because the powder coating does not include solvent, the coatings are cured in a convection or infrared oven even though the lower layer of the basecoat contains specific solvents. The solvents in the basecoat migrate through the dry powder before the top powder coat starts to jell and cure into a continuous coating. The powder coating heats up and shrinks over the top of the dry particle layer forming a uniform, evenly distributed topcoat layer on the surface of the dry particle layer.

Alternatively, non-electrical, tribo-charged dry paint topcoat particles can be applied to a grounded part. In this embodiment, a very thin wet layer remains wet while the powder coat is applied either electrostatically or via a tribo-charge (i.e., friction charge). The entire coated part is oven cured to simultaneously cure the wet and dry powder topcoats.

In another embodiment, the substantially uniform aluminum oxide particles are applied to a wet bonding layer surface of a substrate to achieve a desired roughness on the surface. The desired surface roughness is achieved by changing the size of the aluminum oxide particles applied to the surface. The application of the aluminum oxide particles to roughen a surface substantially minimizes the distortion to the surface, which occurs with conventional blasting methods, and enables a user to control the roughness of the surface. In addition, harder particles such as boron nitride particles or other suitable particles can be applied to the surface of the substrate to increase the penetration resistance of the surface.

In a further alternative embodiment, the dry uniform particles are pre-coated or encapsulated or micro-encapsulated or micronized with a bonding enhancing material prior to applying the dry particles to the wet bonding material layer on the surface of the substrate. The pre-treated particles further enhance the bonding strength of coated particles to the layers on the substrate and to subsequent topcoat layers. The wet bonding material used to pre-coat the dry particles may be the same or different than the bonding material layer applied to the substrate.

In one embodiment, the present method described above is used as a coating to attenuate or reduce magnetic, electromagnetic, radio or similar waves generated by electric machines or other devices. Electromagnetic absorbent particles such as metal particles are used to coat a surface or surfaces. The particles completely coat the surfaces and enhance the electromagnetic, microwave or other wave absorbing capabilities of the surfaces.

In one embodiment, the present invention may be employed to protect machine operators from potentially dangerous conditions. Certain machines such as a Magnetic Resonance Imaging ("MRI") machines produce potentially harmful conditions. Generally, a MRI machine uses a nuclear magnetic resonance spectrometer to produce electronic images of specific atoms and molecular structures in solids, especially human cells, tissues, and organs. Exposure to the magnetic frequencies and radiation generated by a MRI machine over time may pose health risks to an operator. Similarly, it is desirable to block exterior magnetic fields from such equipment. Operators are protected and such equipment is usually protected from exterior magnetic fields by RF enclosures or magnetically shielded enclosures. Such enclosures include walls of layers of magnetic shielding material such as copper. Such materials including the fabrication and installation of such materials is relatively expensive. In accordance with the present invention, dense adsorptive coatings can be applied to the interior and/or exterior surfaces of the walls of such enclosures and made of less expensive materials. The dry particles can be round or flat flakes or combinations of, for instance, dry copper round and flat particles, assuring complete electrical conductivity. The dry coating or wet coatings can incorporate substances such as metals, which shield and absorb the magnetic frequencies and radiation. If the coatings are applied in a high vibration area, elastomeric urethanes and other suitable flexible bonding materials may be used to prevent cracking or separations on the coated substrate.

In another embodiment, a liquid bonding material layer such as an epoxy, which is thermally cured, is applied to the surface of the substrate. Metal particles are then introduced or applied using a dry powder spray mechanism. In one aspect of this embodiment, the metal particles are passed through a heating chamber or flame device, such as on a metal spray gun. The metal particles pass through an oxyacetylene flame raising the temperature of the particles as the particles are propelled towards the pre-applied wet bonding layer. Introduction of heat into the particles allows the wet bonding material layer to start curing or semi-curing. The curing or semi-curing occurs because the heat introduced into the coating starts to harden the bonding material layer after the particles have been immersed in the material layer due to the velocity and force of the particles propelled at the wet bonding material layer. In a further embodiment, several different metals are applied to the bonding material. In another embodiment, metals and non-metals are combined and applied to the bonding material layer to form the underlayment. Additionally, particles formed from a material from the imide family and particles formed from another family such as high-end imides can be used to form the reinforcing underlayment.

In an alternative embodiment, a coating system includes a plurality of coating applicators, at least one container having a wet bonding material, at least one container having substantially dry particles, wherein the containers are connected to the coating applicators. The containers are connected to the coating applicators with at least one coating line or tube, which transports the materials from the containers to the coating applicators. It should be appreciated that the coating applicators may be spray guns, electrostatic spray guns, powder spray guns or any other suitable applicators. The coating applicators are positioned adjacent to the surface or surfaces being coated on the substrate. Additionally, the coating applicators may apply the coatings at the same rate or at different rates.

In one example, multiple coating applicators such as two electrostatic spray guns or powder spray guns, apply an epoxy-based material to a surface of a substrate. The epoxy is made up of relatively dry particles which are applied using electrostatic attraction to the surface. While the epoxy is in place, a thin layer of a wet bonding material is fog-sprayed or applied to the epoxy particles to slightly dampen the surface of the particles. Then, a powder spray of aluminum oxide, bronze, ceramic, glass or any other suitable material is applied to the bonding material on the particles. The layers are then heated or cured at one time. Subsequently, a final coating such as a wet or dry coating may be applied to the cured layers as a final coating or topcoat.

In another embodiment, one or more additional bonding material layers are applied to the first or primary bonding material layer applied to the surface of the substrate to meet specific design specifications or coating requirements of a manufacturer. The bonding material layers may be the same or different bonding materials and are applied to the first bonding material layer until a predetermined thickness is achieved. The uniform dry particles may be applied to any one of the reinforcing material layers on the surface of the substrate. Additionally, different materials may be added to the bonding material layer or layers, based on specific design specifications.

In a further embodiment, the coated substrate is cured using induction heating. In this embodiment, induction sensitive particles such as metal particles are applied to the wet bonding material on the surface of a substrate. The metal particles are rearranged in the wet bonding material using a magnet and induction waves, which are reverse magnetic fields, are then directed at the coated substrate to induce heat in the wet bonding material. The heat induced in the wet bonding material cures the wet bonding material. In another embodiment, an induction heat device is used to raise the temperature of the substrate and thereby cures the wet bonding material layer.

In an alternative embodiment, a coating or coatings are applied to an electrosurgical device such as an electrosurgical blade or knife. In one embodiment, the electrosurgical device includes an electrode including a conductive substrate or conductive material where at least a portion of the electrode is encapsulated in a substantially electrically insulative material such as plastic, a handle connected to one end of the electrode and electrical conductors which are attached inside the handle to conduct electricity from an electrical source and deliver or transfer the electricity to the electrode. In one embodiment, the electrode conducts electricity to generate heat and cut, coagulate and/or cauterize tissue during a surgical procedure. In one embodiment, an anti-bacterial or anti-microbial and non-stick coating is applied uniformly and evenly to the surface or surfaces of the electrode to completely coat the exposed distal end or portion and the plastic encapsulated portion of the electrosurgical device. This prevents the growth of bacteria and other harmful organisms on the exposed distal end of the device and underneath and on the plastic coated portion of the electrosurgical device. In one embodiment, anti-microbial or anti-bacterial particles are initially interspersed in the non-stick coating and then the coating mixture is applied evenly to the surface of the substrate. In this embodiment, the non-stick coating is any suitable non-stick coating including at least one of the following materials: silicone, polytetrafluoro ethelyne, fluoropolymers and a combination of fluorosilicones. The non-stick coating prevents charred tissue (i.e., eschar) from building up on the surface or surfaces of the electrosurgical device. In one embodiment, the anti-microbial, non-stick coating is applied to a desired thickness on the surfaces of the electrosurgical device.

In another embodiment, a plurality of coatings are applied to the surface of the electrode of the electrosurgical device. In this embodiment, the surfaces of the electrode are initially roughened to promote the adhering of the coatings to the surface of the substrate. An even layer of primer or other base coating is applied to the roughened surfaces of the electrode. An evenly and uniformly distributed layer of anti-microbial particles is then applied to the primer or base material layer on the surfaces of the substrate. As described above, the anti-microbial particles are preferably applied such that the particles completely and uniformly cover (at a coverage of approximately 10% to 100% depending on the end-use engineering and environmental requirements) the surfaces of the electrode. Once the particles are applied to the electrode, an evenly distributed layer of top coating is applied onto the anti-microbial particle layer. In one embodiment, the top coating is partially applied to the anti-microbial particle layer so that some or all of the particles protrude from and are exposed at the surfaces of the electrode. In another embodiment, the top coating completely coats or covers the anti-microbial particle layer. A portion of the top coating is then sanded or buffed away so that some or all of the silver particles are exposed at the working surfaces of the electrode. In a further embodiment, a light dusting of the silver particles is applied to the primer layer on the surface of the electrode without a top coating. In one embodiment, the top coating is a non-stick coating such as one of the non-stick or release coatings described above. The non-stick coating prevents the build up of eschar on the surfaces of the electrode during a surgical procedure.

In another embodiment, a base material such as a primer or primer coating is applied to the surfaces of the electrode followed by a layer of anti-microbial particles. Then, another layer of the same base material is applied to the anti-microbial particles followed by a layer of anti-microbial particles. The layers of coatings and anti-microbial particles are repeated until the thickness of the electrode including the coating layers achieves a desired thickness. It should be appreciated that the base material layers or material layers may include the same material or coatings or a plurality of different materials or coatings.

Once the coatings are applied to the surfaces of the electrode, the coatings are cured in a suitable oven or furnace, or by using a suitable curing method or process. The curing process hardens the coatings and promotes the adherence of the coatings to the electrode. The coated electrode, therefore, minimizes the build up of eschar on the surfaces of the coated substrate and also tends to kill bacteria or other harmful organisms that contact the surface of the electrode during and after the surgical procedure. Additionally, the anti-microbial coated electrode can be used multiple times in different surgical procedures without requiring sterilization (even though sterilization is preferred) because the anti-microbial particles kill the bacteria and other harmful organisms which contact the surfaces of the electrode. This is especially important in second and third world countries where proper sterilization may be performed infrequently or not at all. The coated electrosurgical device therefore minimizes the chance of infections or other complications in the body after the surgical procedure is complete.

In one embodiment, the anti-microbial particles include silver or silver ceramic particles. The silver or silver ceramic particles kill any bacteria or harmful organisms which come in contact with the silver or silver ceramic particles in the coating and also increase the electrical conductivity of the substrate. The silver or silver ceramic particles in the coating enable the electrosurgical device to reach a desired temperature much quicker than conventional electrosurgical devices because the silver or silver ceramic particles increase the conductivity of the coated electrode surface. As a result, electricity or heat is efficiently conducted or transferred to the electrode surface. In one aspect of this embodiment, the amount and density of silver or silver ceramic particles applied to the surfaces of the electrode is increased or decreased based on the desired electrical and heat conductivity of the electrosurgical device. The electrical and thermal conductivity increases when more silver or silver ceramic particles are included in the coating and it decreases when less silver or silver ceramic particles are included in the coating. Additionally, the density of the silver or silver ceramic particles applied to the surface of the electrode may be adjusted to increase or decrease the electrical conductivity. Increasing the density of the silver or silver ceramic particles increases the electrical and thermal conductivity of the electrode and decreasing the density decreases the electrical and thermal conductivity. When the electrical conductivity of the electrode is increased, the temperature of the electrode increases. This enables the coating mixture to be adjusted and the coating applied to specific portions or edges of the electrode to increase the temperature of the electrode at those locations.

It is therefore an advantage of the present invention to provide a reinforcing underlayment and a method for manufacturing the reinforcing underlayment that increases the desired final system characteristics of a substrate.

Another advantage of the present invention to provide a reinforcing underlayment and a method for manufacturing the reinforcing underlayment that enhances, improves or changes the inherent characteristics of a substrate or surface.

A further advantage of the present invention is to provide a method for manufacturing for a coating underlayment which enables the underlayment to be applied to a substrate as a single, even and substantially uniform layer of particles.

Another advantage of the present invention is to provide a method of manufacturing a coating underlayment that employs substantially uniform particles to form the underlayment layer on a substrate.

A further advantage of the present invention is to provide a method of manufacturing a coating underlayment that employs different sized particles and particles of different chemistries and characteristics to form the underlayment layer on a substrate.

Another advantage of the present invention is to provide a coating underlayment and method of making the coating underlayment that can be used on a wide variety of temperature sensitive substrates and products.

A further advantage of the present invention is to provide a coating underlayment apparatus and method which significantly reduces capital equipment costs, operation costs and process complications.

Another advantage of the present invention is to provide a anti-microbial, non-stick coating to the surface of an electrosurgical device to prevent the build up of tissue on the device and prevent bacteria and other harmful organisms from residing on the surfaces of the device.

A further advantage of the present invention is to provide a anti-microbial, non-stick coating to the surface of an electrosurgical device to enable the device to be used multiple times in different surgical procedures.

Additional features and advantages of the present invention are described in and will be apparent from, the following Detailed Description of the Invention and the Figures.

BRIEF DESCRIPTION OF THE FIGURES

FIG. 4 is a flowchart illustrating one embodiment of the coating method of the present invention.

FIG. 6A is an enlarged fragmentary side view of a coated substrate of another embodiment of the present invention illustrating a coated substrate including a coating layer applied to the bonding material layer.

FIG. 6B is an enlarged fragmentary cross-sectional view of the coated substrate of FIG. 6A taken substantially along the line 6B-6B.

FIG. 6C is a top view of the embodiment of FIG. 6A.

FIG. 7C is an enlarged fragmentary side view of a coated substrate of another embodiment of the present invention illustrating a coated substrate including multiple underlayment layers having spherical particles introduced into each individual layer.

FIG. 7D is an enlarged fragmentary cross-sectional view of the coated substrate of FIG. 7C taken substantially along the line 7D-7D.

FIG. 12A is a cross-section view of the embodiment of FIG. 11 taken generally along the line 12A-12A.

FIG. 12B is a cross-section view of the embodiment of FIG. 11 taken generally along the line 12B-12B.

DETAILED DESCRIPTION OF THE INVENTION

Reinforcing Underlayment

Figure 1A:
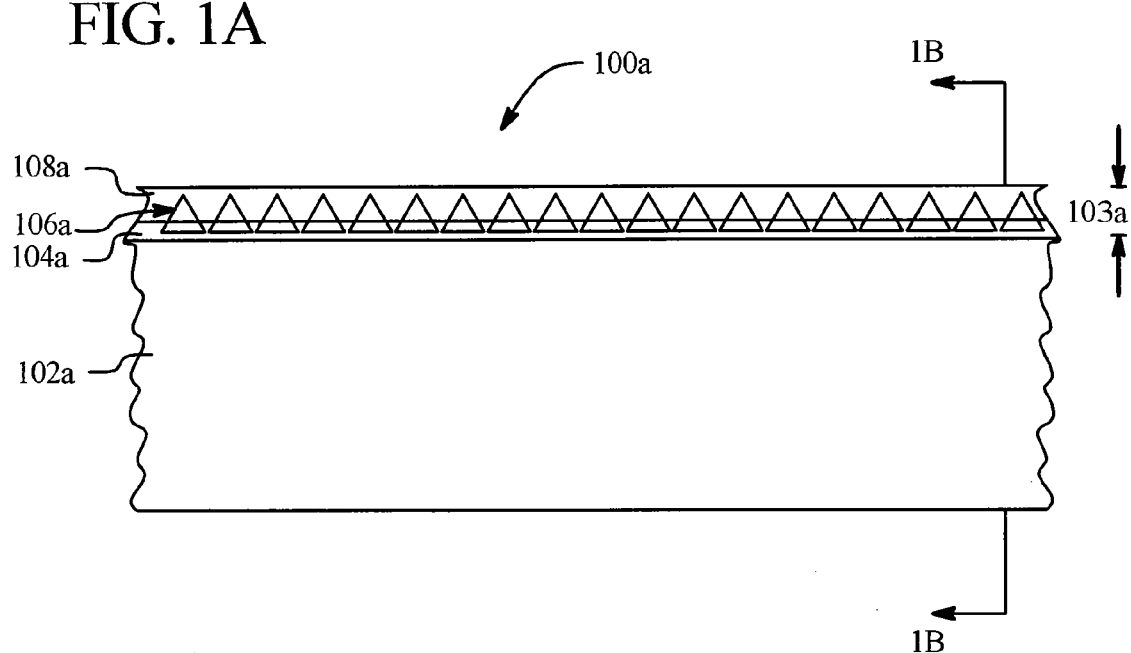
FIG. 1A is an enlarged fragmentary side view of a coated substrate of one embodiment of the present invention.
Figure 1B:
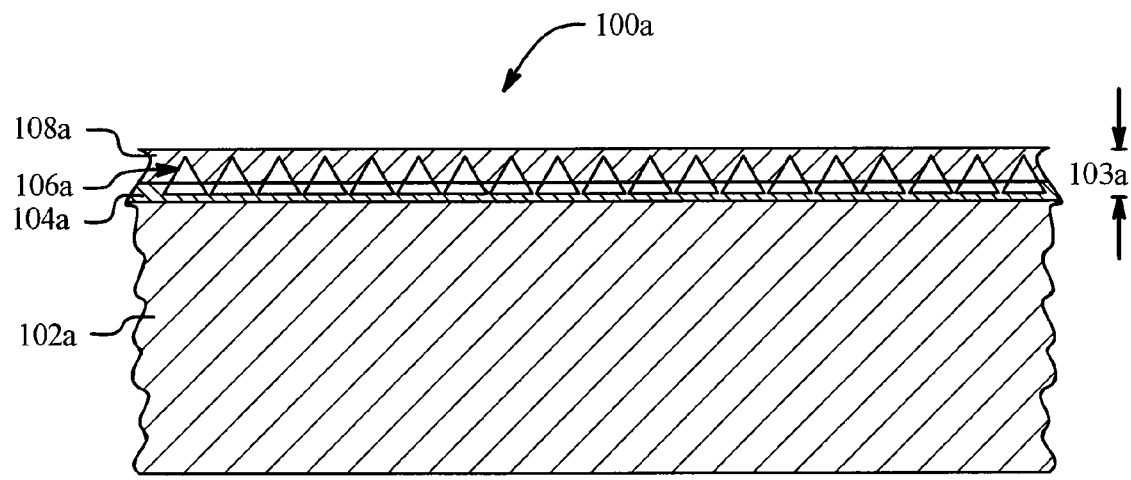
FIG. 1B is an enlarged fragmentary cross-sectional view of the coated substrate of FIG. 1A taken substantially along the line 1B-1B.

Referring now to FIGS. 1A and 1B, one embodiment of a product including the coating reinforcing underlayment of the present invention is illustrated where a coating such as a topcoat material is applied to an underlayment. In this embodiment, a reinforcing underlayment 103a includes a wet bonding material layer 104a and a single layer of substantially uniform dry particles 106a which are applied substantially evenly to the bonding material layer on a surface of the substrate or product as shown in FIG. 1A. The reinforcing underlayment of the present invention is employed or used to facilitate the adherence of a coating to at least a portion of the surface of the substrate. The substrate 102a generally may be any suitable type of substrate such as a metal, wood, plastic, glass or other suitable material.

A layer of wet bonding material 104a such as a separate layer of an adhesion promoter or other suitable material or mixture of materials, is applied to the surface of the substrate to be coated to promote the adhesion of subsequent layers to the substrate. In one embodiment, the wet bonding material is a ultraviolet light cure resin. In another embodiment, the wet bonding material includes an electron beam cure resin. It should be appreciated that the bonding material layer 104a may be any suitable wet bonding material with or without one or more additives which change or enhance one or more characteristics of the wet bonding material. In one embodiment, the wet bonding material layer or film thickness ranges from five microns to one hundred fifty microns or larger. The wet bonding material layer may therefore be a thick layer where the uniform particles sink into and are completely covered by the wet bonding material layer. In another embodiment, the wet bonding material layer is a substantially thin layer on the surface of the substrate and only a small portion of the particles adhere to the thin, wet bonding material layer. Furthermore, the reinforcing underlayment 103a includes a single layer of substantially uniform dry particles 106a, which are evenly distributed or applied to the wet bonding material layer 104a. After the dry particles 106a are applied to the wet bonding material layer and the wet bonding layer is cured, a reinforcing material topcoat layer or reinforcing topcoat coating 108a is applied to the reinforcing underlayment 103a. The reinforcing topcoat coating 108a may be any suitable type of material or coating applied to substrates such as a topcoat, paint, a non-stick coating, a corrosion protective coating or other suitable materials or coatings that can be mixtures of solid particles and liquid materials. It should also be appreciated that the reinforcing topcoat coating may be any suitable topcoat such as ultraviolet light cure resins or electron beam cure resins. One or more reinforcing material layers or reinforcing coatings may be applied to the layer of dry particles based on the design specifications and the desires of the manufacturer. The reinforcing material layers or coatings may be the same materials or coatings, or different materials or coatings. In one embodiment, the final topcoat reinforcing material layer(s) is/are applied to the dry particle layer until a predetermined or desired thickness is achieved. In another embodiment, the reinforcing material layers and/or coatings are applied until the layers and the substrate are a predetermined or desired total or overall thickness.

After the coatings have been applied to the substrate, the resultant structure of the underlayment 103a includes the dry particles or granules introduced into the wet bonding material layer where the wet bonding material layer adheres to various types of surfaces of a substrate such as round or flat surfaces. In a curing process, the dry particles 106a remain in place completely covering the wet bonding layer 104a while the wet bonding material layer 104a passes through phases until the dry particles and the bonding material layer are fused together as the liquid layer is cured. It should be appreciated that the bonding material layer 104a and uniform dry particles 106a may be partially cured or completely cured depending on whether single or multiple bonding material and dry particle layers are applied to the surface of the substrate.

Figure 1C:
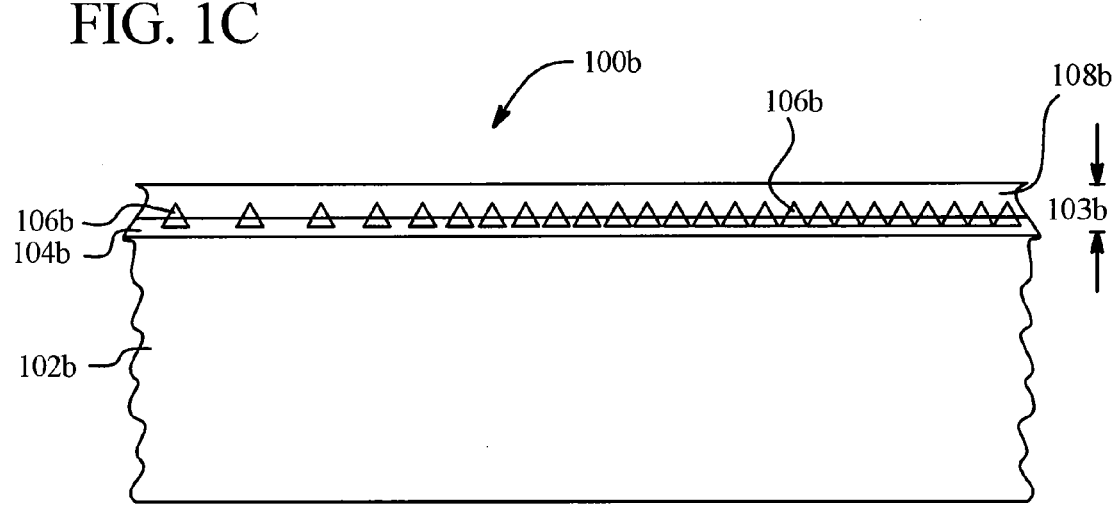
FIG. 1C is an enlarged fragmentary side view of a coated substrate of another embodiment of the present invention including angular particles distributed on the surface of the substrate with different densities.
Figure 1D:
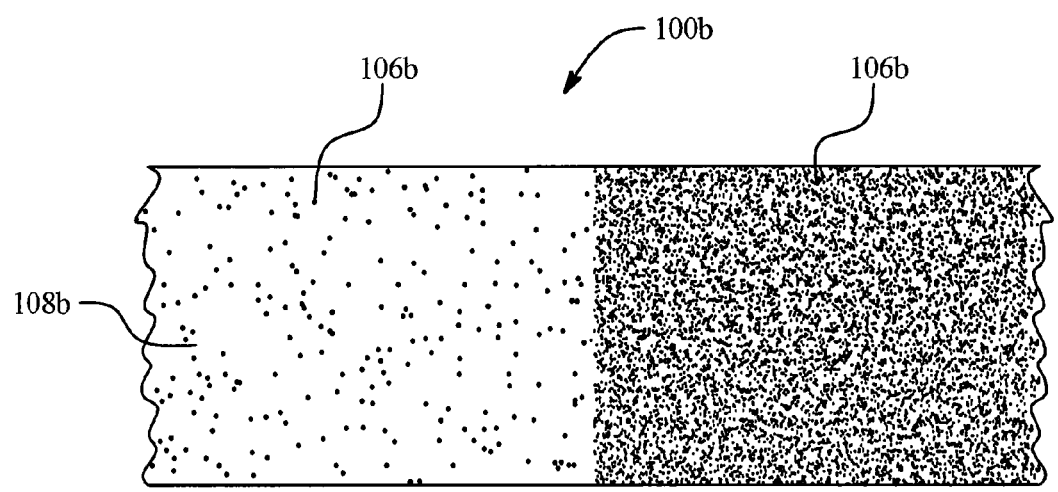
FIG. 1D is a top view of the embodiment of FIG. 1C.

Referring to FIGS. 1C and 1D, another embodiment of the present invention is illustrated where the coated substrate includes uniform size angular particles distributed with varying densities on the surface of the substrate. This type of distribution may be employed on products such as cooking equipment where greater abrasion resistance is desired in specific areas. For example, the denser distribution of particles is applied to the more abrasive areas to minimize the effects of the abrasion on the surface. In FIG. 1C, a bonding material layer 104b is applied to the surface of the substrate 102b. The angular particles 106b are then applied with different distributions or varied densities on the surface. The particles are applied to a suitable thickness such as the thickness 103b. A topcoat or final coating 108b is applied if desired, such as PTFE. In one embodiment, the topcoat is a suitable solvent which is applied over the particles after the particles are applied to the wet bonding material. The capillary action of the solvents draws some of the wet bonding material up over the particles as the solvent evaporates to strengthen the bond of the particles to the wet material bonding layer. The final coated substrate 100b therefore includes different densities of uniform particles as shown in FIG. 1D.

Figure 1E:
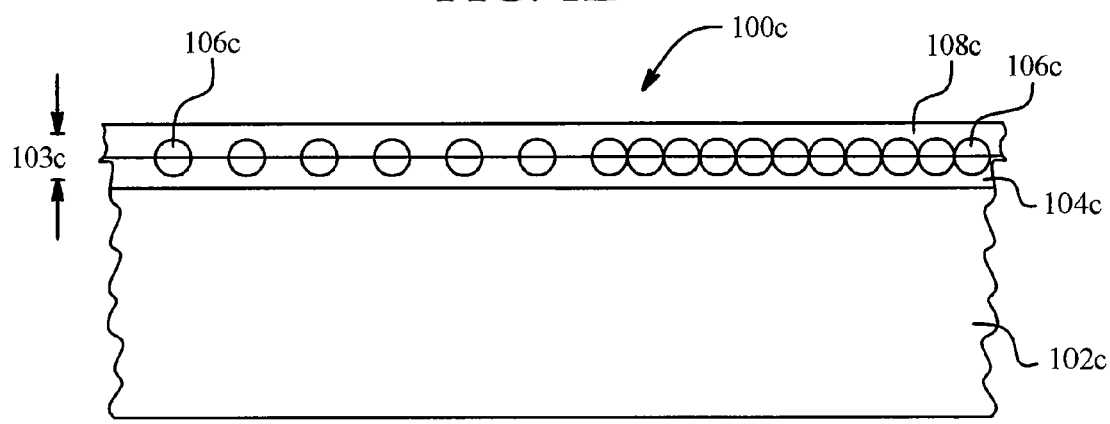
FIG. 1E is an enlarged fragmentary side view of a coated substrate of another embodiment of the present invention including spherical particles distributed on the surface of the substrate with different densities.
Figure 1F:
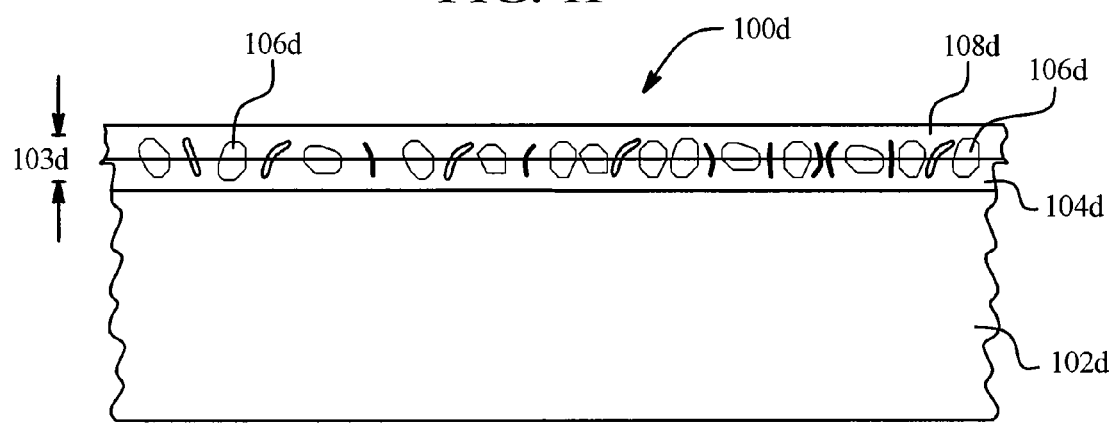
FIG. 1F is an enlarged fragmentary side view of a coated substrate of another embodiment of the present invention including flake-shaped particles distributed on the surface of the substrate with different densities.
Figure 1G:
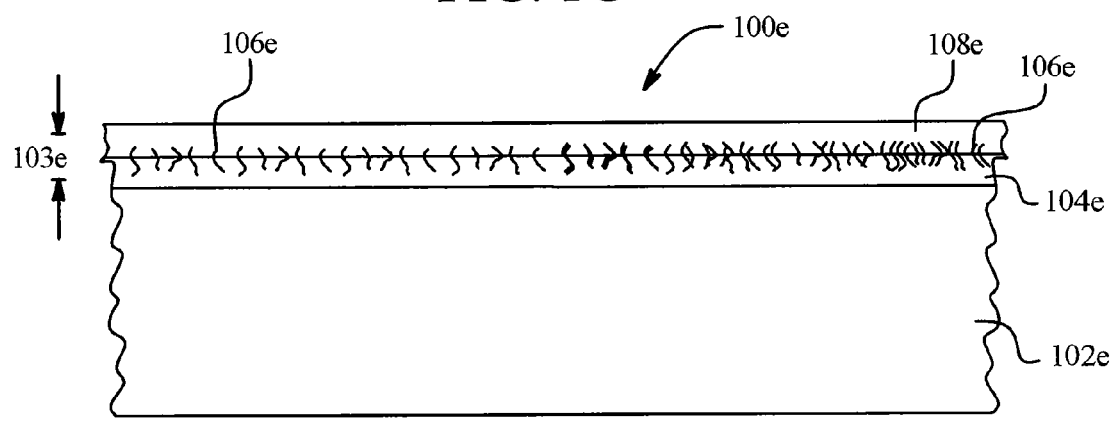
FIG. 1G is an enlarged fragmentary side view of a coated substrate of another embodiment of the present invention including fiber particles distributed on the surface of the substrate with different densities.
Figure 1H:
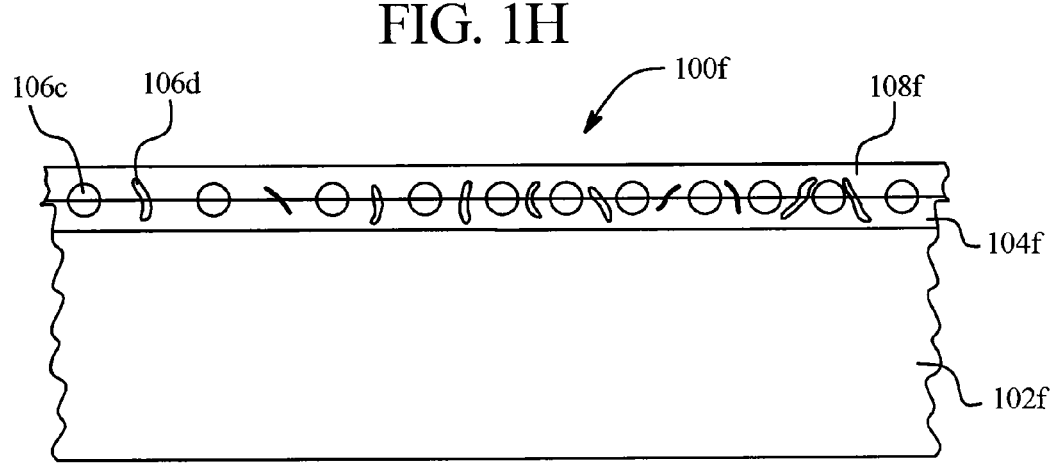
FIG. 1H is an enlarged fragmentary side view of a coated substrate of another embodiment of the present invention including spherical and flake-shaped particles distributed on the surface of the substrate with different densities.
Figure 1I:
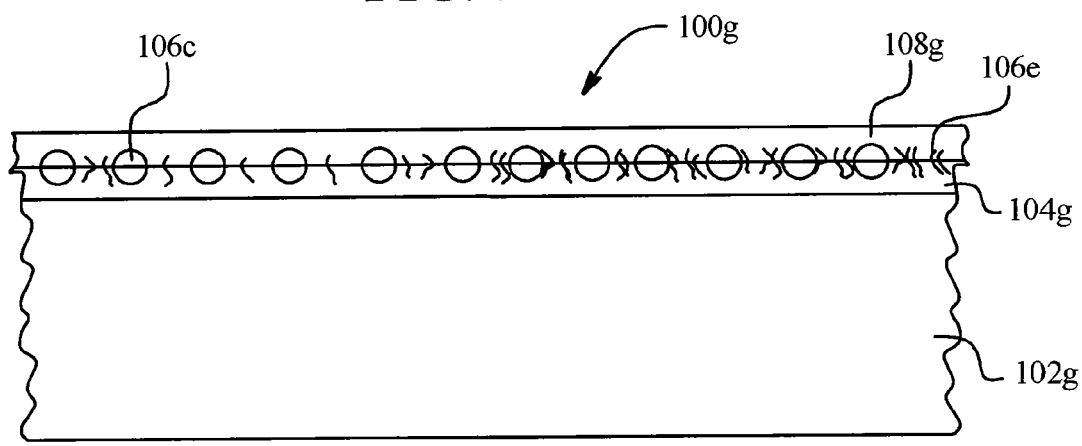
FIG. 1I is an enlarged fragmentary side view of a coated substrate of another embodiment of the present invention including spherical and fiber particles distributed on the surface of the substrate with different densities.
Figure 1J:
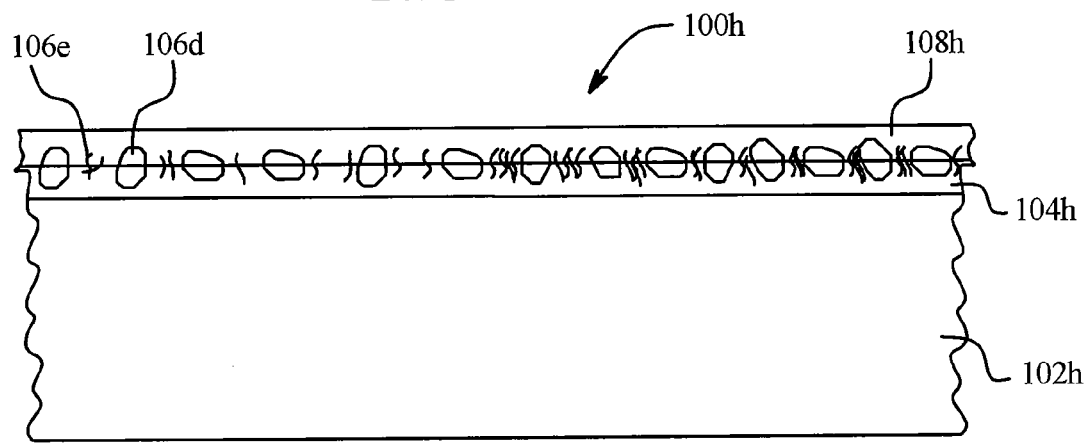
FIG. 1J is an enlarged fragmentary side view of a coated substrate of another embodiment of the present invention including fiber and flake-shaped particles distributed on the surface of the substrate with different densities.

Referring to FIGS. 1E to 1J, different types of particles and different combinations of particles may be applied to the wet bonding material layer on the surface of the substrate. In FIG. 1E, different densities of spherical particles 106c are applied to the wet bonding material layer. In FIG. 1F, different densities of flake-shaped particles 106d are applied to the wet bonding material layer. In FIG. 1G, different densities of fiber particles 106e are applied to the wet bonding material layer. In FIG. 1H, different densities of a combination of spherical particles 106c and flake-shaped particles 106d are applied to the wet bonding material layer. In FIG. 1I, different densities of a combination of spherical particles 106c and fiber particles 106e are applied to the wet bonding material layer. In FIG. 1J, different densities of a combination of flake-shaped particles 106d and fiber particles 106e are applied to the wet bonding material layer. It should be appreciated that any suitable combinations of the above particles may be applied to the wet bonding material layer depending on the end-use requirements and specifications.

Figure 2A:
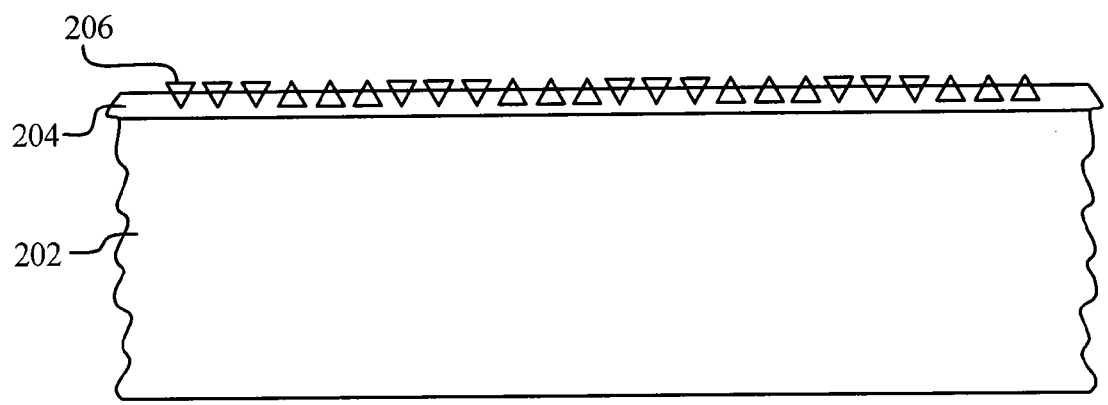
FIG. 2A is an enlarged fragmentary side view of a coated substrate of a another embodiment of the present invention illustrating angular particles applied to the bonding material layer on the surface of a substrate.
Figure 3A:
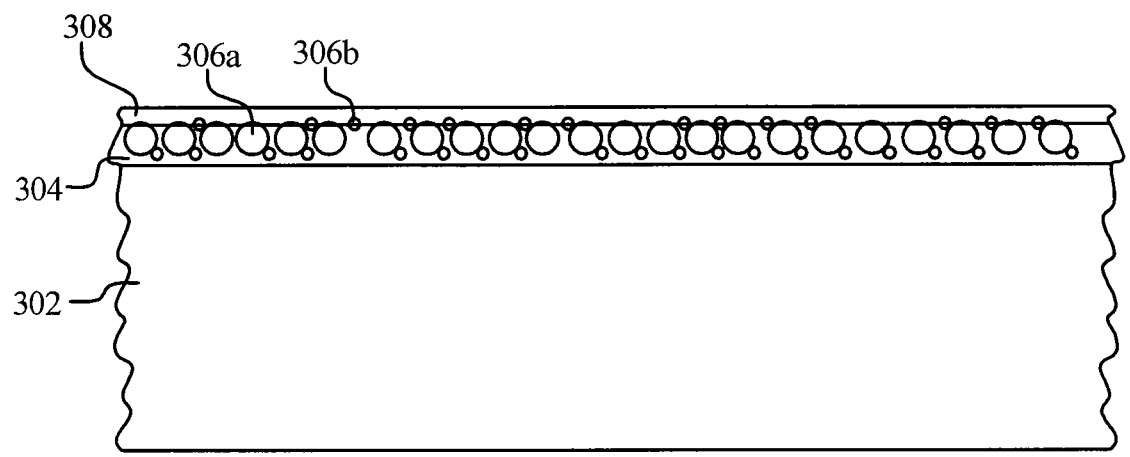
FIG. 3A is an enlarged fragmentary side view of a coated substrate of a another embodiment of the present invention illustrating different sized particles applied to the bonding material layer on the surface of a substrate.
Figure 3B:
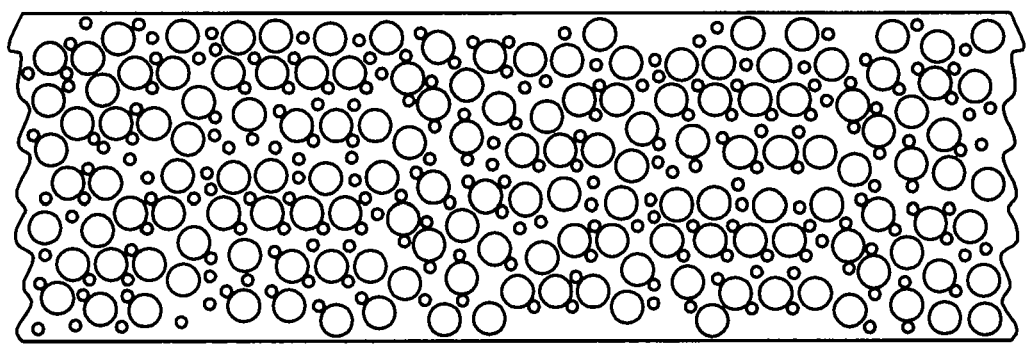
FIG. 3B is a top view of the embodiment of FIG. 3A.

The coating underlayment is primarily composed of substantially uniform dry particles, which form a single substantially uniform and substantially even layer on the surface of the substrate or product. In one embodiment where abrasive resistant surfaces are desired, the substantially uniform dry particles may be any suitable size or shape as desired by the manufacturer such as flat-shaped, flake-shaped, angular-shaped, cylindrical-shaped, oblong-shaped and leaf-shaped particles. Specifically, the substantially uniform dry particles are substantially the same in size and shape for several reasons, including so that the coating area or area of adhesion is maximized on the surface of the substrate. In one embodiment shown in FIG. 2A, angular particles 206 such as triangular shaped particles are used to create a rough surface on a substrate by applying the angular particles to the bonding material layer 204 on the surface of the substrate 202. In another embodiment, softer, less abrasive surfaces are created by using shaped particles such as spherical shaped particles. In a further example described in more detail below, combinations of different shaped particles are used on a surface of a substrate as shown in FIGS. 3A and 3B. Thus, uniformly sized or shaped particles or different sized or shaped particles may be applied to a surface of a substrate.

Figure 2B:
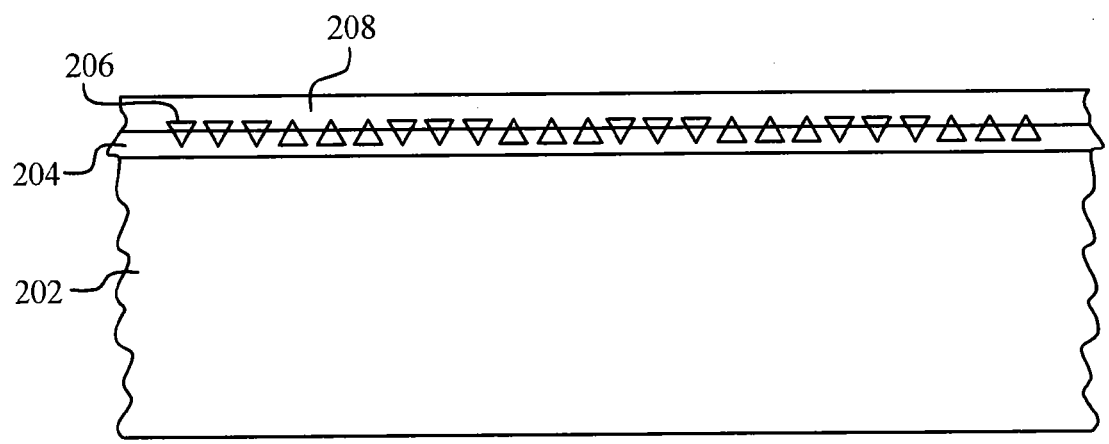
FIG. 2B is an enlarged fragmentary side view of the embodiment of FIG. 2A where an abrasion resistant coating is applied to the angular particle layer on the surface of the substrate.

As indicated above, in one preferred embodiment, the wet bonding material layer and the substantially uniform dry particle layer are applied to the surface of the substrate until a desired thickness is achieved. In one presently preferred embodiment, the desired thickness is approximately 5 μm to 100 μm. Other suitable thickness ranges may be used as desired by the manufacturer. In FIG. 2B, an abrasion resistant topcoat or final coating 208 is applied to the angular particles 206. The abrasion resistant coating further enhances the abrasion resistant characteristics of the surface of the substrate.

In another embodiment, the substantially uniform dry particle layer is composed of substantially spherical particles, which creates a softer, less abrasive surface on the substrate. It should be appreciated that the particles may be spherical particles, substantially flat flakes, fibers or any suitable shape or combination of shapes as described above, which maximizes the surface area of the uniform particle layer. Additionally, the size of the dry particles may be changed as desired to accommodate different technical and coating requirements or specifications. In one embodiment, the dry particles include at least one relatively large particle and at least one relatively small particle. In another embodiment, the dry particles range in size such as from a sub-micron to approximately 125-150 microns.

The density of the uniform particles on the wet bonding material layer on the surface of a substrate may be changed or enhanced to strengthen the bond of the particles in the layer. In one embodiment, the particles are applied to the wet bonding material layer and then the part is vibrated to settle the particles into the wet bonding material layer. In another embodiment, a wet bonding material layer and a layer of substantially uniform particles are applied to a surface of a substrate such as a round part having an internal bore. The part is rotated, which causes the particles to densify or pack together in the wet bonding material due to the centrifugal force of the spinning part.

Figure 3C:
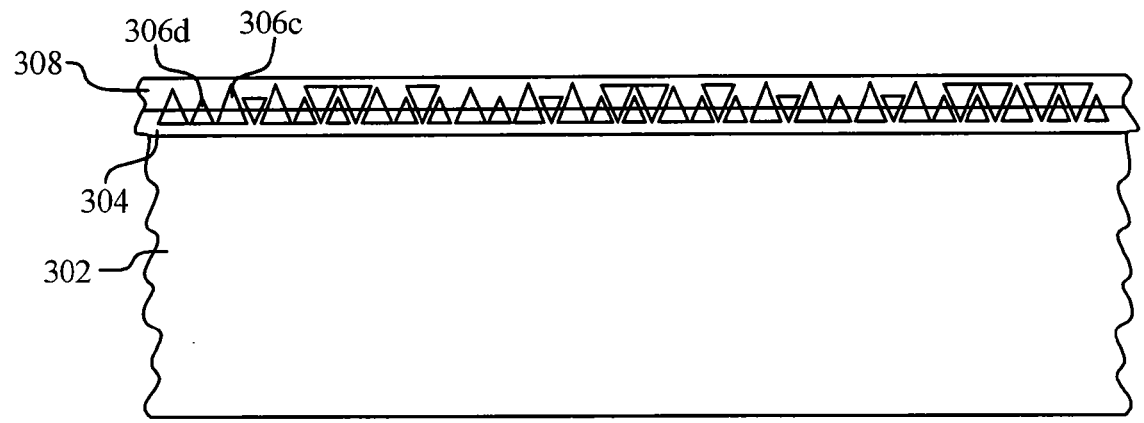
FIG. 3C is an enlarged fragmentary side view of a coated substrate of a further embodiment of the present invention illustrating different sized particles applied to the bonding material layer on the surface of a substrate.
Figure 3D:
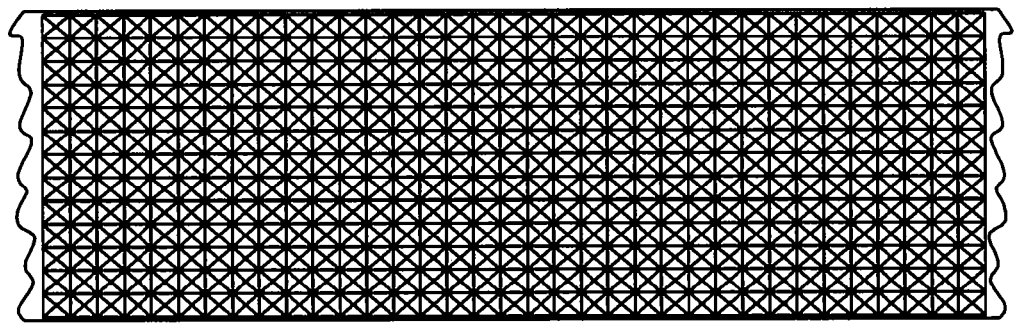
FIG. 3D is a top view of the embodiment of FIG. 3C.

Referring to FIGS. 3A and 3B, the uniform particle layer includes different sized spherical particles 306a and 306b applied to the bonding material layer 304 on the surface of the substrate 302. In one example, the smaller sized particles 306b are softer particles and the larger sized particles 306a are harder particles such that the soft particles provide lower friction and the hard particles enhance the abrasion resistance of the surface as described in more detail below. Another example, hard abrasion resistant larger size particles and smaller electrically conductive particles are applied to create an abrasion resistant and electrically conductive reinforcement underlayer. A topcoat or final coating 308 of a suitable material is applied to the uniform particle layer. In FIGS. 3C and 3D, another aspect of this embodiment is illustrated where different sized angular particles 306c and 306d are applied to the wet bonding material layer 304 on the surface of the substrate 302. It should be appreciated that any sizes and shaped particles may be applied to the surface of the substrate.

Coating Underlayment Method

Referring to FIG. 4, one embodiment of the method of applying the coating underlayment to form a coated substrate is illustrated in the flow diagram. In the method illustrated in FIG. 4, one or more surfaces to be coated on a substrate are cleaned using a suitable cleaner as indicated in block 400. The cleaner removes a substantial portion of or all of the impurities that may be on the surface of the substrate which may inhibit the adhesion of one or more of the layers to the substrate. The surfaces to be coated may be cleaned manually or mechanically in an automated process. The substrate may be cleaned using any suitable cleaning process such as grit blasting or sandblasting, which slightly roughens and cleans the surface or surfaces of a substrate. Additionally, the substrate may be pre-cleaned in a clean room or similar manufacturing area where the step described in block 400 is not necessary.

After the substrate is cleaned or is clean, a layer of a substantially wet bonding material is applied to the substrate as indicated by block 402. The bonding material provides a wet or moist surface for the subsequent substantially uniform dry particle layer to adhere to. The wet bonding material may be any suitable bonding material, which meets the specific design specifications of the particular product or substrate. In this embodiment, it is important that the bonding material remain wet prior to the application of the uniform dry particle layer so that the dry particles stick to or adhere to the wet bonding material. As described in block 404, in this embodiment, a single layer of substantially uniform dry particles are applied or sprayed onto the wet bonding material layer until the wet bonding material layer is completely coated with the dry uniform particles and a desired thickness is achieved. The thickness of the coatings or coating layers is dependent on the specifications for the particular product, the amount of bonding material applied and the size and shape of the dry particles.

In one embodiment, the substantially uniform dry particles are sprayed or applied onto the wet bonding material as a single substantially uniform and substantially even layer which adheres to the sticky or wet surface of the bonding material. In another embodiment, the substrate is electrically grounded using a suitable grounding method. Grounding the substrate thereby grounds the wet bonding material layer, which is formulated to include solvents and/or liquids that conduct electrical energy. The substantially uniform dry particle layer has or will have an opposite electrical charge to that of the bonding material layer and therefore is electrically or electrostatically attracted to the wet bonding material layer as the dry particles are applied to that layer. In a further embodiment, an applicator such as a sifter is used to uniformly apply the uniform particles to the wet bonding material layer. The sifter is similar to a conventional flour sifter or a drum sifter and is used in certain applications depending on the required application of the uniform particles.

Figure 5A:
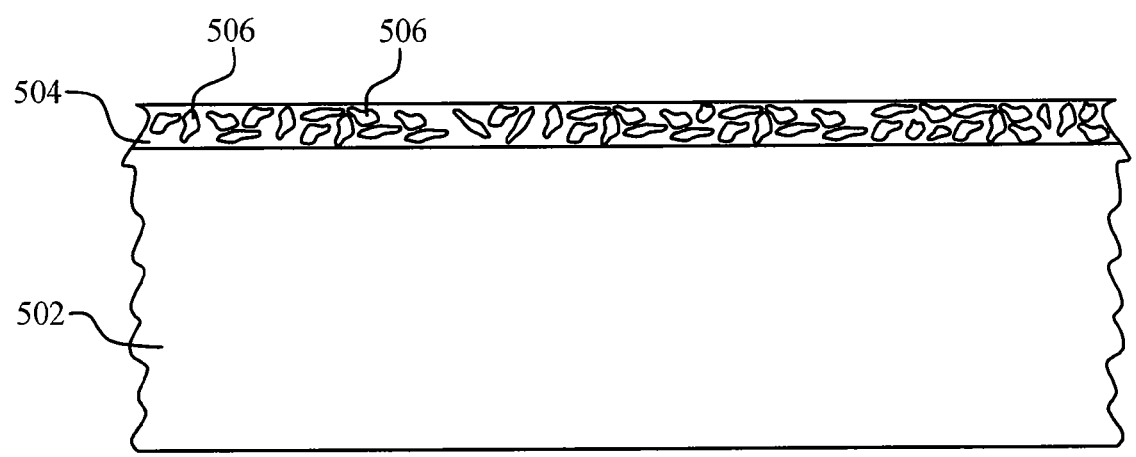
FIG. 5A is an enlarged fragmentary side view of a coated substrate of a further embodiment of the present invention illustrating flake-shaped particles applied to the bonding material layer on the surface of a substrate.

In another embodiment illustrated in FIG. 5A, an electrically conductive liquid bonding material layer is applied to the surface of the substrate to enhance the attraction of the dry particles, which may be material flakes (as shown in FIG. 5), ceramic or plastic particles and also specially treated or untreated particles, such as bronze, brass, zinc, copper, steel, stainless steel, aluminum, graphite, titanium, molybdenum disulfide, molybdenum, talc, lead, antimony, tin, silver, titanium and nickel or any other suitable metals, alloys, ceramics or plastics. The oppositely charged or tribo-charged (i.e., friction charged) electrical attraction of the dry particles or flakes 506 to the wet bonding material layer 504 promotes the adhesion and uniformity of coverage of the dry particles to the bonding material layer. The metal particles can be propelled toward the wet surface with air or gasses that have been ionized or treated to momentarily electrically charge the metal conductive particles with the opposite charge of the wet surface of the substrate. The result is a dense, substantially uniform and evenly distributed particle layer or underlayment layer on the surface of the substrate 502.

In another embodiment, a liquid bonding material layer such as an epoxy, which is thermally cured, is applied to the surface of the substrate. The metal particles are then introduced using a dry powder spray mechanism. In one aspect of this embodiment, the metal particles are passed through a heating chamber or flame device, such as on a metal spray gun. The metal particles pass through an oxyacetylene flame raising the temperature of the particles as the particles are propelled towards the pre-applied wet bonding layer. Introduction of heat into the particles allows the wet bonding material layer to start curing or semi-curing. The curing or semi-curing occurs because the heat introduced into the coating starts to harden the bonding material layer after the particles have been immersed in the material layer due to the velocity and force of the particles propelled at the wet bonding material layer.

In a further embodiment, several different metals are applied to a bonding material layer on a surface of a substrate. In one example, bronze particles having a size of 35-microns and lead particles having a size of 5-microns are sequentially applied to a bonding material layer on a surface of a substrate. In another example, metals and non-metals are combined to form the underlayment. For instance, bronze particles and pre-cured imide-amide particles can be applied to the bonding material layer. Additionally, particles formed from a material from the imide family and particles formed from another family such as high-end imides can be applied to the bonding material layer. This combination allows the bronze to dissipate or absorb surface heat and conduct heat away from the surface of the substrate. The engineering plastic materials described above can be used instead of the bronze particles if much lower friction is desired.

Referring now again to FIG. 4, after the substantially uniform particle layer is applied to the bonding material layer, the layers are cured to strengthen the bond between the uniform dry particle layer and the wet primer layer on the surface of substrate as indicated by block 406. The curing process may be performed by heating the layers at a predetermined temperature or temperatures, air-drying the layers or by utilizing any suitable internal or external curing or cross linking process. In addition, the curing process may use a single or plural package heat cure or air-dry materials, such as polyimide for heat cure applications and acrylics for air-dry applications and two part epoxies for room temperature or U.V. rapid curing. When the substantially uniform dry particle layer has completely adhered or bonded to the bonding material layer, a suitable coating layer is applied to the uniform dry particle layer as indicated in block 408. The coating may be any suitable coating such as a topcoat or final coat material. Examples include corrosive or abrasive resistant coatings, non-stick coatings or low friction coatings and electrically insulative or conductive coatings or combinations thereof.

The substantially uniform dry particle layer maximizes the surface area exposed to the coating applied to that surface of the particles. Increasing the surface area for the application of a coating to that area, enables the coating to develop a very strong mechanical bond to the underlayment layer and ultimately to the substrate. The strong bond between the coating and the underlayment layer promotes the durability and strength of the coating on a product or substrate. Furthermore, the coating underlayment layer also promotes a substantially even and uniform distribution of the coating to the substrate. Optimum adhesion is provided by the first wet bonding layer on the surface to the subsequently applied particles. The second wet coating is formulated to provide optimum adhesion to the particles and provide specific characteristic to the final surface as determined by the use of the final surface. This minimizes the defects or uneven distribution of the coating on the surface of the substrate and promotes the maximum functional values of the coated part. Thus, less parts or products are discarded due to uneven coating or defective coating layers on a substrate or product and the coating provides the maximum functional characteristics with minimal compromises of the functional characteristics of the finished or complete coating.

Uniform Particle Embodiments

The types of particles applied to the surface of a substrate vary based on the specific requirements of a substrate or based on the environment in which the substrate is being used. In one embodiment, dry or powdered carbon particles or whiskers or rods such as carbon fiber particles or whiskers are applied to a substrate to prevent wear of a surface on the substrate and to provide a non-metallic conductive surface. The dry or powdered carbon fibers are substantially uniform fibers applied to a wet bonding material layer such as a primer on a surface of a substrate. In one example, a substrate including carbon fiber particles is used for high temperature commercial knives and cutting blades where static electricity must be dissipated. In another example, a substrate including carbon fiber particles is used for conveyors to transport paper and other static electricity producing materials, such as plastic. In this embodiment, the wear reduction capabilities of a substrate are vastly improved with the carbon fibers, which can be as small as approximately three microns in diameter and approximately 20-30 microns long. When the carbon fibers are dry sprayed onto the bonding material layer, the shorter fibers orient themselves in multiple directions thereby enhancing the wear resistance of the carbon fiber layer (the end of the carbon fiber particles do protrude through the final coating surface). The bonding matrix is designed according to end use or design specifications. The carbon fibers may include a high or low temperature material.

In another embodiment, aramid fibers or engineered plastic particles or fibers are applied to a substrate to strengthen the surface of the substrate. The aramid fibers may be any suitable aramid material such as Kevlar®, which is manufactured and sold by the E.I. du Pont de Nemours Company. The aramid or Kevlar® fibers are applied to the bonding material layer in very much the same manner as the carbon fibers or whiskers. The Kevlar® fibers or materials can be either a pulp, which includes loose, fluffy fibers which is further ground into a fine powder, or can be other suitable forms such as round particles or semi-round particles. The aramid particles provide non-metallic wear resistance and have good bonding ability with both the basecoat and subsequent topcoats. Thus, the applied aramid fibers or materials create a dense layer of aramid or Kevlar® particles on the surface of the substrate, which is then coated with a topcoat or other suitable final coating. However, if a very high temperature non-metallic or non-ceramic, moderate friction (i.e., low abrasion) surface is desired, a topcoat or final coating is not applied to the layer of aramid fibers as in a brake surface or clutch facing, or a specific high temperature topcoat formulation may be applied as an option.

In another embodiment, individual and/or combinations of aramid fibers or particles, which may be any random shape and size, are applied to the surface of the substrate. In this embodiment, the dry aramid particles or fibers are applied to the wet bonding layer, which has been previously applied to the surface of the substrate. Because the aramid fibers have extreme temperature resistance compared to most polymers and organics, the aramid fibers or particles can be topcoated with a very high temperature PTFE or silicone type resin. Therefore, the temperature resistance, non-stick capability and wear resistance of the final coated surface is equivalent to and sometimes greater than the same properties for metal fibers or particles.

In one example, the aramid fibers are used as a clutch facing or in a braking mechanism in a tightly contained space. In this example, an aluminum brake shoe is pre-coated with a wet silicone or high temperature imide-amide material layer, then a layer of aramid fibers or particles, followed by another wet silicone or imide-amide layer, and then a imide-amide particle material layer. In one example application of the present invention, a motorcycle clutch disc is manufactured of aluminum and then, using this method to provide wear resistance, eliminates the steel clutch disc construction and reduce the weight of the clutch assembly by more than fifty percent. The aramid fibers reduce and prevent galling and seizure of counter surfaces because of the aramid fibers extremely high temperature capability and ability to char and ablate at the outer surfaces in the presence of oxygen and high scuffing at relative speeds. Additionally, a thin topcoat of PTFE, graphite or another suitable lubricant film can be applied to the aramid particle layer to assist the break in of the counter surface or surfaces.

In a further embodiment, specially treated, uniform plastic particles are applied to a wet bonding layer as applied to a substrate. The plastic particles are pre-treated PTFE, UHMW and/or polyethylene (PE) or another suitable material and applied to the wet bonding material on the surface of the substrate. The particles are pre-irradiated or processed with an electron beam or other suitable method which causes the particles to be able to sink into the wet bonding material layer, instead of remaining on the top of the wet material bonding layer. Therefore, the plastic particles are strongly bonded to the layer and not easily dislodged from the surface. This process thereby enables the plastic particle layer to last longer.

In another embodiment, dry or powdered anti-microbial particles which reduce and kill bacteria and other microbials are applied to the wet bonding material layer on the surface of a substrate. In one aspect of this embodiment, a final coating or topcoat is not applied to the dry anti-microbial particles or powder layer, which enables the anti-microbial particles to remain at the surface. In another aspect of this embodiment, a thin topcoat or final coating such as polytetrafluorethylene (PTFE) is applied to the anti-microbial particulate layer to perform a release function such as a non-stick coating on the surfaces of cooking equipment. In one example, a counter top such as a kitchen counter, is coated with a two part epoxy followed by a powder coating of anti-microbial material. Then, a thin coating of the epoxy is applied to the anti-microbial particulate layer as a final coating or topcoat. Such a counter may be used in a meat packing plant to kill harmful bacteria on counters where the meat is cut and packaged or the anti-microbial coating may be used on hooks or similar conveying equipment in a meat packing house. The anti-microbial effect of the coatings on the counters can be maintained by repeating the coating process on the counter surfaces periodically as needed. It should be appreciated that any suitable anti-microbial particles or material such as silver, silver-ceramic or silver compounds may be used in the above embodiment.

In a further embodiment, dry or powdered, ultra porous bronze or other porous particles are applied to the wet bonding material layer on the surface of a substrate. The ultra porous bronze particles are "sponge-like" particles that include many openings and voids such that the particles are approximately seventy percent solid compared to over ninety percent solid for other porous bronze materials. The ultra porous bronze particles are infused with the wet bonding material after the bronze particles are deposited on the wet bonding material on a surface of a substrate. The infused or vacuum infused material layer permeates the pores of the bronze particles and bonds to the "mini-tunnels" in the particles. The infused layer adds lubrication and increases the bonding strength of the layers to hold the bronze particles to both the upper and lower coating layers and to the surface of the substrate. Thus, this process "locks" the ultra porous particles into the wet bonding material layer, which prevents the particles from dislodging easily from the wet bonding material layer as they wear.

Figure 5B:
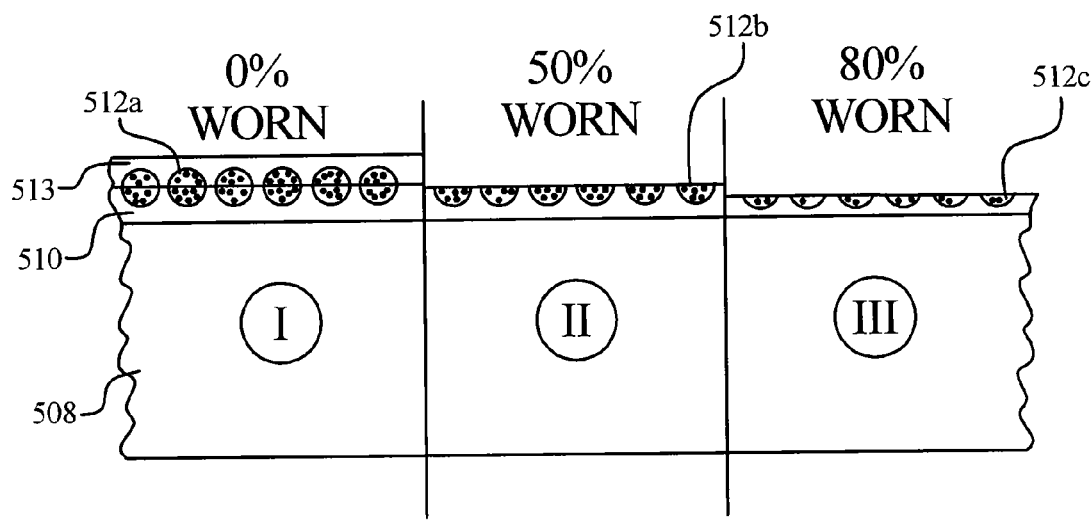
FIG. 5B is an enlarged fragmentary side view of a coated substrate of another embodiment of the present invention illustrating the wear pattern of ultra porous particles applied to the bonding material layer on the surface of a substrate and the attachment of the 80% worn particles due to the anchor pattern of attachment or bonding sites within the porous particles.

FIG. 5B illustrates the secure bond of the ultra porous particles in the bonding material layer. The ultra porous particles are applied to a wet bonding material layer 510 on the surface of a substrate 508 as described above. In addition, a topcoat or final coating 513 of a suitable material such as PTFE is applied to provide further wear resistance. In FIG. 5B, Section I shows that initially one hundred percent of the ultra porous particles are applied to the wet bonding material where there is zero percent wear of the particles. After the topcoat 513 is completely worn away and after the ultra porous particles are worn down to approximately fifty percent of the particles original size as shown in Section II of FIG. 5B, the particles still strongly adhere to wet bonding material 510. As shown in Section III, after some additional time, almost all of the particles remain adhered to the bonding material layer even after approximately eighty percent of the particles has been worn away. In one embodiment, a special topcoat layer including a high solid material which migrates into the pores of the attached bronze particles is applied to the particles, either after the first curing process or as part of the first bonding material layer applied to the surface of the substrate.

In another embodiment, porous metal particles such as the bronze particles described above are impregnated or infused with a material such as PTFE, which lowers the friction of the particles. In one aspect of this embodiment, bronze particles defining or including seventy percent voids (i.e., air) is vacuum impregnated with a suitable material such as PTFE. In another aspect of this embodiment, the bronze particles are soaked with the PTFE and then dried. The latter process leaves partial voids in the particles where the particles are approximately forty percent solids. It should be appreciated that any suitable metal or metal alloy or ceramic particle or particles may be used as the base particles. It should also be appreciated that any suitable low friction material such as PTFE, anerobic polyester and UHMW may be used to fill or partially fill the voids.

Figure 5C:
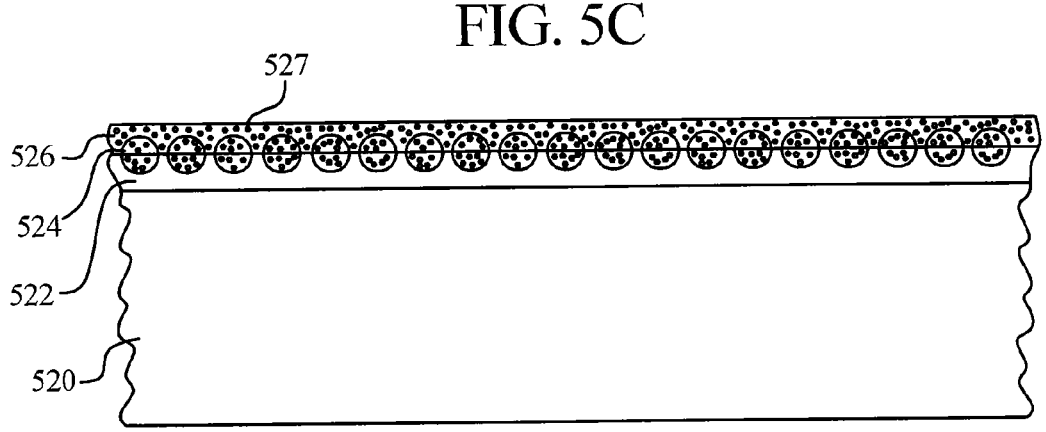
FIG. 5C is an enlarged fragmentary side view of a coated substrate of a further embodiment of the present invention illustrating ultra porous metal or ceramic particles infused with smaller particles and a topcoat containing wear and friction reducing agents, or in another embodiment, anti-microbial materials.
Figure 5D:
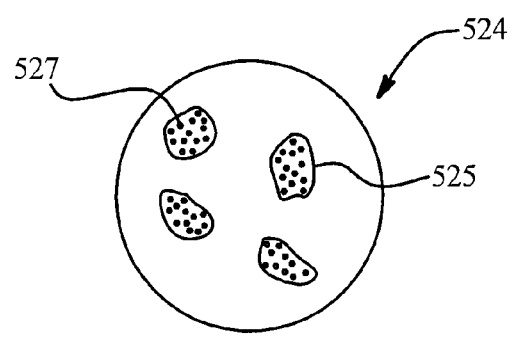
FIG. 5D is an enlarged side view of one of the infused ultra porous metal or ceramic particles of the embodiment of FIG. 5C.

Referring to FIGS. 5C and 5D, in another embodiment, a topcoat material 526 including lubricative particles 527 is applied to the ultra porous bronze particles 524 in the bonding material layer 522 on the surface of a substrate 520. The applied lubricative particles 527 infuse the voided centers 525 of the ultra porous bronze particles to enhance the lubrication associated with the particles and reduce the friction on the particles. The lubricative particles 527 may contain PTFE, graphite or any suitable non-abrasive and/or non-stick material. It should be appreciated that the porous particles may be any suitable porous metal particles such as stainless steel particles, nickel particles, bronze particles, iron particles, titanium particles and suitable particles including a metal and/or metal alloys and also porous ceramic particles which can be infused with conductive particles such as carbon.

Additional Material Layers

In a further embodiment, catalyzed bonding materials such as epoxies and urethanes are used in the present method to enhance the bond strength and lower the curing temperature of the coatings. These bonding agents will be tailored to the desired end use characteristics and also to the temperature capabilities of the substrate. In one example, the flexibility of cure temperature and bond strengths is demonstrated by the bonding of pure bronze particles to a commercial glass-filled plastic engineering component, such as a sliding block contact in an electrical switch gear. The lightweight, rigid engineering glass reinforced plastic conducts no electricity. By adding a layer of bronze, copper, and silver in successive layers, an impact-resistant material is created which contacts a switch gear and makes electrical contact. This may be used, for example, for a safety switch, where the safety switch must be very light weight to respond mechanically quickly in a safety situation. This embodiment may also be employed in a radio wave and electromagnetic environment to absorb radio frequencies (RF) and electromagnetic waves.

In another embodiment, acid or chemical resistance is increased by applying a protective, non-metallic, non-plastic material such as dry ceramic, glass, mica flakes and/or mica particles to the wet bonding material layer. The dry ceramic or mica flakes and/or particles create a barrier or a substantial barrier to an acid or other chemical. The non-metallic, non-plastic material may be any suitable materials such as ceramics, glass, modified mica, mica, boron nitride, silica nitride and aluminum oxide. The barrier diverts the acid or chemical by creating a torturous path or a maze-like path which the acid or chemical cannot avoid as it attempts to penetrate the protective coating. Therefore, the acid or chemical is prevented from directly attacking a base material such as a metal, by decreasing the inherent permeability and porosity of a base coating or coatings such as a fluoropolymer based acid resistant coating.

Referring to FIGS. 6A, 6B and 6C a further embodiment of the present invention is illustrated where a coated substrate 600 includes one or more additional wet bonding material layers applied to the primary or first wet bonding material layer based on specific design specification or manufacturer requirements. The bonding material layers are applied to the first bonding material layer prior to applying the layer of substantially uniform dry particles. In one embodiment, the additional or subsequent bonding material layers include different bonding materials. In another embodiment, the layers include the same bonding material, which is applied to the first bonding material layer to a desired thickness, such as a thickness, t. First, a desired substrate 602 such as a metal substrate is first determined by the manufacturer. Then, the first bonding material layer 604 is applied to the surface of the substrate 602. A second or additional bonding material layer 605 is applied to the first bonding material layer 604. The layer of substantially uniform dry particles 606, which are substantially uniform in shape and size, is applied onto the second bonding material layer or top bonding material layer. The thickness of the subsequent bonding material layers applied to the substrate are generally predetermined according to a design specification or manufacturer requirements. A suitable topcoat or final coating layer 608 is applied to the uniform particles to achieve the final coated substrate. It should be appreciated that the thickness of the bonding material layers or coatings on the substrate or the thickness of the overall substrate may vary according to the design specifications. Thus, the final coated product or substrate 600 may be any suitable thickness or composition. Additionally, it should be appreciated that other suitable material layers may be applied to the wet bonding material layer based on specific design specifications or requirements. The material layers may include the same or different materials.

In FIGS. 6B and 6C, the dry particles 606 are uniformly distributed on the material bonding layer or primer layer 604 so that the dry particles 606 are dense and cover every facet of the surface on the primer layer. By using a single layer of substantially uniform dry particles, the topcoat adheres to the maximum surface area of the particles and thereby develops an extremely strong bond between the coating layer and the particles 606 of the underlayment 603a. In one embodiment, a single, substantially uniform dry particle layer 606 is applied to a substrate to promote the adhesion of a coating to the substrate or product. In another embodiment, the method of coating a substrate using the underlayment as described above, may be repeated to apply multiple reinforcing coatings or reinforcing material layers such as multiple topcoatings to the substrate. In this embodiment, the reinforcing material layers are applied until a desired thickness is achieved. The desired thickness may be any desired thickness or suitable thickness predetermined by the manufacturer. Thus, the present embodiment of the underlayment may be used to apply multiple reinforcing coatings or reinforcing material layers to a single substrate and to multiple surfaces on a substrate.

Figure 9:
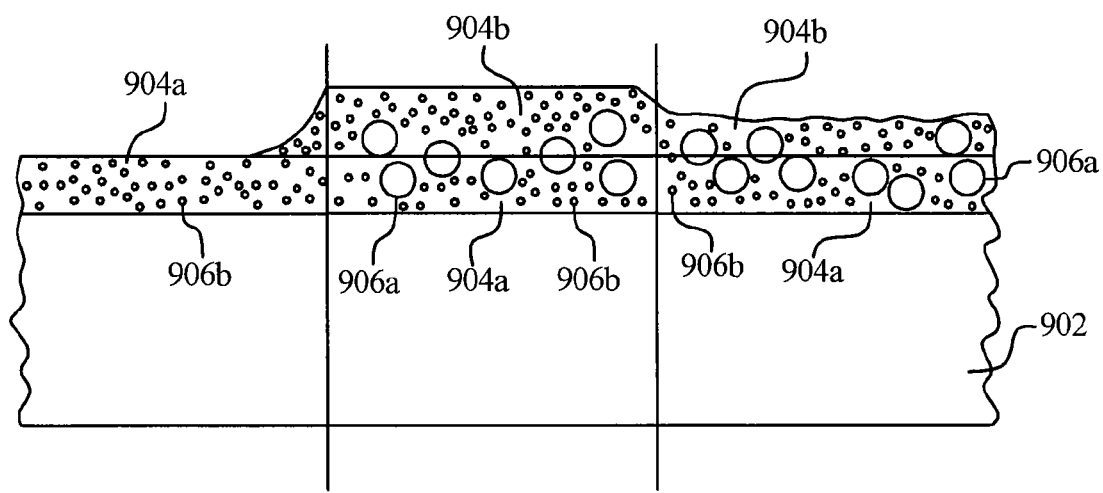
FIG. 9 is an enlarged fragmentary view of a coated substrate of another embodiment of the present invention illustrating multiple material wet material bonding layers including hard and soft particles applied to the surface of the substrate.

Referring to FIG. 9, in another embodiment, a wet bonding material layer 904a including relatively small particles 906b of a suitable low friction or soft material such as PTFE or UHMW is first applied to the surface of a substrate 902 as shown in the left section. Next, a layer of uniform hard dry particles 906a such as bronze particles or other suitable hard particles is applied to the wet bonding material layer. Then another layer of the initial wet bonding material mixture 904b including the relatively smaller particles is applied to the dry particle layer as shown in the middle section. The layers are dried and dissolved using a suitable curing process or other suitable drying process. This causes the top layer or second wet bonding material layer including the small soft particles to shrink and distribute the small soft particles amongst the hard bronze particles as shown in the right section. This creates an abrasion resistant and low friction surface.

Figure 10A:
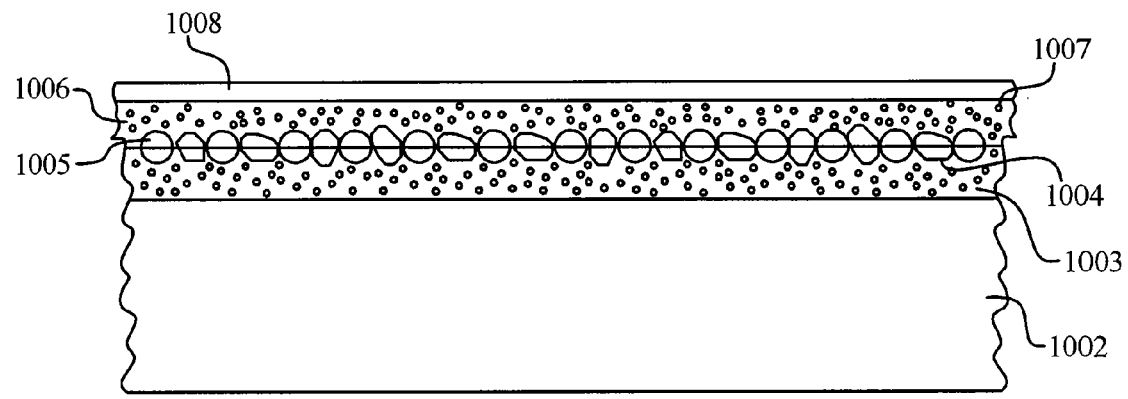
FIG. 10A is an enlarged fragmentary view of an example of the coated substrate of FIG. 9 illustrating a stage of the process for forming the coating on the substrate.
Figure 10B:
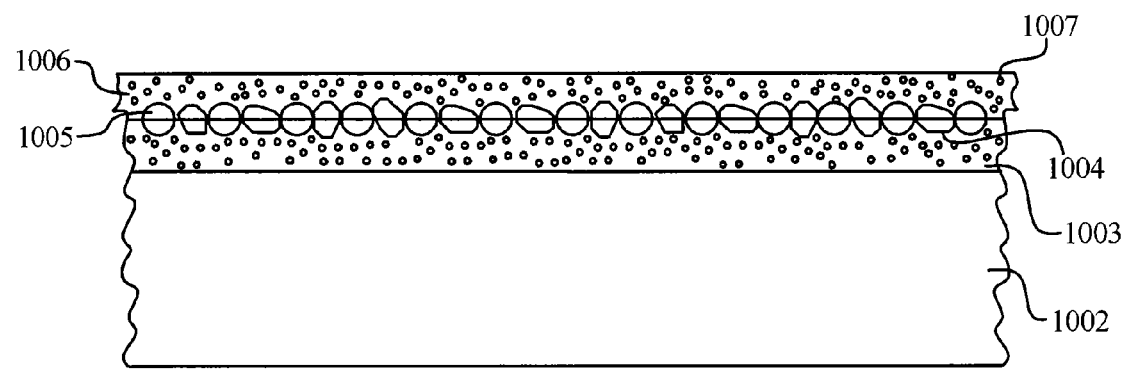
FIG. 10B is an enlarged fragmentary view of an example of the coated substrate of FIG. 9 illustrating the final stage of the process for forming the complete coated substrate.

Referring to FIGS. 10A and 10B, in another embodiment, an initial wet bonding material layer 1003 including relatively small silver plated copper flakes 1007 and spherical copper particles 1004 are applied to a surface of a substrate 1002.

Then, a second wet bonding material layer 1006 including the same mixture of smaller silver-plated copper particles is applied to the surface. A solvent layer 1008 is then applied as a topcoat or final coating on the two wet layers. The layers are then dried using a suitable drying or curing process. This dissolves the solvent layer as shown in FIG. 10B, and partially dissolves the second or top wet material bonding layer to smoothen and sink the silver plated copper flakes and copper particles in the initial wet bonding material layer. The resultant surface includes hard metal particles which resist abrasion while the softer small particles reduce friction on the surface.

Multiple Underlayments

Figure 7A:
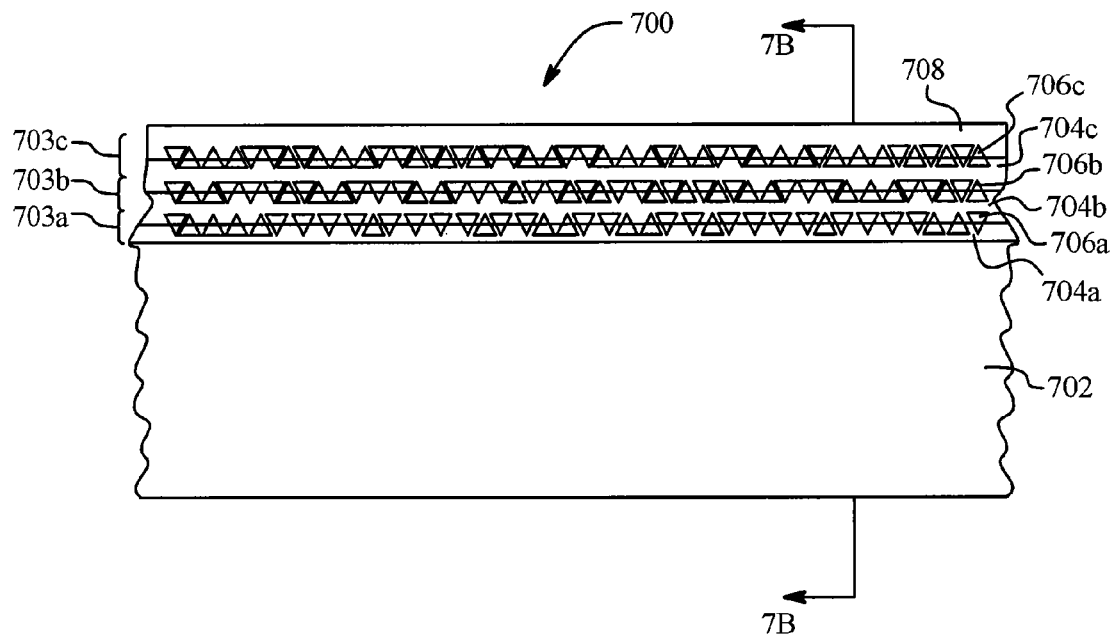
FIG. 7A is an enlarged fragmentary side view of a coated substrate of a further embodiment of the present invention illustrating a coated substrate including multiple underlayment layers and dry particles in each individual layer.
Figure 7B:
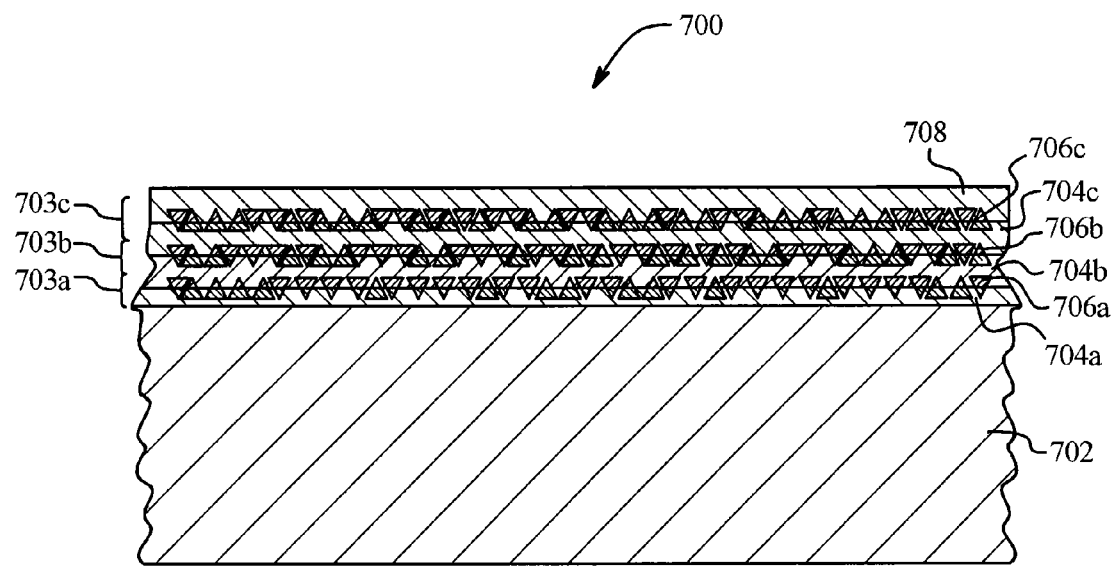
FIG. 7B is an enlarged fragmentary cross-sectional view of the coated substrate of FIG. 7A taken substantially along the line 7B-7B.

Referring now to FIGS. 7A and 7B, multiple underlayments, such as underlayments 703a, 703b and 703c, are applied to a surface of a substrate. The underlayments are applied to create a thicker film on the substrate based on desired design specifications or other suitable design requirements of a manufacturer. Two or more underlayments 703 may be applied to the surface of the substrate. In FIGS. 7A and 7B, in one example, a substrate 702 is first coated with a first layer of a wet bonding material 704a. A first substantially uniform layer of dry particles 706a is applied to the first bonding material layer 704a. A second bonding material layer 704b is then applied to the first layer of dry particles 706a. Then, a second substantially uniform layer of dry particles is applied to the second bonding layer 704b. A third bonding material layer 704c is applied to the second uniform layer of dry particles 706b. A third layer of substantially uniform dry particles 706c is applied to the third bonding material layer 704c. The combination and thickness of the layers or film is determined by the desired design specifications for the layers on the surface of the substrate. A suitable topcoat or final coating material 708 is then applied to the final uniform particle layer 706c. It should be appreciated that any suitable thicknesses or coating layer or layer combinations may be applied to the surface of a substrate.

Figure 7E:
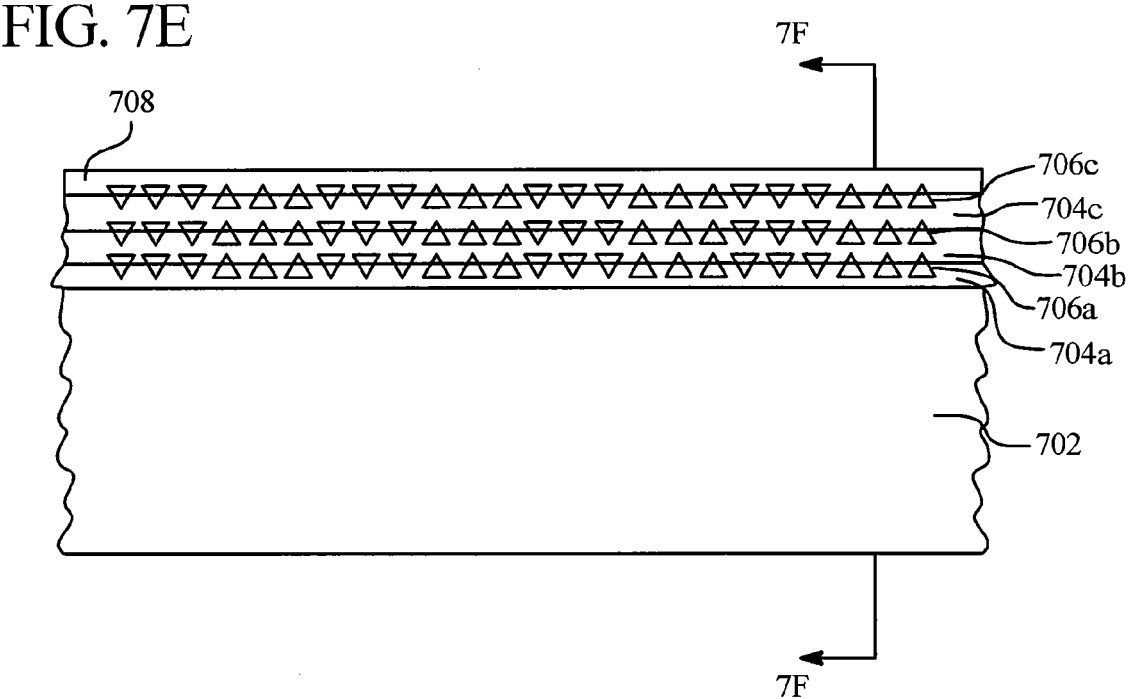
FIG. 7E is an enlarged fragmentary side view of a coated substrate of another embodiment of the present invention illustrating a coated substrate including multiple underlayment layers having angular particles.
Figure 7F:
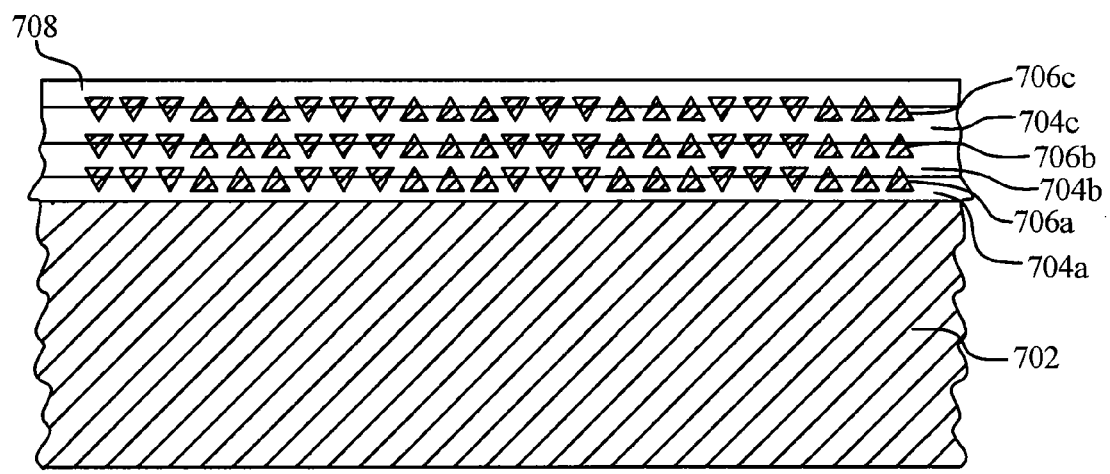
FIG. 7F is an enlarged fragmentary cross-sectional view of the coated substrate of FIG. 7E taken substantially along the line 7F-7F.

Referring to FIGS. 7C and 7D, another example of the embodiment illustrated in FIGS. 7A and 7B are illustrated where the multiple underlayments include substantially spherical particles 706a, 706b and 706c. In FIGS. 7E and 7F, the particles 706a, 706b and 706c are angular particles which are applied in the underlayment layers. It should be appreciated that any suitably shaped uniform particles may be applied to the wet bonding material layers based on the design specifications and end-use criteria.

In the alternative embodiments of the present invention, if wear resistance is required, then the second layer or layer of substantially uniform dry particles is generally the final layer applied to the surface of a substrate. If non-stick or high corrosion resistance is required, then a third and/or fourth wet coating layer or topcoat including a suitable non-stick material or similar material is added to the above layers to increase the non-stick characteristic of the surface of the finished, coated substrate.

Several different types of additives may be added to the topcoat or final coating to improve the performance characteristics of the coated substrate. In one embodiment, a counterface or opposing surface smoothening additive including relatively hard, relatively smaller particles, is added to a topcoat or final coat, to enable the coated substrate to smoothen or polish a rough surface or surfaces, which contact the surface of the coated substrate. In one example, when rough metal surfaces rub against PTFE coated substrates, the PTFE wears away. Quickly, this diminishes the quality and performance of the PTFE on the coated substrate. To remedy this problem, a smoothening additive is added into the wet topcoat of PTFE so that the topcoat or outer layer on the surface of the substrate contains harder particles than the counter surface such as a metal surface. The relative motion between the surface of the coated substrate and the rough metal surface (i.e., the interface), causes the additive particles to disperse as the particles wear away, and also polishes or smoothens the opposing surface of relatively rough metal so that the PTFE topcoat is not worn away prematurely. This also enables the layer below the topcoat to have a smooth counter surface to work against. It should be appreciated that any suitable additive may be added to the topcoat or final coating to improve the performance or desired characteristics of the coated substrate.

EXAMPLES

The above embodiments may be employed in several types of coating processes. In one example, a soft coating, which is commonly used to coat surfaces of cooking equipment, is applied to one or more surfaces of a substrate.

The surface is prepared with cleaning and/or grit blasting to uniformly roughen and clean the oxide layer off the surface, whether it be aluminum, aluminum oxide, steel, glass, ceramic, plastic or any suitable material. A primer bonding mixture or solution including a wet layer of a polyamide-imide (PAI) material is solvated in or dissolved in a solvent comprising a resin such as N-methylpryrrolidine (NMP) is sprayed onto the surface of the substrate so that the thickness of the wet mixture or solution is approximately between 30-50 microns thick. Alternatively, other suitable application methods such as dipping the substrate into the solution or flowing the mixture or solution onto the surface of the substrate may be used to apply the solution to the surface of the substrate. The solids in the PAI is approximately fifteen percent and solids in the NMP vehicle is approximately eighty-five percent. Dry particles or granules of aluminum oxide are then applied to the bonding layer. Preferably, the aluminum oxide particles protrude through and are held by the bonding layer. The particles in this example are approximately 50-60 microns in size which, when the bonding layer shrinks because it is comprised of eighty-five percent solvent and fifteen percent PAI resin, leaves a rough surface not unlike commercial sandpaper. The exception is that each particle has been completely coated with the diluted primer bonding mixture.

In this example, the dry particles are completely coated with the primer bonding mixture because the dry particles are one hundred percent solids, where the primer bonding mixture is primarily a liquid including approximately twelve to twenty-five percent solids. As the liquid bonding material shrinks, it adheres the particles to the substrate through adhesive bonding of the amide-imide to the substrate to itself and to the introduced particles. The resultant underlayment is cured at approximately 300-600 degrees Fahrenheit, depending on the subsequent coating or coatings, if any, which may be applied to the underlayment.

In another example, an amide-imide (AI)/PTFE primer or intermediate compatible material layer, which is compatible with and bonds to the amide-imide layer is applied to the substrate. In this example, the material layers are not cured. However, in one embodiment, a semi-cure of 400 degrees Fahrenheit is used after this phase to cure the layers on the substrate. A relatively pure PTFE coating dispersed in water and some added component of NMP is applied on top of the intermediate PTFE-AI layer. This last coat is flash dried at approximately 200 degrees Fahrenheit until all the water is removed. What remains is the aluminum oxide material held to the surface by, at the bottom of the particles near the substrate, a pure layer of PAI. The next layer still covering the dry aluminum oxide particles includes the intermediate or primer layer of the PTFE topcoat. In one embodiment, the PTFE topcoat has a thickness of approximately 10-15 microns. The intermediate PTFE-PAI coating is in a dry state and has a thickness of approximately 10-20 microns. The purpose of this method is to cover the largest particles of aluminum oxide to approximately 10-15 microns with a PTFE-rich topcoat. The resulting system is passed through an oven with temperature zones of approximately 400 degrees in a first phase to approximately 600 degrees to approximately 800 degrees in a third phase. At approximately 400 degrees, the remaining NMP in the basecoat comes through the liquid layers and helps to unify the bond of all three original liquid layers all of which contain amide-imide (AI). At approximately 600 degrees Fahrenheit, all of the volatiles and solvents are removed by heat evaporation, along with any wetting agents. At approximately 800 degrees Fahrenheit, the PTFE sinters to itself, the amide-imide bonds to the substrate and to the PTFE with a very high bond strength, and the dry aluminum oxide particles are held together by both the lower layer and the intermediate layer of AI coating.

In the above example, wear of the PTFE, which is soft and has non-stick properties, is substantially minimized on the surface of the substrate. Over time, the PTFE layer is worn away until the wear-producing object or objects contact the aluminum oxide layer, which has a substantial hardness of nine on a Mohs' scale. This near-diamond hard material includes jagged peaks as its particulate shape is very angular and multi-faceted. As the entire system is worn, only the peaks of the dry aluminum oxide layer stick through and support each other during the bonding of the lower and intermediate layers. The strength and hardness of the aluminum oxide layer prevents the PTFE from being worn away easily as the rough "mountains" or peaks of aluminum oxide have surrounding "valleys" filled with PTFE, which is protected by the aluminum oxide "mountains." In fact, the aluminum oxide layer must be worn away before the PTFE is able to be worn away. The chemical and mechanical bonds of the PTFE layer to the intermediate and lower layers are so strong that the layers are not dislodged even from substantial cavitation pressures or hydraulic pressures. Essentially, the entire underlayment is locked or secured together. In one embodiment, the quantity of PTFE at the surface is reduced as wear takes place. However, even the partially worn underlayment remains effective as a non-stick layer such as a food contact release when the underlayment still includes approximately 50% PTFE. The PTFE remains effective because the low surface energy of the remaining PTFE layer repels any sticky or substantially sticky products. It should be appreciated that other suitable ceramic or metallic materials including non-stick or lower surface energy characteristics may be employed in the above embodiment instead of aluminum oxide.

In another embodiment, the shape of the dry particles or granules is changed such as to a rounder or spherical particle in a wear resistant application so as to minimize wear or "scratching" of an opposing surface. Additionally, using softer or harder ceramic materials or particles reduces the wear or scratching of the opposing surface or surfaces. As a result, the underlayment can be used in several different applications or products such as on the bottom of a frying pan, which has little or no PTFE.

In a further embodiment, higher temperature, rigid imide resins of particle sizes similar to those of aluminum oxide, approximately 40-60 microns, are used to make an even tougher system including no ceramic material and with a more cushioning or softer effect on the opposing counterface or surface. In one example, a conveyor for transporting glass could be processed using the non-ceramic underlayment particles and provide extraordinary wear yet very slippery surfaces that will not scratch the glass surfaces transported on the conveyor.

In a further example, the amide-imide is used as a bonding material or primer in the underlayment. Also, round bronze dry particles that can be solid or porous, are used in the underlayment instead of abrasive, angular particles. As a result, the underlayment provides wear resistance and reduction in an oil-wetted or oil-containing environment, such as in an automobile shock absorber. Additionally, other automobile parts including wear surfaces such as the rod guide and the wear band on a piston, can be manufactured using the underlayment of this embodiment. Furthermore, graphite, molybdenum disulfide or other additives can be added to the intermediate layer and/or upper coating or topcoat layer to improve the lubrication characteristics of the automobile or appliance parts or other similar parts or products. In the above embodiments, the dry bronze particles are covered by a PTFE or PTFE/resin material including wear-reducing agents such as molybdenum disulfide, graphite, talc, or particles of lead, zinc, antimony, tin, titanium or any other suitable material. Thus, the above embodiments may be used for commercial sliding tables, machine tools, automobile parts and other similar applications to enhance the wear resistance and load carrying capacity and still minimize the friction on the PTFE or PTFE containing intermediate and topcoat layers.

Different Sized Particles

Referring back to FIG. 3 in another embodiment, two different sized particles are applied to a substrate 302 to further enhance the wear-reducing capabilities of a surface of the substrate. The bonding material layer or primer layer 304 is applied first to the surface of the substrate 302, and then several large, dry metal particles 306a such as 125-micron bronze particles are applied to the bonding material layer. Then smaller metal particles 306b such as 25-30 micron lead particles are applied to the initial metal particle layer as an intermediate coating layer or as a topcoat layer. The underlayment of this embodiment therefore provides different wear characteristics based on the different counter surfaces and surfaces of a substrate or substrates.

Figure 8:
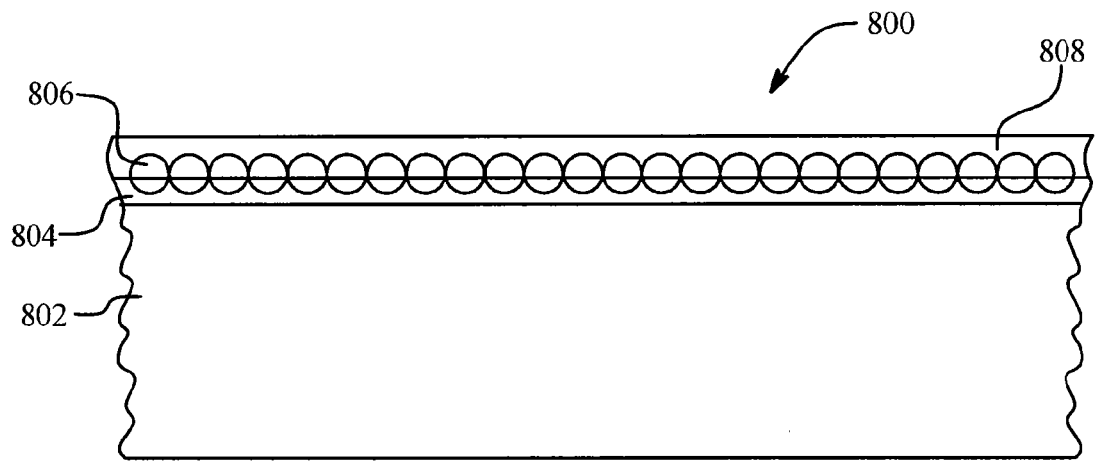
FIG. 8 is an enlarged fragmentary side view of a coated substrate of a further embodiment of the present invention illustrating the uniform particles as substantially uniform round particles.

Referring now to FIG. 8, another embodiment of the present invention is illustrated where the underlayment includes a single uniform layer of substantially spherical or round, dry particles 806. The spherical particles are substantially uniform in size and shape and are applied to a bonding material layer 804 on a surface. A suitable topcoat or final coating 808 is then applied to the uniform particles. The uniform size and shape of the spherical particles promotes the increase of the surface area for a coating to bond to the particles and also reduces the relatively soft particle coating wear rates. It should be appreciated that any substantially uniform size or shaped particles may be employed in the present invention to form the underlayment.

Coating Application Methods

In further embodiments, the coatings are applied using different application methods, which change the structure or bonding strength of the underlayment. In one embodiment, one or more suitable solvents or solvent-catalyst blends are sprayed or applied to the bonding material layer on the substrate simultaneously with the substantially uniform particles. The resultant spray or application method appears as a type of atomized spray, which enables the process to more completely wet the surface of the substrate. This process creates an even stronger bond between the bonding material layer and the uniform particles.

In another embodiment, a powder spray process is used, which enables an operator to better control the application of the layers to the substrate. The powder spray process applies the uniform particles as very fine particles to the lower layers adhered to the surface of the substrate. This process enables an operator to control the density of each of the layers applied to the substrate and also enables the operator to coat odd-shaped substrates with more control and accuracy. In a further embodiment, the electrostatic powder spray is used to apply a topcoat such as a powder paint coating or fluoropolymer powder coating to the surface of the substrate. In this embodiment, a bonding material and then a conductive material or coating is applied to the surface of the substrate. The powder coating is then cured in a convection or infrared oven, and because the powder coating does not include solvent, the heat from the oven heats and shrinks the powder coating onto the top of the dry particles. This type of topcoat may be used in many different industrial applications such as to produce electrical characteristics or increasing abrasion resistance of commercial bakeware and cookware.

In a further embodiment, electrostatic, tribo-charged or opposite electrostatic charged powder technology is used to further enhance the dry particle attachment or adherence to an odd-shaped configuration. The dry particles may be electrically insulative, but treated with a veneer of very thin conductive or insulative materials, such as the materials sold by the Ransburg Corporation, for creating electrostatic properties on substrates such as wood. In one embodiment, the dry particles are "soaked" with these electrostatic enhancing coatings or materials and subsequently dried or applied in a wet state with more conventional spray gun technology designed for wet materials. If the harder particles are ceramic and the configuration is very odd and angular, such as a fan housing or fan blades, electrostatic powder technology enhances the distribution of the dry particles. The bonding material layer or primer is altered to provide maximum electrical grounding potential by using solvents that are electrically conductive and contain water in some cases. This provides the maximum attraction of the dry particles to the bonding material layer, which provides a uniform, dense coating as desired by the application in all areas of a vessel or industrial component, such as a fan blade as shown in a centrifugal fan or turbine.

In the tribo-charging process, the tribo-charging is accomplished by stripping the electron off a particle of powder. This is accomplished by passing the particle over an opposite charged material that strips the electron off which is passed to ground or earth. This is commonly used by passing nylon particles through PTFE tubes by using air pressure to move the nylon particles at high surface speed over the PTFE surface. The opposite holds true. If PTFE particles are passed over nylon surfaces, they lose the outer layer of electron charge and are attracted to ground or a grounded article or surface.

In another embodiment, the wet materials can be introduced with conventional spray or electrostatic spray technology to apply the bonding material or primer to a surface of a substrate. In one example, a shaft, on which a wet bonding material layer is applied, is rolled over an electrostatic, aerated, fluidized bed of approximately 100,000 volts passing through an electrostatic grid with the dry particles suspended over a porous membrane of polyethylene. When air pressure is introduced underneath the electrostatic grid in an open top container, the dry particles become charged by the air passing through and past an electrical grid, which is placed slightly below the insulated polyethylene membrane. The charged dry particles above the porous polyethylene membrane are uniformly attracted to the wet substrate on the surface of the shaft, which is suspended and rotated above the fluidized bed. Because of the self-limiting characteristics of the electrostatic method, the dry particles are uniformly applied as the particles are applied to the substrate. The applied dry particles, as the particles are deposited, create an insulated layer in the areas where the dry particles are attached or attracted to the wet bonding material layer. This method provides a very uniform application of the dry particles to the surface of the substrate at high speeds and at low commercial costs.

In a further embodiment, the substantially uniform aluminum oxide particles are applied to a surface of a substrate to achieve a desired roughness on the surface. The desired surface roughness is achieved by changing the size of the aluminum oxide particles applied to the surface. The aluminum oxide particles are applied to a thin bonding material layer on a surface of a substrate and create a very strong bond with the surface of the substrate. The aluminum oxide particles may be applied to various surfaces including the surfaces of rigid parts. The application of the aluminum oxide particles to roughen the surface or surfaces of a substrate substantially minimizes the distortion to the surface, which occurs with conventional blasting methods, and enables a user to control the roughness of the surface. In addition, harder particles such as boron nitride particles or other suitable particles can be applied to the surface of the substrate to increase the penetration resistance of the surface.

Selective Application of the Uniform Particles

The wet bonding material layers are generally applied to the entire surface of a substrate. In one embodiment, the uniform particles are applied onto the entire wet bonding material layer. In another embodiment, the uniform particles are applied to specific areas on the wet bonding material layer on the surface of the substrate. In this embodiment, a mask of a suitable masking material is applied to the wet bonding material layer to prevent the adherence of the uniform particles to the masked areas. Thus, a surface of a substrate such as a particular surface or portion of a surface of a part can be masked or selectively coated with a suitable masking material so that the dry uniform particles are applied to specific areas of the surface of the substrate. In one example, specific surfaces of a cooking pan such as a sauté pan or wok are selectively coated with a non-abrasive and/or non-stick material to reduce abrasion and wear on those surfaces of the pan. A metal utensil is commonly used to stir or mix food products in the pan, which causes abrasion of the surfaces of the pan. The abrasion is generally focused on the bottom surface of the pan and not the side surfaces because the bottom surface of the pan gets hot causing the food products to stick to the bottom surface. Efforts of a user to dislodge the food product from the bottom surface using a metal or similar utensil, concentrates the vast majority of the wear on the bottom surface of the pan. Therefore, to increase the abrasion resistance of the bottom surface of the pan, a wet bonding material layer is applied to the entire cooking surface of the pan followed by a selective application of abrasion resistant particles, such as relatively hard particles, to the bottom surface of the pan. This is accomplished by applying the wet bonding material to all of the surfaces of the pan. Then, a mask or suitable masking material, which does not allow the uniform particles to adhere to or partially adhere to it, is applied to the surfaces of the pan except the bottom surface of the pan. The abrasion resistant particles therefore, will only adhere to the bottom surface of the pan and not to the masked surfaces. In one embodiment, the above applications are followed with a thin application layer of smaller sized dry reinforcing particles to the entire surface of the pan. In all cases, a topcoat including a non-stick material is applied to the entire surface of the pan.

The present embodiment can also be used in industrial applications to reduce cost and/or improve machine tolerances. In one example, the cylindrical area and top of the valve are coated with the wet bonding layer. A uniform dry particle layer is applied by then inverting the solenoid valve so that the uniform dry particles contact the sides of the cylindrical area of the solenoid while it is being rotated. Gravity causes the excess dry particles to drop down providing no dry particles that are adhered to the bottom wet area of the valve of the solenoid. The solenoid surfaces are then completely cured using a suitable curing process. Subsequently, bronze particles are applied to the outside surface of the cylindrical area and then covered with a thin, appropriate topcoat. The face of end surface of the solenoid is only coated with a single coating of the original wet bonding material layer, which has been cured as described above.

Magnetic Particle Embodiment

In a further embodiment, dry magnetic particles are applied to the wet surface of a glass or non-magnetic metal substrate to completely coat the surface of the substrate. In one aspect of this embodiment, a magnetic shape is placed on a surface to be coated, either under, above or both under and above, the surface. The magnetic shape may be any shape, symbol, character or other suitable image. The shape will appear on the surface of the substrate as the magnetic particles orient themselves due to the magnetic forces attracting the magnetic particles while the magnetic particles "float" in the liquid layer. A suitable non-magnetic material, such as aluminum or glass, is used as the substrate.

One example is a glass or metallic baking pan. A wet bonding material is first applied to the surface. Magnetic particles, such as magnetic stainless steel or magnetic iron particles that are dry, are applied to the non-magnetic pan. The wet bonding layer stays moist during this dry magnetic particle application phase. A magnetic image, which might be a company logo, part number, identification or other suitable identifier, is created with a highly magnetic force field. This may be electromagnetic or magnetic in nature comprising a predetermined shape. The magnetic shape can be suspended below and in contact with the pan or it can be suspended slightly above the surface of the magnetic particles, not touching the particles. The magnetic forces will affect the magnetic material that has been introduced as a dry particle to the wet base bonding layer and the shape of the magnetic forces will be shown in the pattern in the coating created by the orientation of the metallic particles.

Various blends of metallic particles can be used and various shapes can be blended into the dry layer so that very distinct images appear in the layer depending on the formulations of the dry particles. In one example, a coffee cup that has had a wet bonding layer applied followed with an application of the dry magnetic material can have a company logo created with an electromagnet or solid magnets, such as Rare Earth or Alnico magnets, which will orient the magnetic particles that have been introduced to the wet bonding layer to create an image that is that of the company's logo. It should be appreciated that the letters would be reversed, in mirror images, if placed below the pan so that the viewing of the pan from the topside, where the wet bonding/dry magnetic particle layer is applied, reads correctly. This could be followed immediately, while the magnetic forces are held in place, with a semi-curing infrared heat cycle which would harden the wet bonding layer so that the orientation of the magnetic particles while they are being magnetized would hold the formed shape. In this embodiment the magnetic particles may be ferrite particles, ferrous particles, or any suitably magnetic materials, including stainless steel. In one aspect of this embodiment, the magnetic particles are densely packed at the surface due to the forces the magnetic field places upon the particles at the surface and on the surface of the substrate. The magnetic contraction or alignment occurs within the wet bonding layer while the magnetic particles "float" before the wet bonding layer is hardened through a curing operation.

In a further embodiment, ferrite particles are applied to the surface or surfaces of a substrate over a wet bonding material layer to absorb microwaves or similar waves such as in a microwave oven. For instance, the ferrite particles may be applied to a wet bonding material layer on a glass container. This step is repeated several times until the ferrite particles, which are chosen for their microwave absorptive capabilities, have sufficient depth to create and transfer energy in the form of heat to food products inside the glass dish while in a microwave oven. In this embodiment, the entire glass dish or bowl would be coated with the wet bonding material layer, which would be opaque in nature. The ferrite particles are introduced only to the bottom of the dish. This would allow, when the complete system is cured, for the microwave energy to be absorbed in the center of the dish. For example, a microwave popcorn maker could be made in such a manner in which the heat was concentrated at the bottom of the microwave vessel, container or dish allowing the newly popped corn to leave the hot surface and be replaced by heavier and denser popcorn as it falls into the center of the curved dish. In another example, medical sterilization equipment could be manufactured with plastic and the bonded ferrite layer, which would produce localized heat in certain areas of the plastic as determined by the introduction of the ferrite particles where necessary.

In a further embodiment, the coated substrate is cured using induction heating. In this embodiment, induction or magnetic sensitive particles such as uniform metal particles are applied to the wet bonding material on the surface of a substrate. The metal particles may include uniform magnetic stainless steel flakes or stainless steel particles. The flakes or particles are rearranged in the wet bonding material using a magnet or other suitable magnetic device. Induction waves, which are reverse magnetic fields, are then directed at the coated substrate to induce heat in the wet bonding material. The heat induced in the wet bonding material cures the wet bonding material to produce the final coated substrate. In another embodiment, an induction heat device is used to raise the temperature of the substrate and thereby cure the wet bonding material layer.

Density of Uniform Particle Layer

In a further embodiment, the strength of the bonds and the layers on the substrate are increased by increasing the density of the uniform dry particles that are applied to the bonding material layer on the surface of a substrate. In one aspect of this embodiment, commercial, unmodified or modified grit blasting or sandblasting equipment is employed to apply the dry particles to the bonding material layer. The density of the particles in the bonding material layer is increased by increasing the pressure of the spray and the velocity of the dry particles and the rate of speed in which the coatings are applied to the bonding material layer. The increased pressure of the dry particle depositing spray and the rate at which the dry coating or dry coatings are applied to the bonding material layer, increases the packing or density of the particles in the wet bonding material layer. The pressure of the spray and/or the rate of speed of the spray may be adjusted to maximize the density of the dry particles based on the desired design specifications.

The high-speed introduction of particles into the bonding material can also be used when multiple-sized dry particles are applied to the surface of a substrate. In one example, a first layer includes relatively small particles of approximately 20-50 microns, followed by the application of relatively large particles of approximately 150 microns followed by the application of relatively small particles of approximately 20-50 microns followed by the application of smaller particles of approximately 10-20 microns. In this embodiment, the density of a 30-40 micron wet bonding material layer is increased and also the interconnectivity or contact between particles is enhanced. This layer, when wet, will be 30 microns, but the finished layer may actually be greater with the 150-micron particles protruding from the surface and causing the surface of the substrate to be slightly textured.

Particle Encapsulation

In an alternative embodiment, the substantially uniform dry particles are pre-treated, encapsulated or micronized with a wet bonding material such as an adhesion promoting encapsulent or catalytic reactive material producing encapsulent prior to being applied to the wet surface on a substrate. One example of an adhesion promoting encapsulant is a silane coupling agent or silane. The wet bonding material applied to the dry particles may be the same or different from the wet bonding material applied to the surface of the substrate as described above. Preferably, the bonding material is compatible with the bonding material layer applied to the surface of the substrate and any other coating layers applied to the substrate. In one embodiment, the particles are placed in a rotary device such as a tumbler. The bonding material is sprayed or applied as droplets into the tumbler and thereby evenly distributes and coats the dry particles as the particles rotate in the tumbler. The bonding material basically coats all of the areas of the dry particles with a thin veneer. The coated particles are dried or semi-cured to encapsulate the dry particles, and then applied to the wet bonding material layer.

In one embodiment, a curing cycle is employed to semi-cure the wet bonding agent or bonding material, which contains a resin and a solvent to the once dry particles. The extra curing process enables the dry particles to adhere to each other and also evaporates or removes the solvent from the base or initial coating layer, which strengthens the bond between the dry particles and a intermediate or lower layer on a surface of a substrate. Thus, pre-coating or pre-treating the dry particles with a bonding material enhances the bonding capabilities of the particles to each other and enhances the bonding strength between the particles and the bonding material layer on the surface of the substrate and subsequent applied layers.

Wave Absorption Embodiment

In one embodiment, the present method is used to attenuate or absorb magnetic, electromagnetic, radio or other airborne waves or signals such as in a medical X-ray room or similar area such as in RF shielding. Currently, sheets of metal such as copper or similar materials are used to cover the surfaces in these areas. In the present method described above, a wet bonding material is applied or sprayed onto a vertical or horizontal surface or substrate such as a wall or floor in a room. In this embodiment, it should be appreciated that the base material layer such as the bonding material layer may have a thickness of approximately 125-150 microns.

After the wet bonding material is applied to the surface or surfaces, a suitable magnetic wave or other suitable absorbing type material such as dry copper particles, which may have a thickness of approximately 50-75 microns, are applied to the wet bonding material layer. These relatively smaller particles fill in the areas that are still wet between the larger particles. Additionally, a leafing material such as silver, nickel, copper, bronze, or any other conductive material may be applied to the uniform dry particles. Once the coated substrate is grounded using the leafing material, the entire exposed surface acts as an electrical conductor such as a sheet of metal. Thus, additional layers can be added to the multiple layers of the original formulation of primer or bonding material. The sequence can be repeated until the thickness of the layers is approximately 400-500 microns or greater. The multiple sized particles in this underlayment contact each other interconnectedly to provide an essentially impermeable barrier to radio waves or any other airborne electromagnetic or electronic waves.

The benefit of the underlayment including the wave reducing or absorbing layer is that the metallic particles are densely compacted into the wet bonding material layer. In conventional coating processes, the particles are applied to the surface of a substrate as a part of the wet coating and therefore, the coating may actually prevent contact between the particles. Conversely, careful formulation of the bonding material layer actually produces a shrinking or cohesive effect which increases the density of the layers as the layers are dried or catalyzed in place.

Thus, the present invention enables the dry copper particles to completely cover the desired surfaces and thereby minimize or eliminate the gaps and seams produced by conventional methods, which cover or line walls in a room with sheet of metal such as copper. Additionally in one embodiment, a flexible bonding material is used to enable the coatings to better adhere to the surfaces, twists and bends of the surfaces such as corners in a room. In one aspect of this embodiment, to enhance the adherence and coverage of the particles to the bonding material layer, an electrically conductive bonding material is used to attract the oppositely charged particles.

In RF shielding on plastic, many materials have been used which contain leafing particles of copper, bronze, and other similar materials to provide a metallic shield over plastic parts. In all cases, these liquid coatings with high-solids metals had problems with distribution of the particles because of the settling characteristics of the heavy metals, particularly the copper and bronze. Also, the uneven distribution of particles caused the particles to remain substantially separated by the carrier resin, which negatively affects the conductivity of the coating. Thus, the coatings must be applied thicker and thicker to minimize or eliminate the voids or separation of the particles in the coating where radio waves or electromagnetic waves may permeate an opening in the coating or coatings.

Adhesives

In one embodiment of the underlayment of the present invention, the materials can be more effectively bonded to the plastics using two-part adhesives, such as epoxy and urethane and a very dense metallic layer, which would include pure metal interconnecting metallurgically with intimate particle-to-particle contact. In this embodiment, the impingement velocity of the dry particles sprayed onto the wet bonding material causes the dry particles to stick to the bonding material layer, which provides a dense particle layer. The density of the particle layer may be increased by using multi-sized and multi-shaped particles. The dry particle layer can be electrically tested before further coatings are applied to the dry particle layer. This enables a user to be able to test the conductivity of the coatings before additional layers are applied and also enables the user to reinforce a section or area of the underlayment with more particles, if more particles are needed based on the conductivity.

Industrial Applications

In another embodiment, industrial sifters, strainers, filters and similar industrial components, which are comprised of thick plates with perforated holes, are completely coated with wear resistant coating using the underlayment of the present invention. For example, commercial laundry dryers used in hospitals can be six feet or greater in diameter and ten feet or longer, comprising of several curved plates bolted to a structure, which resembles a drum when complete. In this case, the scraping of clothing and plastic items against the non-stick surface or surfaces of the dryers wears the surfaces away. Using the underlayment of the present invention, the non-stick surfaces of the dryers is substantially strengthened and the wear resistance of these surfaces is significantly enhanced.

In another example, a surface or surfaces of industrial centrifuges are coated. Industrial centrifuges incur great wear during operation. With conventional technology, hard particles such as stainless steel particles are made molten and directed towards a surface or surfaces of a substrate such as by using an arc spray or plasma detonation with detonation gun technology, to increase the roughness of the surface or surfaces. This application method, however, typically coats the surface or surfaces which are at right angles to or directly impacted by the spray, but fails to completely coat the inside surfaces of vertical holes which are on surfaces parallel to the direction of the spray.

In the embodiment of the present invention, by using electrostatic spray technology to apply the bonding material layer to the surface or surfaces of the substrate, the uniform dry particles completely cover the flat surface of the inside of the centrifuge, but also, all of the holes that allow media to pass through the centrifuge. By using this electrostatic combination of liquid and subsequent powder-spray application, the inside surface which defines the holes are strengthened through the uniform application of the wear resistant dry particles. Present technology does not strengthen the inside surfaces of the holes. Thus, in conventional centrifuges, the media passing through the holes eventually wears away the soft non-stick coating on the surface or surfaces of the surfaces of the centrifuges. With the present invention, the flat surface and the surface which defines the holes are completely coated and protected. This is substantially different than the conventional technology in that the distribution of the wear-resistant particles in the conventional technology is focused on the flat surfaces and does not completely coat the surfaces. With the present method, the electrostatic attraction of the particles to the wetted surfaces, ensures complete coverage of the bonding material layer to the flat surfaces and the holes.

In a further embodiment, the present invention is employed in a rotary molding system such as a reactor or commercial dryer vessel to improve the wear resistance of the system. The predetermined quantity of bonding material is filled into the vessel such as the reactor cavity or main dryer compartment and rotated in a multi-directional manner to completely and uniformly coat the inside surface of the vessel. Then, suitable substantially uniform abrasive-resistant particles or other suitable particles are filled into the vessel and are applied to the bonding material layer on the inside surface of the vessel using the multi-directional rotation of the vessel described above. After the dry particles coat the surface, the vessel is inverted and the excess particles drop out of the vessel. The bonding material and dry particles on the surface are cured using a suitable curing process and a final coating or topcoat is then applied to the uniform particle layer if desired.

In one example, a powder fluoropolymer topcoat, such as PFA or FEP includes a combination of either a resin with PTFE and/or any suitable and appropriate modifiers and strengthening agents, such as graphite, talc, and lead powder. The underlayment is created and cured at a temperature of approximately 750 degrees Fahrenheit or lower, depending on the bonding resin or material that is used in the process. The fluoropolymer-rich topcoat, which is in powder form, is applied to the underlayment for wear resistance, if necessary, such as in a machine channel or guide or commercial baking pan or similar bakery or food processing equipment.

The underlayment, if it consists of aluminum oxide or similar abrasion-resistant particles, which are very hard, is coated with the fluoropolymer powder mixture and FDA or food contact ingredients are selected to comply with FDA requirements. This allows the creation of a highly wear resistant, non-stick coating with a powder topcoat.

In another example, preparation for arc spraying stainless steel wire and titanium wire, to create a bumpy or rough base requires an extensive amount of grit blasting and surface preparation to roughen the surface for the mechanical grip such that these dissimilar metals, when impinged in a molten state on the surface, cannot bond metallurgically. With the underlayment of the present invention, the dry uniform particles are bonded and tightly adhered to a surface of a substrate through contemporary adhesive technology and function at and beyond the temperature constraints of typical topcoatings, such as PTFE, which has a limit of approximately 550 degrees Fahrenheit. In other words, the adhesive bond strength and temperature capacity of the underlayment is greater than the temperature capacity of the subsequently applied topcoat layers or topcoats.

Multiple Coating Applicators

In an alternative embodiment, a coating system includes a plurality of coating or material applicators, at least one container having a wet bonding material, at least one container having substantially dry particles, wherein the containers are connected to the coating applicators using at least one coating line or tube, which transports the materials from the containers to the coating applicators. It should be appreciated that the coating applicators may be spray guns, electrostatic spray guns, powder spray guns or any other suitable applicators. The coating applicators are positioned adjacent to the surface or surfaces being coated on the substrate.

In one aspect of this embodiment, one of the coating applicators applies the wet bonding material to the surface of the substrate and the other coating applicator applies an even, substantially uniform layer of the dry particles to the wet bonding material layer. The applicators may apply the coatings at the same rate or at different rates. The coating applicators apply each layer to the surface of the substrate until a desired thickness is achieved.

In one example, the coating system includes multiple coating or material applicators such as two electrostatic spray guns or powder spray guns, to apply an epoxy-based material to a surface of a substrate. The epoxy is made up of relatively dry particles which are applied using electrostatic attraction to the surface. While the dry epoxy is in place, a thin layer of a wet bonding material is fog-sprayed or applied to the dry epoxy particles to slightly dampen the surface of the particles. Then, a powder spray of aluminum oxide, bronze, ceramic, glass or any other suitable material is applied to the bonding material on the particles. The layers are then heated or cured. Subsequently, a final coating such as a wet or dry film, may be applied to the cured layers. In one example, an epoxy base is applied to the surface of the substrate. Then, a wet film including a solvent and water is applied to the epoxy to wet the epoxy and provide some stickiness on the surface. A dry powder spray of non-electrostatic particles are then applied to the surface.

It should be appreciated that the underlayment of the present invention can be used as a single process without any topcoats to provide adhesion of paper or grip or tractive strength as related to moving paper or other products with a roller at high speeds. Additionally, the underlayment could be created with approximately 30 to 40 micron thick bonding material layer and an approximately 200-micron sharp particles of aluminum oxide or boron nitride or other very high-wear resistant ceramics and provide an abrasive gripping surface.

Electrosurgical Electrodes

Figure 11:
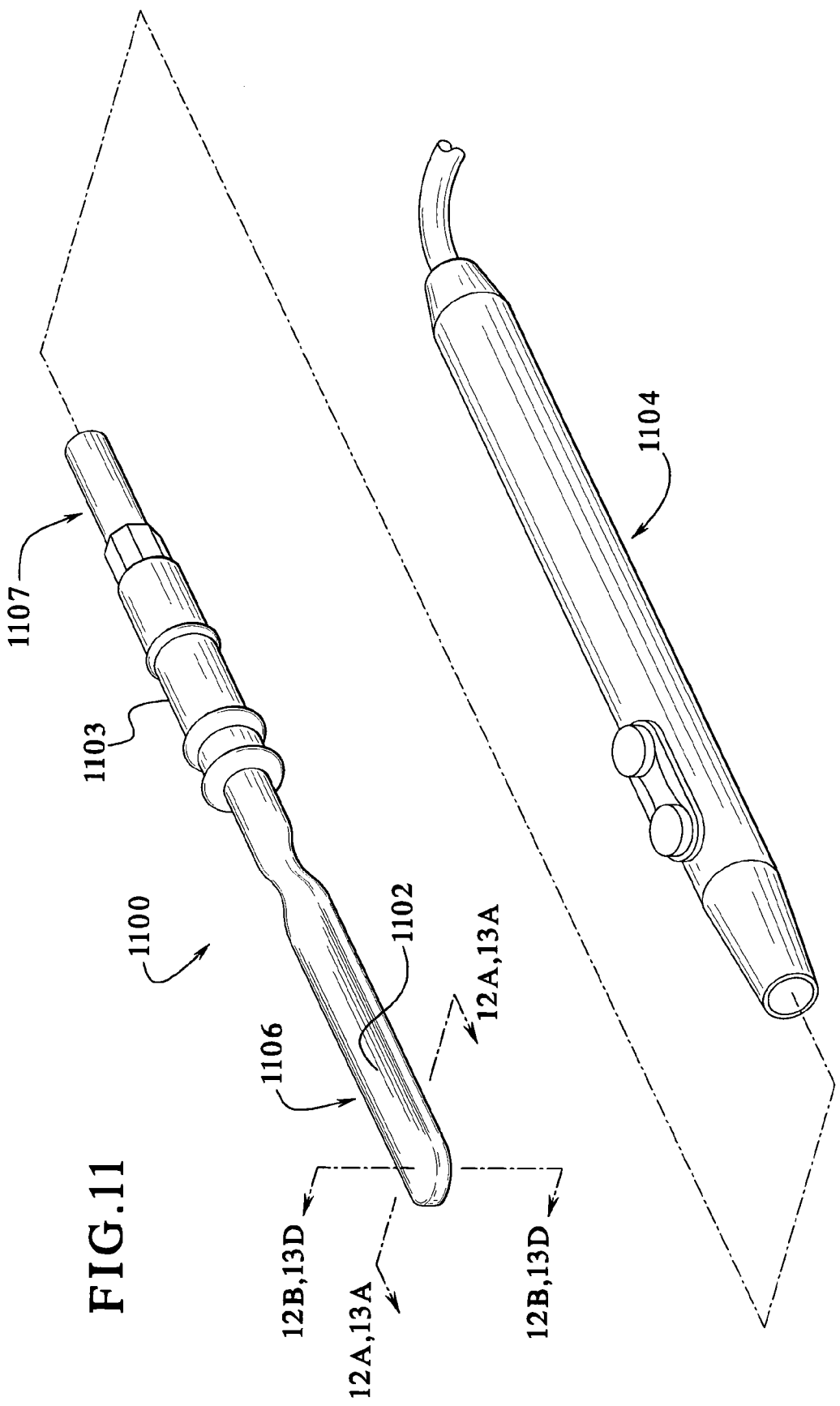
FIG. 11 is a front perspective view of one embodiment of a coated electrosurgical instrument of the present invention.

Referring now to FIG. 11, an alternative embodiment of the present invention is illustrated where a coating is applied to an electrosurgical device such as an electrosurgical instrument, blade or knife 1100. In this embodiment, the coated electrosurgical instrument 1100 includes an electrode 1102 and a holding device such as handle 1104 or other suitable holding device which is connected to the electrode 1102 and enables the electrode to be manipulated in a surgical procedure. The electrode includes a conductive substrate or conductive material which enables the electrode to conduct electrical energy or electricity. In one embodiment, a portion of the electrode 1102 is coated, encapsulated or over-molded with an electrically insulative and non-stick material 1103 such as a suitable plastic. The coated electrode 1102 includes a distal end or working end 1106 and a proximal end or connection end 1107. The exposed distal end 1106 of the electrode is used to cut, coagulate and/or cauterize tissue in a body during a surgical procedure. Specifically, electrical energy such as electricity is transferred from a suitable electrical source through suitable wiring 1109 to electrical conductors (not shown) inside the handle 1104. The electrical energy is then transferred from the conductors (not shown) in the handle 1104 to the proximal end 1107 of the electrode 1102, which is electrically connected to the conductors in the handle, and energizes the electrode 1102. Once energized, the electrical and thermal energy produced by the electrically charged electrode generates an elevated temperature which enables the distal end 1106 of the electrode to cut, coagulate and/or cauterize tissue in a body.

In one embodiment, an anti-microbial, non-stick coating is evenly applied to the entire surface of the electrode to minimize the buildup of tissue or eschar on the working surface of the electrode and to kill a substantial amount of the bacteria or any harmful organisms that reside in or on the exposed distal end 1106 and any harmful organisms that might get underneath the insulative material portion 1103 of the electrode through a gap between the insulative material portion and the electrode. In one embodiment, the coating includes a non-stick material having a plurality of anti-microbial particles interspersed in the non-stick material. The non-stick material includes at least one of the following materials: silicone, polytetrafluoralethylene, fluoropolymers and a combination of fluorosilicones. It should be appreciated that any suitable non-stick material may be used in the coating. Additionally, the anti-microbial particles include at least one of the following materials: silver particles, ceramic particles and combinations of silver and ceramic particles or any other suitable anti-microbial particles. It should also be appreciated that the anti-microbial particles may be any suitable anti-microbial and/or anti-bacterial particles or materials. In this embodiment, the non-stick material minimizes the buildup of tissue or eschar on the surface of the electrode by minimizing the adherence of the tissue on the surface of the electrode. Specifically, the non-stick material or coating forms a slick or slippery surface where a substantial portion of the tissue slides or moves off of the electrode. This enables a user such as a surgeon to continue a surgical procedure without having to continuously clean, scrape or brush off adhered charred tissue from the surface of the electrode.

The anti-microbial particles kill a substantial amount of the bacteria and other harmful organisms that reside on the working surface of the electrode, underneath or adjacent to the insulative material portion 1103 on the electrode or in or on the surface of the adhered tissue, which contacts the anti-microbial particles in the coating on the surface of the electrode. This minimizes and/or prevents bacteria and any other harmful organisms from remaining and growing on the surface of the electrode and then entering the body to cause an infection or other complications after the surgical procedure is complete.

In one embodiment, the anti-microbial particles include silver particles or particles including silver compounds. The silver particles or compounds act as an anti-microbial or anti-bacterial agent which kill the bacteria and other harmful organisms as described above and prevent the organisms from entering the body via the electrode. Silver or silver compounds have a relatively high electrical conductivity. Therefore, the silver particles applied to the surface of the electrode more evenly distribute the temperature and electrical energy transferred to the electrode while increasing the electrical conductivity of the electrode. The increase and relatively even distribution of electrical energy or electricity to the electrode enables the electrode to minimize "hot spots" or portions of the electrode which have a higher temperature due a disproportionate or non-uniform distribution of the electrical energy to the electrode. As a result, a surgeon can make more precise cuts or coagulate or cauterize discrete or specific parts of the tissue in the body with more accuracy. This improves the surgical procedure and also minimizes the time of the surgical procedure. The amount of or density of the silver particles or compounds included in the coating can be adjusted to increase or decrease the conductivity of the coating applied to the surface of the electrode. It should be appreciated that any suitable anti-microbial polymer agents or particles can be used to coat a surface or surfaces of the electrode.

Referring now to FIGS. 12A and 12B, one embodiment of the method of applying the coating to the electrosurgical device such as the electrosurgical blade 1100 of FIG. 11 is illustrated where a single even layer of coating is applied to the surface of the electrode 1102. The electrode 1102 includes major surfaces 1108 and minor surfaces 1110. Initially, the surfaces are roughened by grit-blasting the surfaces or by using any suitable surface roughening method to promote the adherence of the coating to the surfaces of the substrate. The coating is uniformly and evenly applied to the major surfaces 1108 and minor surfaces 1110 of the electrode as shown in FIG. 12A. In this embodiment, the coating 1112 includes a non-stick material having anti-microbial or anti-bacterial particles 1113 interspersed in the non-stick material. In one embodiment, the particles are added to the base coating or material and mixed prior to applying the mixed coating to the electrode. The coating is applied evenly to the surfaces of the electrode 1102 and enables the electricity to be evenly conducted and displaced across the surfaces of the electrode. Additionally, the anti-microbial particles 1113 included in the coating 1112 are dispersed throughout the coating so that a substantial amount of any bacteria or other harmful organisms, which engage or contact the surface of the coating 1112 on the electrode 1102, are killed. This provides substantial benefits in a surgical process because the likelihood of infection or other complications arising after surgery are reduced.

After the coating is applied to the surface of the electrode 1102, the coating 1112 is at least partially cured in an oven such as an infrared oven or other suitable type of curing oven or procedure. The curing process causes the coating to harden and adhere to the surface of the electrode 1102. The coating is applied to the surface or surfaces of the electrode 1102 until a desired thickness 1114 is achieved. It should be appreciated that the coating may be applied to any suitable thickness.

Figure 13A:
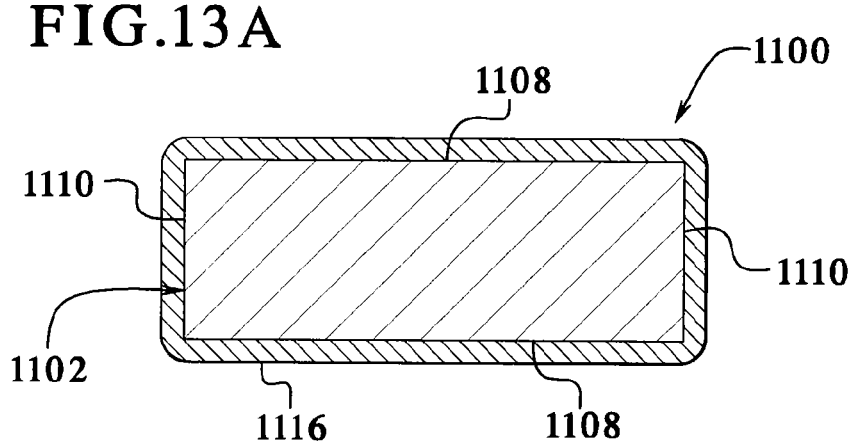
FIG. 13A is a cross-section view of another embodiment of the electrosurgical instrument of FIG. 11 taken generally along the line 13A-13A where a primer or base coating is applied to the surfaces of the instrument.
Figure 13B:
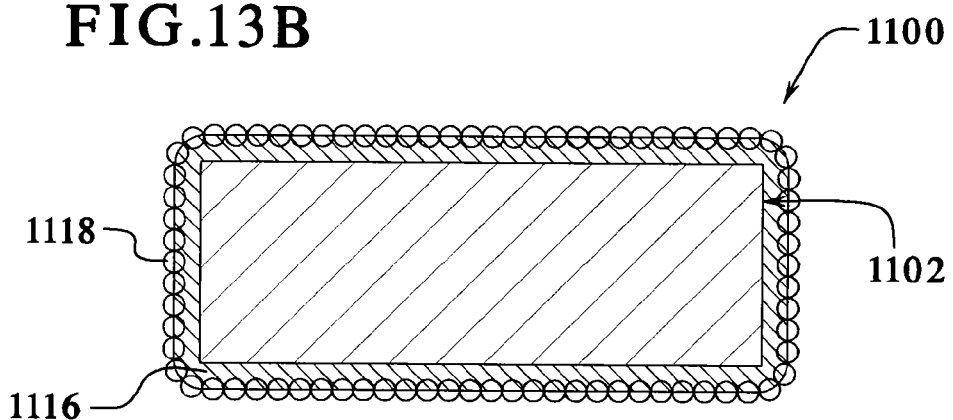
FIG. 13B is a cross-section view illustrating the embodiment of FIG. 13A, including a layer of anti-microbial particles.
Figure 13C:
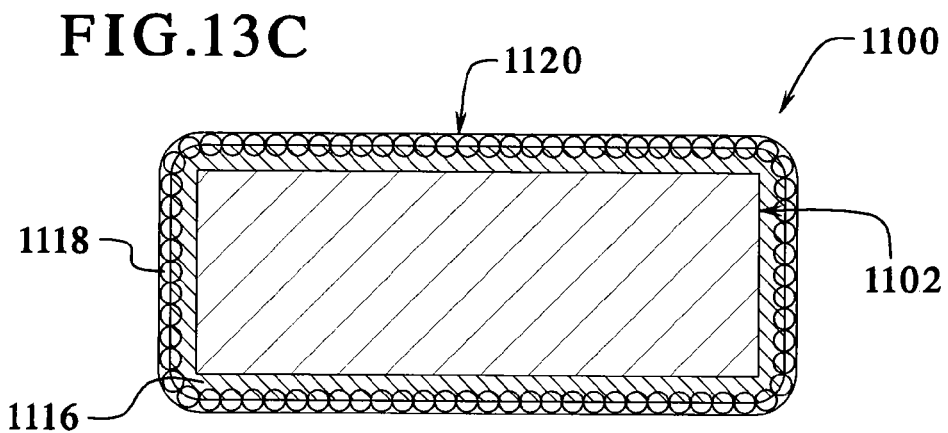
FIG. 13C is a cross-section view of FIG. 13B, including a top coating applied to the layer of anti-microbial particles.

Referring now to FIGS. 13A, 13B and 13C, another alternative embodiment of the method of the present invention is illustrated where multiple coatings are applied to the surfaces of the electrode 1102 of the electrosurgical device 1100. In this embodiment the major surfaces 1108 and minor surfaces 1110 of the electrode are initially roughened as described above to promote the adherence of the coatings to the surfaces. After the surfaces are roughened, a wet bonding material such as a primer 1116 is applied to the major surfaces 1108 and minor surfaces 1110 of the electrode. The wet bonding material is applied evenly and uniformly to the surface of the electrode. While the wet bonding material is still substantially wet, a plurality of dry anti-microbial particles 1118 are applied to the wet bonding material 1116 as shown in FIG. 13B. The dry anti-microbial particles engage and are at least partially embedded in the wet bonding material 1116. The wet bonding material 1116 therefore causes the anti-microbial particles 1118 to adhere to the surface of the electrode 1102.

Figure 13D:
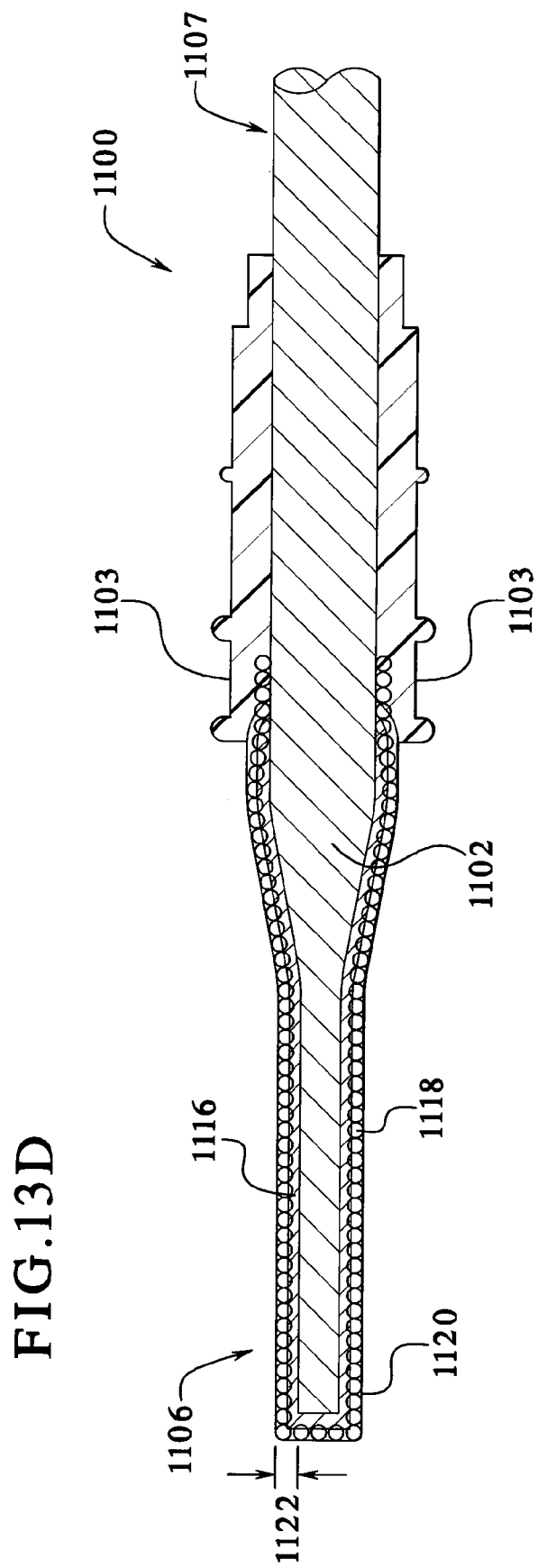
FIG. 13D is a cross-section view of the embodiment of FIG. 13C taken generally along the line 13D-13D.

In one embodiment, a top coating 1120 is applied over the layer of anti-microbial particles 1118 so that the top coating completely and fully coats the layer of anti-microbial particles on the surface of the electrode. As shown in FIG. 13C, the top coating 1120 is applied so that the anti-microbial particles are exposed at the surfaces of the electrode. Therefore when bacteria and other organisms contact the exposed anti-microbial particles on the surfaces of the electrode, the bacteria and organisms are killed. In this embodiment, the top coating is not applied to the surfaces of the electrode covered by the insulative or plastic material 1103 as shown in FIG. 13D. This fully exposes the maximum amount of anti-microbial particles underneath at least a portion of the insulative material 1103 to kill a substantial portion of the harmful organisms, which may enter a gap between the electrode and the insulative material and get underneath the insulative material.

In another embodiment, a partial top coating is applied to the layer of anti-microbial particles so that some or all of the anti-microbial particles protrude from or are otherwise exposed on the surfaces of the electrode. Because a greater amount of the surfaces or surface area of the anti-microbial particles are exposed on the surfaces of the electrode, the anti-microbial particles are more effective in minimizing and killing any bacteria or other organisms which contact the surfaces of the electrode.

In a further embodiment, the top coating is applied to the surfaces of the electrode to completely coat or cover the anti-microbial particle layer as described above. A buffer or sander is then used to sand down or remove a portion of the top coating to expose some or all of the anti-microbial particles at the surfaces of the electrode. This method also enhances the contacting of bacteria and other organisms with the anti-microbial particles to kill these harmful organisms. It should be appreciated that the top coating could be partially removed by buffing, sanding or using any other suitable material sanding method.

In another embodiment, powdered silver or a partial powdered silver coating or "dusting" is applied to the primer coating on the surfaces of the electrode. In this embodiment, a designated amount or metered amount of powdered silver or suitable anti-microbial particles is applied to the primer layer so that the powdered silver particles are not touching each other once the powdered particles are applied to and embedded in the primer or base coating on the surfaces of the electrode. The powdered silver particles sink in the primer coating so that at least a portion of the particles are protruding from or otherwise exposed on the surfaces of the electrode. In this embodiment, a top coating would not be applied to the powdered silver particles. In one embodiment, a suitable solvent is then applied to the powdered silver particles to enhance the sinking or embedding of the particles into the wet bonding material layer or primer layer. It should be appreciated that any suitable amount of the powdered silver coating may be applied to the surfaces of the electrode.

In one embodiment, the top coating includes a non-stick material. The non-stick material includes at least one of the following materials: silicone, polytetrafluoroethylene, fluoropolymers, and combinations of fluorosilicones. In different embodiments, the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

It should be appreciated that any suitable non-stick material may be applied to the anti-microbial particles. It should also be appreciated that any other suitable top coating may be applied to the anti-microbial particles. Once the top coating is applied to the anti-microbial particles, the coated electrode is cured in a suitable curing oven, furnace or by a suitable curing method or process as described above. The oven dries, sinters or cures the coated electrode and thereby enhances the adhesion of the coatings on the electrode, which causes the coatings and dry anti-microbial particles to adhere to the surface of the electrode 1102. In this embodiment, the top coating is applied to the electrode so that at least a portion of the anti-microbial particles are exposed at the surface of the coated electrode 1102. Additionally, the top coating is not applied to the anti-microbial particles underneath at least a portion of the insulative material. This fully exposes the anti-microbial particles underneath this portion of the insulative material and prevents harmful organisms from getting underneath the insulative material and growing or cultivating. Both the coating on the electrode and the fully exposed anti-microbial particles underneath the insulative material minimizes and/or prevents bacteria and other harmful organisms from remaining and growing on the surface of the electrode 1102 by killing a substantial portion of these organisms when the organisms come in contact with the anti-microbial particles. It should be appreciated that the anti-microbial particles are uniformly and completely exposed at the surface of the electrode so that any organisms that contact the surfaces of the electrode contact the exposed anti-microbial particles. The coatings may be applied to the surface of the electrode 1102 to a desired thickness 1122 as shown in FIG. 13D. In one embodiment, the primer coating, the anti-microbial particles, and the top coating are repeatedly applied to the surface of the electrode until a designated or desired thickness is achieved. After the desired thickness is achieved, the coated electrode is at least partially cured in a suitable curing oven. It should be appreciated that any suitable number of coatings may be applied to the surface of the electrode. It should also be appreciated that any suitable mixture or combination of coatings such as multiple powdered coatings including PTFE, MFA, anti-microbial coatings or any other suitable coatings may be applied to the surface of the electrode.

As described above, the anti-microbial particles applied to the surface or surfaces of the electrode prevent a substantial portion of the bacteria and other harmful organisms from remaining and growing on the surfaces of the electrode by killing a majority of the bacteria and other harmful organisms when these organisms contact the exposed anti-microbial particles on the surfaces of the electrode. The anti-microbial particles therefore enable the electrosurgical blade to be used multiple times in the same or different surgical procedures with a greater degree of safety as the proven anti-microbial properties will reduce or kill a substantial portion of the harmful organisms. The electrosurgical electrode is also substantially durable so that it may be sterilized when necessary. As a result, the coated anti-microbial electrosurgical electrode of the present invention is essentially cleaner and safer for surgical procedures and especially for surgical procedures where sterilization of surgical tools is improperly performed, inconsistent or non-existent. It should be appreciated that the coating, coatings and methods of applying the coating or coatings to the surface of the electrode may be used to apply a coating or coatings to any medical devices, medical tools, medical attachments, medical components or medical instruments.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. An electrosurgical electrode connectible to a handle, said electrosurgical electrode comprising:
    a conductive substrate;
    at least one substantially uniform coating applied to said substrate, wherein the coating includes a cured base material having a plurality of anti-microbial particles interspersed in said base material, wherein said anti-microbial particles are at least partially electrostatically bonded to said base material and are formulated to kill a microbial organism independent of any energy source; and
    a top coating applied to the substantially uniform coating.

2. The electrosurgical electrode of claim 1, wherein the conductive substrate includes a metal.

3. The electrosurgical electrode of claim 2, wherein the metal includes stainless steel.

4. The electrosurgical electrode of claim 1, which includes an electrically insulative material applied to at least a portion of a surface of the conductive substrate.

5. The electrosurgical electrode of claim 4, wherein a portion of the conductive substrate underneath the electrically insulative material includes the substantially uniform coating.

6. The electrosurgical electrode of claim 1, wherein the top coating includes a non-stick material.

7. The electrosurgical electrode of claim 6, wherein the non-stick material includes at least one of the non-stick materials selected from the group consisting of: a silicone, a polytetrafluoroethylene, a fluoropolymer, a ceramic and a combination of fluorosilicones.

8. The electrosurgical electrode of claim 1, wherein the top coating includes at least one of the following powdered coatings selected from the group consisting of: polytetrafluoroethylene, perfluoroalkoxy, tetrafluoroethylene perfluoromethyl vinyl ether copolymer and fluorinated ethylene propylene.

9. The electrosurgical electrode of claim 1, wherein the anti-microbial particles include at least one of the group consisting of: silver particles, ceramic particles and a combination of silver and ceramic particles.

10. The electrosurgical electrode of claim 1, wherein the anti-microbial particles includes silver particles.

11. The electrosurgical electrode of claim 10, wherein a first quantity of anti-microbial particles in the substantially uniform coating is formulated to conduct electricity a first amount and a second, greater quantity of anti-microbial particles in the substantially uniform coating is formulated to conduct electricity a second, greater amount.

12. The electrosurgical electrode of claim 10, wherein a first density of anti-microbial particles applied to a surface of the substrate is formulated to conduct electricity a first amount and a second, greater density of anti-microbial particles applied to the surface of the substrate is formulated to conduct electricity a second, greater amount.

13. The electrosurgical electrode of claim 1, wherein at least part of the conductive substrate forms a shape selected from the group consisting of: a blade, a scalpel, a needle, a probe, a knife, a wire and a ball.

14. The electrosurgical electrode of claim 1, wherein the base material is electrostatically grounded.

15. The electrosurgical electrode of claim 1, wherein the anti-microbial particles are electrostatically charged.

16. The electrosurgical electrode of claim 1, which includes a plurality of different sized anti-microbial particles.

17. The electrosurgical electrode of claim 1, wherein at least one of the anti-microbial particles is a shape selected from the group consisting of: flat-shaped, flake-shaped, angular-shaped, cylindrical-shaped, oblong-shaped and leaf-shaped particles.

18. The electrosurgical electrode of claim 1, wherein a portion of the anti-microbial particles are exposed at a surface of the conductive substrate.

19. The electrosurgical electrode of claim 1, wherein a portion of each of a plurality of the anti-microbial particles protrude from the top coating.

20. The electrosurgical electrode of claim 1, wherein a portion of each of a plurality of the anti-microbial particles protrude from the substantially uniform coating.

21. An electrosurgical device including an electrode, a handle connected to the electrode and an electrical source in communication with the handle to transfer electrical energy to the electrode for contacting tissue in a body during an electrosurgical procedure, said electrode comprising:
- a conductive substrate;
- a wet bonding material applied to the surface of the substrate;
- a single layer of substantially uniform anti-microbial particles applied to the wet bonding material, wherein said anti-microbial particles are at least partially electrostatically bonded to the wet bonding material and are formulated to kill a microbial organism independent of any energy source; and
- a top coating applied to the layer of anti-microbial particles, wherein a portion of the anti-microbial particles are exposed at the surface of the conductive substrate.

22. The electrosurgical device of claim 21, wherein the conductive substrate includes a metal.

23. The electrosurgical device of claim 22, wherein the metal includes stainless steel.

24. The electrosurgical device of claim 21, which includes an electrically insulative material applied to at least a portion of a surface of the conductive substrate.

25. The electrosurgical device of claim 22, wherein a portion of the conductive substrate underneath the electrically insulative material includes the layer of substantially uniform anti-microbial particles.

26. The electrosurgical device of claim 21, wherein the top coating includes a non-stick material.

27. The electrosurgical device of claim 26, wherein the non-stick material includes at least one of the non-stick materials selected from the group consisting of: a silicone, a polytetrafluoroethylene, a fluoropolymer, a ceramic and a combination of fluorosilicones.

28. The electrosurgical device of claim 21, wherein the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

29. The electrosurgical device of claim 21, wherein the anti-microbial particles include at least one of the group consisting of: silver particles, ceramic particles and a combination of silver and ceramic particles.

30. The electrosurgical device of claim 21, wherein at least part of the conductive substrate forms a shape selected from the group consisting of: a blade, a scalpel, a needle, a probe, a knife, a wire and a ball.

31. The electrosurgical device of claim 21, which includes a plurality of different sized anti-microbial particles.

32. The electrosurgical device of claim 21, wherein at least one of the anti-microbial particles is a shape selected from the group consisting of: flat-shaped, flake-shaped, angular-shaped, cylindrical-shaped, oblong-shaped and leaf-shaped particles.

33. A method of coating an electrosurgical device including a conductive substrate, said method comprising:
- (a) applying a substantially uniform coating to a surface of the conductive substrate, said coating including a base material having a plurality of anti-microbial particles interspersed in said base material, wherein said anti-microbial particles are at least partially electrostatically bonded to the base material and are formulated to kill a microbial organism independent of any energy source;
- (b) at least partially curing the base material and the anti-microbial particles interspersed in the base material; and
- (c) applying a top coating to the base material and the anti-microbial particles interspersed in the base material.

34. The method of claim 33, which includes repeating (a) to (b) until a desired thickness is achieved.

35. The method of claim 33, wherein the anti-microbial particles include at least one of the group consisting of: silver particles, ceramic particles and a combination of silver and ceramic particles.

36. The method of claim 33, which includes applying an electrically insulative material to at least a portion of the surface of the conductive substrate.

37. The method of claim 36, which includes applying the substantially uniform coating to a portion of the surface of the conductive substrate which is underneath the insulative material.

38. The method of claim 33, which includes applying a wet bonding material to the surface of the conductive substrate prior to applying the substantially uniform coating to the surface of the conductive substrate.

39. The method of claim 38, wherein the wet bonding material includes a primer.

40. The method of claim 33, wherein the top coating includes a non-stick material.

41. The method of claim 40, wherein the non-stick material includes at least one of the non-stick materials selected from the group consisting of: a silicone, a polytetrafluoroethylene, a fluoropolymer, a ceramic and a combination of fluorosilicones.

42. The method of claim 33, wherein the top coating includes at least one of the following powdered coatings selected from the group consisting of:
polytetrafluoroethylene, perfluoroalkoxy, tetrafluoroethylene perfluoromethyl vinyl ether copolymer and fluoronated ethylene propylene.

43. The method of claim 33, which includes removing at least a portion of the top coating to expose a portion of the anti-microbial particles at the surface of the conductive substrate.

44. The method of claim 33, wherein the base material is electrostatically grounded.

45. The method of claim 33, wherein the anti-microbial particles are electrostatically charged.

46. The method of claim 33, which includes a plurality of different sized anti-microbial particles.

47. The method of claim 33, wherein at least one of the anti-microbial particles is a shape selected from the group consisting of: flat-shaped, flake-shaped, angular-shaped, cylindrical-shaped, oblong-shaped and leaf-shaped particles.

48. The method of claim 33, wherein applying the substantially uniform coating to the surface of the conductive substrate includes applying powdered anti-microbial particles.

49. The method of claim 33, which includes removing at least a portion of the top coating to expose a portion of each of a plurality of the anti-microbial particles protruding from the top coating.

50. The method of claim 33, which includes removing at least a portion of the top coating to expose a portion of each of a plurality of the anti-microbial particles protruding from the substantially uniform coating.

51. The method of claim 33, which includes grit-blasting the surface of the conductive substrate prior to applying the substantially uniform coating.

52. The method of claim 33, which includes applying a coating of anti-microbial particles to the applied substantially uniform coating prior to at least partially curing the base material and the anti-microbial particles interspersed in the base material.

53. A method of coating an electrosurgical device including a conductive substrate, said method comprising:

(a) applying a wet bonding material to at least a portion of a surface of the conductive substrate;
(b) evenly applying a single layer of substantially uniform anti-microbial particles to the wet bonding material, wherein said anti-microbial particles are at least partially electrostatically bonded to the wet bonding material and are formulated to kill a microbial organism independent of any energy source;
(c) at least partially curing the wet bonding material and the substantially uniform anti-microbial particles; and
(d) partially applying a top coating to the bonding material and the anti-microbial particles such that a portion of the anti-microbial particles are exposed at the surface of the conductive substrate.

54. The method of claim 53, which includes repeating (a) to (c) until a desired thickness is achieved.

55. The method of claim 53, wherein the anti-microbial particles include at least one of the group consisting of: silver particles, ceramic particles and a combination of silver and ceramic particles.

56. The method of claim 53, which includes applying an electrically insulative material to at least a portion of the surface of the conductive substrate.

57. The method of claim 56, which includes applying the substantially uniform coating to a portion of the surface of the conductive substrate which is underneath the insulative material.

58. The method of claim 53, wherein the wet bonding material includes a primer.

59. The method of claim 53, wherein the top coating includes a non-stick material.

60. The method of claim 59, wherein the non-stick material includes at least one of the non-stick materials selected from the group consisting of: a silicone, a polytetrafluoroethylene, a fluoropolymer, a ceramic and a combination of fluorosilicones.

61. The method of claim 53, wherein the top coating includes at least one of the following powdered coatings selected from the group consisting of:
polytetrafluoroethylene, perfluoroalkoxy, tetrafluoroethylene perfluoromethyl vinyl ether copolymer and fluoronated ethylene propylene.

62. The method of claim 53, wherein applying a single layer of substantially uniform anti-microbial particles to the wet bonding material includes applying powdered anti-microbial particles.

63. The method of claim 53, wherein applying the wet bonding material to the surface of the conductive substrate includes selectively coating specific portions of the surface of the substrate.

64. The method of claim 53, which includes grit-blasting at least a portion of the surface of the conductive substrate prior to applying the wet bonding material.

65. The method of claim 53, which includes repeating (b) until a desired thickness is achieved.

66. An electrosurgical electrode connectible to a handle, said electrosurgical electrode comprising:
a conductive substrate;
a wet bonding material applied to the surface of the substrate;
a layer of substantially uniform anti-microbial particles applied to the wet bonding material, wherein said anti-microbial particles are at least partially electrostatically bonded to the wet bonding material and are formulated to kill a microbial organism independent of any energy source; and
a top coating at least partially applied to the layer of anti-microbial particles, wherein a portion of each of a plurality of the anti-microbial particles protrude from the top coating.

67. The electrosurgical electrode of claim 66, wherein the conductive substrate includes a metal.

68. The electrosurgical electrode of claim 66, wherein the metal includes stainless steel.

69. The electrosurgical electrode of claim 66, which includes an electrically insulative material applied to at least a portion of a surface of the conductive substrate.

70. The electrosurgical electrode of claim 69, wherein a portion of the conductive substrate underneath the electrically insulative material includes the layer of substantially uniform anti-microbial particles.

71. The electrosurgical electrode of claim 66, wherein the top coating includes a non-stick material.

72. The electrosurgical electrode of claim 71, wherein the non-stick material includes at least one of the non-stick materials selected from the group consisting of: a silicone, a polytetrafluoroethylene, a fluoropolymer, a ceramic and a combination of fluorosilicones.

73. The electrosurgical electrode of claim 66, wherein the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

74. The electrosurgical electrode of claim 66, wherein the anti-microbial particles include at least one of the group consisting of: silver particles, ceramic particles and a combination of silver and ceramic particles.

75. The electrosurgical electrode of claim 66, wherein at least part of the conductive substrate forms a shape selected from the group consisting of: a blade, a scalpel, a needle, a probe, a knife, a wire and a ball.

76. The electrosurgical electrode of claim 66, which includes a plurality of different sized anti-microbial particles.

77. The electrosurgical electrode of claim 66, wherein at least one of the anti-microbial particles is a shape selected from the group consisting of: flat-shaped, flake-shaped, angular-shaped, cylindrical-shaped, oblong-shaped and leaf-shaped particles.

78. An electrosurgical electrode connectible to a handle, said electrosurgical electrode comprising:
a conductive substrate;
a wet bonding material applied to the surface of the substrate;
a layer of substantially uniform anti-microbial particles applied to the wet bonding material, wherein said anti-microbial particles are at least partially electrostatically bonded to the wet bonding material and are formulated to kill a microbial organism independent of any energy source; and
a top coating applied to the layer of anti-microbial particles, wherein a portion of each of a plurality of the anti-microbial particles protrude from the wet bonding material.

79. The electrosurgical electrode of claim 78, wherein the conductive substrate includes a metal.

80. The electrosurgical electrode of claim 78, wherein the metal includes stainless steel.

81. The electrosurgical electrode of claim 78, which includes an electrically insulative material applied to at least a portion of a surface of the conductive substrate.

82. The electrosurgical electrode of claim 81, wherein a portion of the conductive substrate underneath the electrically insulative material includes the layer of substantially uniform anti-microbial particles.

83. The electrosurgical electrode of claim 78, wherein the top coating includes a non-stick material.

84. The electrosurgical electrode of claim 83, wherein the non-stick material includes at least one of the non-stick materials selected from the group consisting of: a silicone, a polytetrafluoroethylene, a fluoropolymer, a ceramic and a combination of fluorosilicones.

85. The electrosurgical electrode of claim 78, wherein the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

86. The electrosurgical electrode of claim 78, wherein the anti-microbial particles include at least one of the group consisting of: silver particles, ceramic particles and a combination of silver and ceramic particles.

87. The electrosurgical electrode of claim 78, wherein at least part of the conductive substrate forms a shape selected from the group consisting of: a blade, a scalpel, a needle, a probe, a knife, a wire and a ball.

88. The electrosurgical electrode of claim 78, which includes a plurality of different sized anti-microbial particles.

89. The electrosurgical electrode of claim 78, wherein at least one of the anti-microbial particles is a shape selected from the group consisting of: flat-shaped, flake-shaped, angular-shaped, cylindrical-shaped, oblong-shaped and leaf-shaped particles.

90. A method of coating an electrosurgical device including a conductive substrate, said method comprising:
（a) applying a wet bonding material to at least a portion of a surface of the conductive substrate;
(b) evenly applying a layer of substantially uniform anti-microbial particles to the wet bonding material, wherein said anti-microbial particles are at least partially electrostatically bonded to the wet bonding material and are formulated to kill a microbial organism independent of any energy source;
(c) at least partially curing the wet bonding material and the substantially uniform anti-microbial particles; and
(d) partially applying a top coating to the bonding material and the anti-microbial particles such that a portion of each of a plurality of the anti-microbial particles protrude from the top coating.

91. The method of claim 90, which includes repeating (a) to (c) until a desired thickness is achieved.

92. The method of claim 90, wherein the anti-microbial particles include at least one of the group consisting of: silver particles, ceramic particles and a combination of silver and ceramic particles.

93. The method of claim 90, which includes applying an electrically insulative material to at least a portion of the surface of the conductive substrate.

94. The method of claim 93, which includes applying the substantially uniform coating to a portion of the surface of the conductive substrate which is underneath the insulative material.

95. The method of claim 90, wherein the wet bonding material includes a primer.

96. The method of claim 90, wherein the top coating includes a non-stick material.

97. The method of claim 96, wherein the non-stick material includes at least one of the non-stick materials selected from the group consisting of: a silicone, a polytetrafluoroethylene, a fluoropolymer, a ceramic and a combination of fluorosilicones.

98. The method of claim 90, wherein the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

99. The method of claim 90, wherein applying a layer of substantially uniform anti-microbial particles to the wet bonding material includes applying powdered anti-microbial particles.

100. The method of claim 90, wherein applying the wet bonding material to the surface of the conductive substrate includes selectively coating specific portions of the surface of the substrate.

101. The method of claim 90, which includes grit-blasting at least a portion of the surface of the conductive substrate prior to applying the wet bonding material.

102. The method of claim 90, which includes repeating (b) until a desired thickness is achieved.

103. A method of coating an electrosurgical device including a conductive substrate, said method comprising:
(a) applying a wet bonding material to at least a portion of a surface of the conductive substrate;
(b) evenly applying a layer of substantially uniform anti-microbial particles to the wet bonding material, wherein said anti-microbial particles are at least partially electrostatically bonded to the wet bonding material and are formulated to kill a microbial organism independent of any energy source;
(c) at least partially curing the wet bonding material and the substantially uniform anti-microbial particles; and
(d) at least partially applying a top coating to the bonding material and the anti-microbial particles such that a portion of each of a plurality of the anti-microbial particles protrude from the wet bonding material.

104. The method of claim 103, which includes repeating (a) to (c) until a desired thickness is achieved.

105. The method of claim 103, wherein the anti-microbial particles include at least one of the group consisting of: silver particles, ceramic particles and a combination of silver and ceramic particles.

106. The method of claim 103, which includes applying an electrically insulative material to at least a portion of the surface of the conductive substrate.

107. The method of claim 106, which includes applying the substantially uniform coating to a portion of the surface of the conductive substrate which is underneath the insulative material.

108. The method of claim 103, wherein the wet bonding material includes a primer.

109. The method of claim 103, wherein the top coating includes a non-stick material.

110. The method of claim 109, wherein the non-stick material includes at least one of the non-stick materials selected from the group consisting of: a silicone, a polytetrafluoroethylene, a fluoropolymer, a ceramic and a combination of fluorosilicones.

111. The method of claim 103, wherein the top coating includes at least one of the following powdered coatings selected from the group consisting of: polytetrafluoroethylene, perfluoroalkoxy, tetrafluoroethylene perfluoromethyl vinyl ether copolymer and fluoronated ethylene propylene.

112. The method of claim 103, wherein applying a layer of substantially uniform anti-microbial particles to the wet bonding material includes applying powdered anti-microbial particles.

113. The method of claim 103, wherein applying the wet bonding material to the surface of the conductive substrate includes selectively coating specific portions of the surface of the substrate.

114. The method of claim 103, which includes grit-blasting at least a portion of the surface of the conductive substrate prior to applying the wet bonding material.

115. The method of claim 103, which includes repeating (b) until a desired thickness is achieved.

* * * * *